(12) United States Patent
Druilhe et al.

(10) Patent No.: US 7,498,037 B2
(45) Date of Patent: Mar. 3, 2009

(54) PLASMODIUM FALCIPARUM ANTIGENS AND THEIR VACCINE AND DIAGNOSTIC APPLICATIONS

(75) Inventors: Pierre Druilhe, Paris (FR); Anne-Charlotte Grüner, Paris (FR)

(73) Assignee: Institut Pasteur, Paris (FR)

( * ) Notice: Subject to any disclaimer, the term of this patent is extended or adjusted under 35 U.S.C. 154(b) by 712 days.

(21) Appl. No.: 10/712,533

(22) Filed: Nov. 14, 2003

(65) Prior Publication Data

US 2005/0075496 A1   Apr. 7, 2005

(51) Int. Cl.
| | |
|---|---|
| A61K 39/00 | (2006.01) |
| A61K 39/38 | (2006.01) |
| A61K 39/015 | (2006.01) |
| A61K 33/06 | (2006.01) |
| A61K 39/002 | (2006.01) |
| A61K 38/00 | (2006.01) |
| A61K 38/16 | (2006.01) |
| A01N 59/06 | (2006.01) |
| A01N 37/18 | (2006.01) |
| C07K 14/00 | (2006.01) |
| C07K 16/00 | (2006.01) |
| C07K 17/00 | (2006.01) |
| C07K 2/00 | (2006.01) |
| C07K 4/00 | (2006.01) |
| C07K 5/00 | (2006.01) |
| C07K 7/00 | (2006.01) |

(52) U.S. Cl. ............... 424/272.1; 424/184.1; 424/268.1; 424/690; 424/698; 424/265.1; 530/300; 530/350

(58) Field of Classification Search .................. None
See application file for complete search history.

(56) References Cited

U.S. PATENT DOCUMENTS 6,191,270 B1    2/2001   Druilhe et al.

FOREIGN PATENT DOCUMENTS

WO      WO 00/25728        5/2000

OTHER PUBLICATIONS

EMBL database; Accession No. 096134; Entry Name 096134-PLAF7; Created: May 1, 1999, Sequence Update: Mar. 1, 2003; Annotation Update: Mar. 1, 2004.
International Search Report from Corresponding PCT Application No. PCT/FR02/01637.
Daubersies et al., Protection against *Plasmodium falciparum* malaria in chimpanzees by immunization with the conserved pre-erythrocytic liver-stage antigen 3, (2000) Nature Medicine, 6:11, 1258-1263.
Benohamed et al., High immunogenicity in chimpanzees of peptides and lipopeptides derived from four new *Plasmodium falciparum* pre-erythrocytic molecules, (2000) Vaccine 18, 2843-2855.
Gardner et al., Chromosome 2 sequence of the human malaria parasite *Plasmodium falciparum*, (1998) Science 282, 1126-1132.
Database EMBL XP-002222214, *Plasmodium falciparum* 3D7 chromosome 2 section 13 or 73 of the complete sequence (Nov. 9, 1998).
Database EMBL XP-002222215, *Plasmodium falciparum* 3D7 cDNA 5' (Dec. 22, 2001).

*Primary Examiner*—N. M Minnifield
(74) *Attorney, Agent, or Firm*—Finnegan, Henderson, Farabow, Garrett & Dunner, LLP

(57) ABSTRACT

The invention concerns novel *Plasmodium falciparum* antigens and their vaccine and diagnostic applications. More particularly, the invention concerns immunogenic polynucleotide and polypeptide molecules, compositions comprising them, and methods for diagnosis and vaccination of malaria.

13 Claims, 28 Drawing Sheets

FIGURE 1A: SEQ ID NO 1 (DG747)

```
  1 GAATTCCATA TGCACGATTA CATATATGAT GATCGTATCT ACAATAATGA TAAAGAGAAA
 61 AATGTTATAA AAAGTGATAA TAAAAATGTT ATAAAAAGTG ATAATAAAAA TGATTATAAA
121 AAGTGTAATA AAAATGTTAT AAAAAGTGAT AATAAAAATG TTATAAAAAG TGATAATAAA
181 AATGTGGAAT TC
```

FIGURE 1B: SEQ ID NO 2 (DG772)

```
  1 GAATTCCCAG ATCCTCGAAG TAATGACCAA GAAGATGCTA CTGACGATGT TGTAGAAAAT
 61 AGTAGAGATG ATAATAATAG TCTCTCTAAT AGCGTAGATA ATCAAAGTAA TGTTTTAAAT
121 AGAGAAGATC CTATTGCTTC TGAAACTGAA GTTGTAAGTG AACCTGAGGA TTCAAGTAGG
181 ATAATGACTA CAGAAGTTCC AAGTACTACT GTAAAACCCC CTGATGAAAA ACGATCTGAA
241 GAAGTAGGAG AAAAAGAAGC TAAAGAAATT AAAGTAGAAC CTGTTGTACC AAGAGCCATT
301 GGAGAACCAA TGGAAAATTC TGTGAGCGTA CAGTCCCCTC CTAAGGAATT C
```

FIGURE 1C: SEQ ID NO 3 (DG747)

```
 1 EFHMHDYIYD DRIYNNDKEK NVIKSDNKNV IKSDNKNDYK KCNKNVIKSD NKNVIKSDNK
61 NVEF
```

FIGURE 1D: SEQ ID NO 4 (DG772)

```
 1 EFPDPRSNDQ EDATDDVVEN SRDDNNSLSN SVDNQSNVLN REDPIASETE VVSEPEDSSR
61 IMTTEVPSTT VKPPDEKRSE EVGEKEAKEI KVEPVVPRAI GEPMENSVSV QSPPKEF
```

FIGURE 1E: SEQ ID NOs 5-8:

SEQ ID NO 5: DNKNV

SEQ ID NO 6: DNKND

SEQ ID NO 7: DKEKNV

SEQ ID NO 8: KSDNKNV

FIGURE 2A:

```
            10         20         30         40         50         60         70
            |          |          |          |          |          |          |
ATGAAGACGACAAAAGAAAATGACAATAATAACATAGTACATTATGTAGATTGGATAAACCAGATTTTTAAAAAGAAT
 M  K  T  T  K  E  N  D  N  N  N  I  V  H  Y  V  D  W  I  N  Q  I  F  K  K  N
 •  R  R  Q  K  K  M  T  I  I  T  •  Y  I  M  •  I  G  •  T  R  F  L  K  R  I
   E  D  D  K  R  K  •  Q  •  •  H  S  T  L  C  R  L  D  K  P  D  F  •  K  E  F 80         90        100        110        120        130        140        150
            |          |          |          |          |          |          |          |
TCTTTACAATGTGATTTATATTTTTTGGATGACAACAAAGAAAAAGATGTTAGTAAGAAAAGAAAAGCTCAATTGAAG
 S  L  Q  C  D  L  Y  F  L  D  D  N  K  E  K  D  V  S  K  K  R  K  A  Q  L  K
 L  Y  N  V  I  Y  I  F  W  M  T  T  K  K  K  M  L  V  R  K  E  K  L  N  •  R
   F  T  M  •  F  I  F  F  G  •  Q  Q  R  K  R  C  •  •  E  K  K  S  I  E  G 160        170        180        190        200        210        220        230
            |          |          |          |          |          |          |          |
GATGAATATGATAATATATCAAGGAGCAAAGAAAATATTAATAATTCCAAAAAAATAAAAAATGAATTAAGTATAAAA
 D  E  Y  D  N  I  S  R  S  K  E  N  I  N  N  S  K  K  I  K  N  E  L  S  I  K
 M  N  M  I  I  Y  Q  G  A  K  K  I  L  I  I  P  K  K  •  K  M  N  •  V  •  K
   •  I  •  •  Y  I  K  E  Q  R  K  Y  •  •  F  Q  K  N  K  K  •  I  K  Y  K  R 240        250        260        270        280        290        300        310
            |          |          |          |          |          |          |          |
GATAATATGCACGATTACATATATGATGATCGTATCTACAATAATGATAAAGAGAAAAATGTTATAAAAAGTGATAAT
 D  N  M  H  D  Y  I  Y  D  D  R  I  Y  N  N  D  K  E  K  N  V  I  K  S  D  N
 I  I  C  T  T  T  Y  M  M  T  V  S  T  T  M  I  K  R  K  M  L  •  K  V  I  I
   •  Y  A  R  L  H  I  •  •  S  Y  L  Q  •  •  •  R  E  K  C  Y  K  K  •  •  •
```

FIGURE 2A (suite)

```
       320        330        340        350        360        370        380        390
AAAAATGTTATAAAAAGTGATAATAAAAATGATTATAAAAAGTG(A)TAATAAAAATGTTATAAAAAGTGATAATAAAAAT
 K  N  V  I  K  S  D  N  K  N  V  I  K  S  D  N     K  N  V  I  K  S  D  N  K  N
  K  M  L  •  K  V  I  I  K  M  DL  •  K  V  CI  I  K  M  L  •  K  V  I  I  K  M
   K  C  Y  K  K  •  •  •  K  C  Y  K  K  •  •  •  K  C  Y  K  K  •  •  •  K  C 400        410        420       430        440        450        460
GTTATAAAAAGTGATAATAAAAATGTTATA AAAAGTGATAATAAAAATGTTATAAAAAGTGATTATAAAAGTGATGAT
 V  I  K  S  D  N  K  N  V  I  K  S  D  N  K  N  V  I  K  S  D  Y  K  S  D  D
  L  •  K  V  I  I  K  M  L  •  K  V  I  I  K  M  L  •  K  V  I  I  K  V  M  I
   Y  K  K  •  •  •  K  C  Y  K  K  •  •  •  K  C  Y  K  K  •  L  •  K  •  •  •

470        480        490        500        510        520        530        540
AGAAATGCTTGTGATATTTATAAAAGTAATAAAAAAAAATGTTCCTGATAATTGCCATATATATGATGATAATAGTTCA
 R  N  A  C  D  I  Y  K  S  N  K  K  N  V  P  D  N  C  H  I  Y  D  D  N  S  S
  E  M  L  V  I  F  I  K  V  I  K  K  M  F  L  I  I  A  I  Y  M  M  I  I  V  Q
   K  C  L  •  Y  L  •  K  •  •  K  K  C  S  •  •  L  P  Y  I  •  •  •  •  F  S 550        560        570        580        590        600        610        620
GTTGAAAATTTAGATGGAAAAAATAAATTAAATAATATAAGGAACATACATAATGATAACTCATCTTCATGCGATATA
 V  E  N  L  D  G  K  N  K  L  N  N  I  R  N  I  H  N  D  N  S  S  S  C  D  I
  L  K  I  •  M  E  K  I  N  •  I  I  •  G  T  Y  I  M  I  T  H  L  H  A  I  Y
   •  K  F  R  W  K  K  •  I  K  •  Y  K  E  H  T  •  •  •  L  I  F  M  R  Y  I 630        640        650        660        670        680        690        700
TCCGATATAAAAAGTGAAGATGAATATATAGAACCATATGAAAAAAAGAATGAAGAAAATATAAATGAATATAAGAAT
 S  D  I  K  S  E  D  E  Y  I  E  P  Y  E  K  K  N  E  E  N  I  N  E  Y  K  N
  P  I  •  K  V  K  M  N  I  •  N  H  M  K  K  R  M  K  K  I  •  M  N  I  R  I
   R  Y  K  K  •  R  •  I  Y  R  T  I  •  K  K  E  •  R  K  Y  K  •  I  •  E  •
```

FIGURE 2A (suite)

```
         710       720       730       740       750       760       770       780
          |         |         |         |         |         |         |         |
AAGAAAAATATAGCCAATGAAAATATAAAAGAAGGAAAGAGTTCAATTTATAATGATGAACATAATTATAATTCATTA
 K   K   N   I   A   N   E   N   I   K   E   G   K   S   S   I   Y   N   D   E   H   N   Y   N   S   L
   R   K   I   •   P   M   K   I   •   K   K   E   R   V   Q   F   I   M   M   N   I   I   I   H   Y
     E   K   Y   S   Q   •   K   Y   K   R   R   K   E   F   N   L   •   •   •   T   •   L   •   F   I   I 790       800       810       820       830       840       850
          |         |         |         |         |         |         |
TTATATAATTCTTGTAATGGTGAAATAAGTAAGATCAACAAAATAAGTAGTCATAATAATATTGATAATAATATGGAT
 L   Y   N   S   C   N   G   E   I   S   K   I   N   K   I   S   S   H   N   N   I   D   N   N   M   D
   Y   I   I   L   V   M   V   K   •   V   R   S   T   K   •   V   V   I   I   I   L   I   I   I   W   I
     I   •   F   L   •   W   •   N   K   •   D   Q   Q   N   K   •   S   •   •   Y   •   •   •   Y   G   •

860       870       880       890       900       910       920       930
    |         |         |         |         |         |         |         |
AATTATAATACGTTTGCAAATGTGAATAATTTTATAATATATTCCTCAGATGATGAAGATAATATATCAAATTATTAT
 N   Y   N   T   F   A   N   V   N   N   F   I   I   Y   S   S   D   D   E   D   N   I   S   N   Y   Y
   I   I   I   R   L   Q   M   •   I   I   L   •   Y   I   P   Q   M   M   K   I   I   Y   Q   I   I   I
     L   •   Y   V   C   K   C   E   •   F   Y   N   I   F   L   R   •   •   R   •   Y   I   K   L   L   •

940       950       960       970       980       990      1000      1010
    |         |         |         |         |         |         |         |
AATGGTAAAGACGTATTAAATGATGAGATTATGTTCCCTATAAAATTTAATTTTGAAAAATTAAAAAAAAATATTTAT
 N   G   K   D   V   L   N   D   E   I   M   F   P   I   K   F   N   F   E   K   L   K   K   N   I   Y
   M   V   K   T   Y   •   M   M   R   L   C   S   L   •   N   L   I   L   K   N   •   K   K   I   F   M
     W   •   R   R   I   K   •   •   D   Y   V   P   Y   K   I   •   F   •   K   I   K   K   K   Y   L   C
```

FIGURE 2A (suite)

```
          1020      1030      1040      1050      1060      1070      1080      1090
           |         |         |         |         |         |         |         |
     GTAATAGAGCATATAGACAAAATATATTATGATACATTTTTAAATAAAAATCCAAGTGAAAAAAGTGTTTTTATGAAT
      V  I  E  H  I  D  K  I  Y  Y  D  T  F  L  N  K  N  P  S  E  K  S  V  F  M  N
       •  •  S  I  •  T  K  Y  I  M  I  H  F  •  I  K  I  Q  V  K  K  V  F  L  •  M
        N  R  A  Y  R  Q  N  I  L  •  Y  I  F  K  •  K  S  K  •  K  K  C  F  Y  E  •

1100      1110      1120      1130      1140      1150      1160      1170
           |         |         |         |         |         |         |         |
     GATGAATCTACTGGTTATTTGAAAAATGATGTGAATGACAAATGTGTTGTTGATAATATAAATGTTATTAATCCTTCT
      D  E  S  T  G  Y  L  K  N  D  V  N  D  K  C  V  V  D  N  I  N  V  I  N  P  S
       M  N  L  L  V  I  •  K  M  M  •  M  T  N  V  L  L  I  I  •  M  L  L  I  L  L
        •  I  Y  W  L  F  E  K  •  C  E  •  Q  M  C  C  •  •  Y  K  C  Y  •  S  F  •

1180      1190      1200      1210      1220      1230      1240
              |         |         |         |         |         |         |
     AGTGTGAATACGTTGAGTAATATTTCAAATATTAGGAATGAAAAAATAGAAAATAATAATAAGAATGAAAAATTAATA
      S  V  N  T  L  S  N  I  S  N  I  R  N  E  K  I  E  N  N  N  K  N  E  K  L  I
       V  •  I  R  •  V  I  F  Q  I  L  G  M  K  K  •  K  I  I  I  R  M  K  N  •  •
        C  E  Y  V  E  •  Y  F  K  Y  •  E  •  K  N  R  K  •  •  •  E  •  K  I  N  K 1250      1260      1270      1280      1290      1300      1310      1320
           |         |         |         |         |         |         |         |
     AAATCATATCCTACACAATCAAAAAATGTTATGAGTACATTTTCCTTTTGGAATATTGAAAAGGAGACATTTATAACA
      K  S  Y  P  T  Q  S  K  N  V  M  S  T  F  S  F  W  N  I  E  K  E  T  F  I  T
       N  H  I  L  H  N  Q  K  M  L  •  V  H  F  P  F  G  I  L  K  R  R  H  L  •  Q
        I  I  S  Y  T  I  K  K  C  Y  E  Y  I  F  L  L  E  Y  •  K  G  D  I  Y  N  K 1330      1340      1350      1360      1370      1380      1390      1400
           |         |         |         |         |         |         |         |
     AAACCTTTGTATGCACAAAATTTGAGAAAAAAACAATTTAGTTTATTAGATGAATCTGAAGAGATGATAAGAAATTAT
      K  P  L  Y  A  Q  N  L  R  K  K  Q  F  S  L  L  D  E  S  E  E  M  I  R  N  Y
       N  L  C  M  H  K  I  •  E  K  N  N  L  V  Y  •  M  N  L  K  R  •  •  E  I  I
        T  F  V  C  T  K  F  E  K  K  T  I  •  F  I  R  •  I  •  R  D  D  K  K  L  F
```

FIGURE 2A (suite)

```
        1410        1420        1430        1440        1450        1460        1470        1480
         |           |           |           |           |           |           |           |
TCATCTAATCAATATTCTATAAAATTTGTACCAAGACATTTATTATATGTAATGAGTCAAGTTGCTTCTCGATCCTTT
 S   S   N   Q   Y   S   I   K   F   V   P   R   H   L   L   Y   V   M   S   Q   V   A   S   R   S   F
   H   L   I   N   I   L   •   N   L   Y   Q   D   I   Y   Y   M   •   •   V   K   L   L   D   P   F
     I   •   S   I   F   Y   K   I   C   T   K   T   F   I   I   C   N   E   S   S   C   F   S   I   L   F 1490        1500        1510        1520
         |           |           |           |
TTTGATCCTTTATATAGAAAGCAGTTATTTTTTCGTTACTAA
 F   D   P   L   Y   R   K   Q   L   F   F   R   Y   •
   L   I   L   Y   I   E   S   S   Y   F   F   V   T
     •   S   F   I   •   K   A   V   I   F   S   L   L
```

Figure 2B:

```
            10        20        30        40        50        60        70
            |         |         |         |         |         |         |
ATGAAAGGGAAAATGAATATGTGTTTGTTTTTTTTCTATTCTATATTATATGTTGTATTATGTACCTATGTATTAGGT
  M  K  G  K  M  N  M  C  L  F  F  F  Y  S  I  L  Y  V  V  L  C  T  Y  V  L  G
 •  K  G  K  •  I  C  V  C  F  F  S  I  L  Y  Y  M  L  Y  Y  V  P  M  Y  •  V
    E  R  E  N  E  Y  V  F  V  F  F  L  F  Y  I  I  C  C  I  M  Y  L  C  I  R  Y 80        90       100       110       120       130       140       150
    |         |         |         |         |         |         |         |
ATAAGTGAAGAGTATTTGAAGGAAAGGCCCCAAGGTTTAAATGTTGAGACTAATAATAATAATAATAATAATAATAAT
  I  S  E  E  Y  L  K  E  R  P  Q  G  L  N  V  E  T  N  N  N  N  N  N  N  N
 •  V  K  S  I  •  R  K  G  P  K  V  •  M  L  R  L  I  I  I  I  I  I  I  I
    K  •  R  V  F  E  G  K  A  P  R  F  K  C  •  D  •  •  •  •  •  •  •  •  •

160       170       180       190       200       210       220       230
       |         |         |         |         |         |         |         |
AATAATAGTAATAGTAACGATGCGATGTCTTTTGTAAATGAAGTAATAAGGTTTATAGAAAACGAGAAGGATGATAAA
  N  N  S  N  S  N  D  A  M  S  F  V  N  E  V  I  R  F  I  E  N  E  K  D  D  K
  I  I  V  I  V  T  M  R  C  L  L  •  M  K  •  •  G  L  •  K  T  R  R  M  I  K
 •  •  •  •  •  R  C  D  V  F  C  K  •  S  N  K  V  Y  R  K  R  E  G  •  •  R 240       250       260       270       280       290       300       310
       |         |         |         |         |         |         |         |
GAAGATAAAAAAGTGAAGATAATATCTAGACCTGTTGAGAATACATTACATAGATATCCAGTTAGTTCTTTTCTGAAT
  E  D  K  K  V  K  I  I  S  R  P  V  E  N  T  L  H  R  Y  P  V  S  S  F  L  N
  K  I  K  K  •  R  •  Y  L  D  L  L  R  I  H  Y  I  D  I  Q  L  V  L  F  •  I
    R  •  K  S  E  D  N  I  •  T  C  •  E  Y  I  T  •  I  S  S  •  F  F  S  E  Y
```

FIGURE 2B (suite)

```
                320       330       340       350       360       370       380       390
                 |         |         |         |         |         |         |         |
          ATCAAAAAGTATGGTAGGAAAGGGGAATATTTGAATAGAAATAGTTTTGTTCAAAGATCATATATAAGGGGTTGTAAA
           I  K  K  Y  G  R  K  G  E  Y  L  N  R  N  S  F  V  Q  R  S  Y  I  R  G  C  K
          S  K  S  M  V  G  K  G  N  I  •  I  E  I  V  L  F  K  D  H  I  •  G  V  V  K
            Q  K  V  W  •  E  R  G  I  F  E  •  K  •  F  C  S  K  I  I  Y  K  G  L  •  R 400       410       420       430       440       450       460
                   |         |         |         |         |         |         |
           GGAAAAAGAAGCACACATACATGGATATGTGAAAATAAAGGGAATAATAATATATGTATTCCTGATAGACGTGTACAA
            G  K  R  S  T  H  T  W  I  C  E  N  K  G  N  N  N  I  C  I  P  D  R  R  V  Q
           E  K  E  A  H  I  H  G  Y  V  K  I  K  G  I  I  I  Y  V  F  L  I  D  V  Y  N
             K  K  K  H  T  Y  M  D  M  •  K  •  R  E  •  •  Y  M  Y  S  •  •  T  C  T  I 470       480       490       500       510       520       530       540
                   |         |         |         |         |         |         |         |
           TTATGTATAACAGCTCTTCAAGATTTAAAAAATTCAGGATCTGAAACGACTGATAGAAAATTATTAAGAGATAAAGTA
            L  C  I  T  A  L  Q  D  L  K  N  S  G  S  E  T  T  D  R  K  L  L  R  D  K  V
           Y  V  •  Q  L  F  K  I  •  K  I  Q  D  L  K  R  L  I  E  N  Y  •  E  I  K  Y
             M  Y  N  S  S  S  R  F  K  K  F  R  I  •  N  D  •  •  K  I  I  K  R  •  S  I 550       560       570       580       590       600       610       620
                   |         |         |         |         |         |         |         |
           TTTGATTCAGCTATGTATGAAACTGATTTGTTATGGAATAAATATGGTTTTCGTGGATTTGATGATTTTTGTGACGAT
            F  D  S  A  M  Y  E  T  D  L  L  W  N  K  Y  G  F  R  G  F  D  D  F  C  D  D
           L  I  Q  L  C  M  K  L  I  C  Y  G  I  N  M  V  F  V  D  L  M  I  F  V  T  M
             •  F  S  Y  V  •  N  •  F  V  M  E  •  I  W  F  S  W  I  •  •  F  L  •  R  C 630       640       650       660       670       680       690       700
                   |         |         |         |         |         |         |         |
           GTAAAAAATAGTTATTTAGATTATAAAGATGTTATATTTGGAACCGATTTAGATAAAAATAATATATCAAAGTTAGTA
            V  K  N  S  Y  L  D  Y  K  D  V  I  F  G  T  D  L  D  K  N  N  I  S  K  L  V
           •  K  I  V  I  •  I  I  K  M  L  Y  L  E  P  I  •  I  K  I  I  Y  Q  S  •  •
             K  K  •  L  F  R  L  •  R  C  Y  I  W  N  R  F  R  •  K  •  Y  I  K  V  S  R
```

FIGURE 2B (suite)

```
             710        720        730        740        750        760        770        780
              |          |          |          |          |          |          |          |
        GAGGAATCATTAAAACGTTTTTTTAAAAAAGATAGTAGTGTACTTAATCCTACTGCTTGGTGGAGAAGGTATGGAACA
          E  E  S  L  K  R  F  F  K  K  D  S  S  V  L  N  P  T  A  W  W  R  R  Y  G  T
           R  N  H  •  N  V  F  L  K  K  I  V  V  Y  L  I  L  L  L  G  G  E  G  M  E  Q
            G  I  I  K  T  F  F  •  K  R  •  •  C  T  •  S  Y  C  L  V  E  K  V  W  N  K 790        800        810        820        830        840        850
                   |          |          |          |          |          |          |
        AGACTATGGAAAACTATGATACAGCCATATGCTCATTTAGGATGTAGAAAACCTGATGAGAATGAACCTCAGATAAAT
          R  L  W  K  T  M  I  Q  P  Y  A  H  L  G  C  R  K  P  D  E  N  E  P  Q  I  N
           D  Y  G  K  L  •  Y  S  H  M  L  I  •  D  V  E  N  L  M  R  N  L  R  •  I
            T  M  E  N  Y  D  T  A  I  C  S  F  R  M  •  K  T  •  •  E  •  T  S  D  K  •

860        870        880        890        900        910        920        930
         |          |          |          |          |          |          |          |
        AGATGGATTCTGGAATGGGGGAAATATAATTGTAGATTAATGAAGGAGAAAGAAAAATTGTTAACAGGAGAATGTTCT
          R  W  I  L  E  W  G  K  Y  N  C  R  L  M  K  E  K  E  K  L  L  T  G  E  C  S
           D  G  F  W  N  G  G  N  I  I  V  D  •  •  R  R  K  K  N  C  •  Q  E  N  V  L
            M  D  S  G  M  G  E  I  •  L  •  I  N  E  G  E  R  K  I  V  N  R  R  M  F  C 940        950        960        970        980        990       1000       1010
             |          |          |          |          |          |          |          |
        GTTAATAGAAAAAAATCTGACTGCTCAACCGGATGTAATAATGAGTGTTATACCTATAGGAGTCTTATTAATAGACAA
          V  N  R  K  K  S  D  C  S  T  G  C  N  N  E  C  Y  T  Y  R  S  L  I  N  R  Q
           L  I  E  K  N  L  T  A  Q  P  D  V  I  M  S  V  I  P  I  G  V  L  L  I  D  K
            •  •  K  K  I  •  L  L  N  R  M  •  •  •  V  L  Y  L  •  E  S  Y  •  •  T  K 1020       1030       1040       1050       1060       1070       1080       1090
                   |          |          |          |          |          |          |          |
        AGATATGAGGTCTCTATATTAGGAAAAAAATATATTAAAGTAGTACGATATACTATATTTAGGAGAAAAATAGTTCAA
          R  Y  E  V  S  I  L  G  K  K  Y  I  K  V  V  R  Y  T  I  F  R  R  K  I  V  Q
           D  M  R  S  L  Y  •  E  K  N  I  L  K  •  Y  D  I  L  Y  L  G  E  K  •  F  N
            I  •  G  L  Y  I  R  K  K  I  Y  •  S  S  T  I  Y  Y  I  •  E  K  N  S  S  T
```

FIGURE 2B (suite)

```
           1100      1110      1120      1130      1140      1150      1160      1170
            |         |         |         |         |         |         |         |
       CCTGATAATGCTTTGGATTTTTTAAAATTAAATTGTTCTGAGTGTAAGGATATTGATTTTAAACCCTTTTTTGAATTT
        P  D  N  A  L  D  F  L  K  L  N  C  S  E  C  K  D  I  D  F  K  P  F  F  E  F
         L  I  M  L  W  I  F  •  N  •  I  V  L  S  V  R  I  L  I  L  N  P  F  L  N  L
           •  •  C  F  G  F  F  K  I  K  L  F  •  V  •  G  Y  •  F  •  T  L  F  •  I  •

1180      1190      1200      1210      1220      1230      1240
            |         |         |         |         |         |         |
       GAATATGGTAAATATGAAGAAAAATGTATGTGTCAATCATATATTGATTTAAAAATCCAATTTAAAAATAATGATATT
        E  Y  G  K  Y  E  E  K  C  M  C  Q  S  Y  I  D  L  K  I  Q  F  K  N  N  D  I
         N  M  V  N  M  K  K  N  V  C  V  N  H  I  L  I  •  K  S  N  L  K  I  M  I  F
           I  W  •  I  •  R  K  M  Y  V  S  I  I  Y  •  F  K  N  P  I  •  K  •  •  Y  L 1250      1260      1270      1280      1290      1300      1310      1320
         |         |         |         |         |         |         |         |
       TGTTCATTTAATGCTCAAACAGATACTGTTTCTAGCGATAAAAGATTTTGTCTTGAAAAGAAAGAATTTAAACCATGG
        C  S  F  N  A  Q  T  D  T  V  S  S  D  K  R  F  C  L  E  K  K  E  F  K  P  W
         V  H  L  M  L  K  Q  I  L  F  L  A  I  K  D  F  V  L  K  R  K  N  L  N  H  G
           F  I  •  C  S  N  R  Y  C  F  •  R  •  K  I  L  S  •  K  E  R  I  •  T  M  E 1330      1340      1350      1360      1370      1380      1390      1400
         |         |         |         |         |         |         |         |
       AAATGTGATAAAAATTCTTTTGAAACAGTTCATCATAAAGGTGTATGTGTGTCACCGAGAAGACAAGGTTTTTGTTTA
        K  C  D  K  N  S  F  E  T  V  H  H  K  G  V  C  V  S  P  R  R  Q  G  F  C  L
         N  V  I  K  I  L  L  K  Q  F  I  I  K  V  Y  V  C  H  R  E  D  K  V  F  V  •
           M  •  •  K  F  F  •  N  S  S  S  •  R  C  M  C  V  T  E  K  T  R  F  L  F  R 1410      1420      1430      1440      1450      1460      1470      1480
         |         |         |         |         |         |         |         |
       GGAAATTTGAACTATCTACTGAATGATGATATTTATAATGTACATAATTCACAACTACTTATCGAAATTATAATGGCT
        G  N  L  N  Y  L  L  N  D  D  I  Y  N  V  H  N  S  Q  L  L  I  E  I  I  M  A
         E  I  •  T  I  Y  •  M  M  I  F  I  M  Y  I  I  H  N  Y  L  S  K  L  •  W  L
           K  F  E  L  S  T  E  •  •  Y  L  •  C  T  •  F  T  T  T  Y  R  N  Y  N  G  F
```

FIGURE 2B (suite)

```
         1490      1500      1510      1520      1530      1540      1550      1560
           |         |         |         |         |         |         |         |
TCTAAACAAGAAGGAAAGTTATTATGGAAAAAACATGGAACAATACTTGATAACCAGAATGCATGCAAATATATAAAT
 S  K  Q  E  G  K  L  L  W  K  K  H  G  T  I  L  D  N  Q  N  A  C  K  Y  I  N
  L  N  K  K  E  S  Y  Y  G  K  N  M  E  Q  Y  L  I  T  R  M  H  A  N  I  •  M
   •  T  R  R  K  V  I  M  E  K  T  W  N  N  T  •  •  P  E  C  M  Q  I  Y  K  •

1570      1580      1590      1600      1610      1620      1630
           |         |         |         |         |         |         |
GATAGTTATGTTGATTATAAAGATATAGTTATTGGAAATGATTTATGGAATGATAACAACTCTATAAAAGTTCAAAAT
 D  S  Y  V  D  Y  K  D  I  V  I  G  N  D  L  W  N  D  N  N  S  I  K  V  Q  N
  I  V  M  L  I  I  K  I  •  L  L  E  M  I  Y  G  M  I  T  T  L  •  K  F  K  I
   •  L  C  •  L  •  R  Y  S  Y  W  K  •  F  M  E  •  •  Q  L  Y  K  S  S  K  •

1640      1650      1660      1670      1680      1690      1700      1710
           |         |         |         |         |         |         |         |
AATTTAAATTTAATTTTTGAAAGAAATTTTGGTTATAAAGTTGGAAGAAATAAACTCTTTAAAACAATTAAAGAATTA
 N  L  N  L  I  F  E  R  N  F  G  Y  K  V  G  R  N  K  L  F  K  T  I  K  E  L
  I  •  I  •  F  L  K  E  I  L  V  I  K  L  E  E  I  N  S  L  K  Q  L  K  N  •
   F  K  F  N  F  •  K  K  F  W  L  •  S  W  K  K  •  T  L  •  N  N  •  R  I  K 1720      1730      1740      1750      1760      1770      1780      1790
           |         |         |         |         |         |         |         |
AAAAATGTATGGTGGATATATTAAATAGAAATAAAGTATGGGAATCAATGAGATGTGGAATTGACGAAGTAGATCAACGT
 K  N  V  W  W  I  L  N  R  N  K  V  W  E  S  M  R  C  G  I  D  E  V  D  Q  R
  K  M  Y  G  G  Y  •  I  E  I  K  Y  G  N  Q  •  D  V  E  L  T  K  •  I  N  V
   K  C  M  V  D  I  K  •  K  •  S  M  G  I  N  E  M  W  N  •  R  S  R  S  T  •

1800      1810      1820      1830      1840      1850      1860      1870
           |         |         |         |         |         |         |         |
AGAAAAACTTGTGAAAGAATAGATGAACTAGAAAACATGCCACAATTCTTTAGATGGTTTTCACAATGGGCACATTTC
 R  K  T  C  E  R  I  D  E  L  E  N  M  P  Q  F  F  R  W  F  S  Q  W  A  H  F
  E  K  L  V  K  E  •  M  N  •  K  T  C  H  N  S  L  D  G  F  H  N  G  H  I  S
   K  N  L  •  K  N  R  •  T  R  K  H  A  T  I  L  •  M  V  F  T  M  G  T  F  L
```

FIGURE 2B (suite)

```
         1880       1890       1900       1910       1920       1930       1940       1950
          |          |          |          |          |          |          |          |
TTTTGTAAGGAAAAAGAATATTGGGAATTAAAATTAAATGATAAATGTACAGGTAATAATGGAAAATCCTTATGTCAG
 F  C  K  E  K  E  Y  W  E  L  K  L  N  D  K  C  T  G  N  N  G  K  S  L  C  Q
   F  V  R  K  K  N  I  G  N  •  N  •  M  I  N  V  Q  V  I  M  E  N  P  Y  V  R
     L  •  G  K  R  I  L  G  I  K  I  K  •  •  M  Y  R  •  •  W  K  I  L  M  S  G 1960       1970       1980       1990       2000       2010       2020
          |          |          |          |          |          |          |
GATAAAACATGTCAAAATGTGTGTACTAATATGAATTATTGGACATATACTAGAAAATTAGCTTATGAAATACAATCC
 D  K  T  C  Q  N  V  C  T  N  M  N  Y  W  T  Y  T  R  K  L  A  Y  E  I  Q  S
   I  K  H  V  K  M  C  V  L  I  •  I  I  G  H  I  L  E  N  •  L  M  K  Y  N  P
     •  N  M  S  K  C  V  Y  •  Y  E  L  L  D  I  Y  •  K  I  S  L  •  N  T  I  R 2030       2040       2050       2060       2070       2080       2090       2100
          |          |          |          |          |          |          |          |
GTAAAATATGATAAAGATAGAAAATTATTTAGTCTTGCTAAAGACAAAAATGTAACTACATTTTTAAAGGAAAATGCA
 V  K  Y  D  K  D  R  K  L  F  S  L  A  K  D  K  N  V  T  T  F  L  K  E  N  A
   •  N  M  I  K  I  E  N  Y  L  V  L  L  K  T  K  M  •  L  H  F  •  R  K  M  Q
     K  I  •  •  R  •  K  I  I  •  S  C  •  R  Q  K  C  N  Y  I  F  K  G  K  C  K 2110       2120       2130       2140       2150       2160       2170       2180
          |          |          |          |          |          |          |          |
AAAAATTGTTCTAATATAGATTTTACAAAAATATTCGATCAGCTTGACAAACTCTTTAAGGAAAGATGTTCATGTATG
 K  N  C  S  N  I  D  F  T  K  I  F  D  Q  L  D  K  L  F  K  E  R  C  S  C  M
   K  I  V  L  I  •  I  L  Q  K  Y  S  I  S  L  T  N  S  L  R  K  D  V  H  V  W
     K  L  F  •  Y  R  F  Y  K  N  I  R  S  A  •  Q  T  L  •  G  K  M  F  M  Y  G 2190       2200       2210       2220       2230       2240       2250       2260
          |          |          |          |          |          |          |          |
GATACACAAGTTTTAGAAGTAAAAAACAAAGAAATGTTATCTATAGACTCAAATAGTGAAGATGCGACAGATATAAGT
 D  T  Q  V  L  E  V  K  N  K  E  M  L  S  I  D  S  N  S  E  D  A  T  D  I  S
   I  H  K  F  •  K  •  K  T  K  K  C  Y  L  •  T  Q  I  V  K  M  R  Q  I  •  V
     Y  T  S  F  R  S  K  K  Q  R  N  V  I  Y  R  L  K  •  •  R  C  D  R  Y  K  •
```

FIGURE 2B (suite)

```
         2270      2280      2290      2300      2310      2320      2330      2340
          |         |         |         |         |         |         |         |
GAGAAAAATGGAGAGGAAGAATTATATGTAAATCACAATTCTGTGAGTGTCGCAAGTGGTAATAAAGAAATCGAAAAG
 E  K  N  G  E  E  E  L  Y  V  N  H  N  S  V  S  V  A  S  G  N  K  E  I  E  K
  R  K  M  E  R  K  N  Y  M  •  I  T  I  L  •  V  S  Q  V  V  I  K  K  S  K  R
   E  K  W  R  G  R  I  I  C  K  S  Q  F  C  E  C  R  K  W  •  •  R  N  R  K  E 2350      2360      2370      2380      2390      2400      2410
          |         |         |         |         |         |         |
AGTAAGGATGAAAAGCAACCTGAAAAAGAAGCAAAACAAACTAATGGAACTTTAACCGTACGAACTGACAAAGATTCA
 S  K  D  E  K  Q  P  E  K  E  A  K  Q  T  N  G  T  L  T  V  R  T  D  K  D  S
  V  R  M  K  S  N  L  K  K  K  Q  N  K  L  M  E  L  •  P  Y  E  L  T  K  I  Q
   •  G  •  K  A  T  •  K  R  S  K  T  N  •  W  N  F  N  R  T  N  •  Q  R  F  R 2420      2430      2440      2450      2460      2470      2480      2490
          |         |         |         |         |         |         |         |
GATAGAAACAAAGGAAAAGATACAGCTACTGATACAAAAAATTCACCTGAAAATTTAAAAGTACAGGAACATGGAACA
 D  R  N  K  G  K  D  T  A  T  D  T  K  N  S  P  E  N  L  K  V  Q  E  H  G  T
  I  E  T  K  E  K  I  Q  L  L  I  Q  K  I  H  L  K  I  •  K  Y  R  N  M  E  Q
   •  K  Q  R  K  R  Y  S  Y  •  Y  K  K  F  T  •  K  F  K  S  T  G  T  W  N  K 2500      2510      2520      2530      2540      2550      2560      2570
          |         |         |         |         |         |         |         |
AATGGAGAAACAATAAAAGAAGAACCACCAAAATTACCTGAATCATCTGAAACATTACAATCACAAGAACAATTAGAA
 N  G  E  T  I  K  E  E  P  P  K  L  P  E  S  S  E  T  L  Q  S  Q  E  Q  L  E
  M  E  K  Q  •  K  K  N  H  Q  N  Y  L  N  H  L  K  H  Y  N  H  K  N  N  •  K
   W  R  N  N  K  R  R  T  T  K  I  T  •  I  I  •  N  I  T  I  T  R  T  I  R  S 2580      2590      2600      2610      2620      2630      2640      2650
          |         |         |         |         |         |         |         |
GCAGAAGCACAAAAACAAAAACAAGAAGAAGAACCAAAAAAAAAACAAGAAGAAGAACCAAAAAAAAAAACAAGAAGAA
 A  E  A  Q  K  Q  K  Q  E  E  E  P  K  K  K  Q  E  E  E  P  K  K  K  Q  E  E
  Q  K  H  K  N  K  N  K  K  K  N  Q  K  K  N  K  K  K  N  Q  K  K  N  K  K  K
   R  S  T  K  T  K  T  R  R  R  T  K  K  K  T  R  R  R  T  K  K  K  T  R  R  R
```

FIGURE 2B (suite)

```
            2660       2670       2680       2690       2700       2710       2720       2730
              |          |          |          |          |          |          |          |
       GAACAAAAACGAGAACAAGAACAAAAACAAGAACAAGAAGAAGAAGAACAAAAACAAGAAGAAGAACAACAAATACAA
        E   Q   K   R   E   Q   E   Q   K   Q   E   Q   E   E   E   Q   K   Q   E   E   E   Q   Q   I   Q
         N   K   N   E   N   K   N   K   N   K   K   K   K   N   K   N   K   K   K   N   N   K   Y   K
          T   K   T   R   T   R   T   K   T   R   T   R   R   R   R   T   K   T   R   R   R   T   T   N   T   R 2740       2750       2760       2770       2780       2790       2800
              |          |          |          |          |          |          |
       GATCAATCACAAAGTGGATTAGATCAATCCTCAAAAGTAGGAGTAGCGAGTGAACAAAATGAAATTTCTTCAGGACAA
        D   Q   S   Q   S   G   L   D   Q   S   S   K   V   G   V   A   S   E   Q   N   E   I   S   S   G   Q
         I   N   H   K   V   D   *   I   N   P   Q   K   *   E   *   R   V   N   K   M   K   F   L   Q   D   K
          S   I   T   K   W   I   R   S   I   L   K   S   R   S   S   E   *   T   K   *   N   F   F   R   T   R 2810       2820       2830       2840       2850       2860       2870       2880
              |          |          |          |          |          |          |          |
       GAACAAAACGTAAAAAGCTCTTCACCTGAAGTAGTTCCACAAGAAACAACTAGTGAAAATGGGTCATCACAAGACACA
        E   Q   N   V   K   S   S   S   P   E   V   V   P   Q   E   T   T   S   E   N   G   S   S   Q   D   T
         N   K   T   *   K   A   L   H   L   K   *   F   H   K   K   Q   L   V   K   M   G   H   H   K   T   Q
          T   K   R   K   K   L   F   T   *   S   S   S   T   R   N   N   *   *   K   W   V   I   T   R   H   K 2890       2900       2910       2920       2930       2940       2950       2960
              |          |          |          |          |          |          |          |
       AAAATATCAAGTACTGAACCAAATGAGAATTCTGTTGTAGATAGAGCAACAGATAGTATGAATTTAGATCCTGAAAAG
        K   I   S   S   T   E   P   N   E   N   S   V   V   D   R   A   T   D   S   M   N   L   D   P   E   K
         K   Y   Q   V   L   N   Q   M   R   I   L   L   *   I   E   Q   Q   I   V   *   I   *   I   L   K   R
          N   I   K   Y   *   T   K   *   E   F   C   C   R   *   S   N   R   *   Y   E   F   R   S   *   K   G 2970       2980       2990       3000       3010       3020       3030       3040
              |          |          |          |          |          |          |          |
       GTTCATAATGAAAATATGAGTGATCCAAATACAAATACTGAACCAGATGCATCTTTAAAAGATGATAAGAAGGAAGTT
        V   H   N   E   N   M   S   D   P   N   T   N   T   E   P   D   A   S   L   K   D   D   K   K   E   V
         F   I   M   K   I   *   V   I   Q   I   Q   I   L   N   Q   M   H   L   *   K   M   I   R   R   K   L
          S   *   *   K   Y   E   *   S   K   Y   K   Y   *   T   R   C   I   F   K   R   *   *   E   G   S   *
```

FIGURE 2B (suite)

```
              3050      3060      3070      3080      3090      3100      3110      3120
               |         |         |         |         |         |         |         |
          GATGATGCCAAAAAAGAACTTCAATCTACTGTATCAAGAATTGAATCTAATGAACAGGACGTTCAAAGTACACCACCC
           D  D  A  K  K  E  L  Q  S  T  V  S  R  I  E  S  N  E  Q  D  V  Q  S  T  P  P
            M  M  P  K  K  N  F  N  L  L  Y  Q  E  L  N  L  M  N  R  T  F  K  V  H  H  P
             •  C  Q  K  R  T  S  I  Y  C  I  K  N  •  I  •  •  T  G  R  S  K  Y  T  T  R 3130      3140      3150      3160      3170      3180      3190
                         |         |         |         |         |         |         |
          GAAGATACTCCTACTGTTGAAGGAAAAGTAGGAGATAAAGCAGAAATGTTAACTTCTCCGCATGCGACAGATAATTCT
           E  D  T  P  T  V  E  G  K  V  G  D  K  A  E  M  L  T  S  P  H  A  T  D  N  S
            K  I  L  L  L  K  E  K  •  E  I  K  Q  K  C  •  L  L  R  M  R  Q  I  I  L
             R  Y  S  Y  C  •  R  K  S  R  R  •  S  R  N  V  N  F  S  A  C  D  R  •  F  •

3200      3210      3220      3230      3240      3250      3260      3270
               |         |         |         |         |         |         |         |
          GAGTCGGAATCAGGTTTAAATCCAACTGATGACATTAAAACAACTGATGGTGTTGTTAAAGAACAAGAAATATTAGGG
           E  S  E  S  G  L  N  P  T  D  D  I  K  T  T  D  G  V  V  K  E  Q  E  I  L  G
            S  R  N  Q  V  •  I  Q  L  M  T  L  K  Q  L  M  V  L  L  K  N  K  K  Y  •  G
             V  G  I  R  F  K  S  N  •  •  H  •  N  N  •  W  C  C  •  R  T  R  N  I  R  G 3280      3290      3300      3310      3320      3330      3340      3350
               |         |         |         |         |         |         |         |
          GGAGGTGAAAGTGCAACTGAAACATCAAAAAGTAATTTAGAAAAACCTAAGGATGTTGAACCTTCTCATGAAATATCT
           G  G  E  S  A  T  E  T  S  K  S  N  L  E  K  P  K  D  V  E  P  S  H  E  I  S
            E  V  K  V  Q  L  K  H  Q  K  V  I  •  K  N  L  R  M  L  N  L  L  M  K  Y  L
             R  •  K  C  N  •  N  I  K  K  •  F  R  K  T  •  G  C  •  T  F  S  •  N  I  •

3360      3370      3380      3390      3400      3410      3420      3430
               |         |         |         |         |         |         |         |
          GAACCTGTTCTTTCTGGTACAACTGGTAAAGAAGAATCAGAGTTATTAAAAAGTAAATCGATAGAGACGAAGGGGGAA
           E  P  V  L  S  G  T  T  G  K  E  E  S  E  L  L  K  S  K  S  I  E  T  K  G  E
            N  L  F  F  L  V  Q  L  V  K  K  N  Q  S  Y  •  K  V  N  R  •  R  R  R  G  K
             T  C  S  F  W  Y  N  W  •  R  R  I  R  V  I  K  K  •  I  D  R  D  E  G  G  N
```

FIGURE 2B (suite)

```
         3440      3450      3460      3470      3480      3490      3500      3510
ACAGATCCTCGAAGTAATGACCAAGAAGATGCTACTGACGATGTTGTAGAAAATAGTAGAGATGATAATAATAGTCTC
 T  D  P  R  S  N  D  Q  E  D  A  T  D  D  V  V  E  N  S  R  D  D  N  N  S  L
  Q  I  L  E  V  M  T  K  K  M  L  L  T  M  L  *  K  I  V  E  M  I  I  I  V  S
   R  S  S  K  *  *  P  R  R  C  Y  *  R  C  C  R  K  *  *  R  *  *  *  *  S  L 3520      3530      3540      3550      3560      3570      3580
TCTAATAGCGTAGATAATCAAAGTAATGTTTTAAATAGAGAAGATCCTATTGCTTCTGAAACTGAAGTTGTAAGTGAA
 S  N  S  V  D  N  Q  S  N  V  L  N  R  E  D  P  I  A  S  E  T  E  V  V  S  E
  L  I  A  *  I  I  K  V  M  F  *  I  E  K  I  L  L  L  K  L  K  L  *  V  N
   *  *  R  R  *  S  K  *  C  F  K  *  R  R  S  Y  C  F  *  N  *  S  C  K  *  T 3590      3600      3610      3620      3630      3640      3650      3660
                      G
CCTGAGGATTCAAGTAGGATAATCACTACAGAAGTTCCAAGTACTACTGTAAAACCCCCTGATGAAAAACGATCTGAA
 P  E  D  S  S  R  I  M  T  T  E  V  P  S  T  T  V  K  P  P  D  E  K  R  S  E
  L  R  I  Q  V  G  *  S  L  Q  K  F  Q  V  L  L  *  N  P  L  M  K  N  D  L  K
   *  G  F  K  *  D  N  H  Y  R  S  S  K  Y  Y  C  K  T  P  *  *  K  T  I  *  R 3670      3680      3690      3700      3710      3720       3730      3740
GAAGTAGGAGAAAAAGAAGCTAAAGAAATTAAAGTAGAACCTGTTGTACCAAGAGCCATTGGAGAACCAATGGAAAAT
 E  V  G  E  K  E  A  K  E  I  K  V  E  P  V  V  P  R  A  I  G  E  P  M  E  N
  K  *  E  K  K  K  L  K  K  L  K  *  N  L  L  Y  Q  E  P  L  E  N  Q  W  K  I
   S  R  R  K  R  S  *  R  N  *  S  R  T  C  C  T  K  S  H  W  R  T  N  G  K  F 3750      3760       3770      3780      3790      3800      3810      3820
TCTGTGAGCGTACAGTCCCCTCCTAATGTAGAAGATGTTGAAAAAGAAACATTGATATCTGAGAATAATGGATTACAT
 S  V  S  V  Q  S  P  P  N  V  E  D  V  E  K  E  T  L  I  S  E  N  N  G  L  H
  L  *  A  Y  S  P  L  L  M  *  K  M  L  K  K  K  H  *  Y  L  R  I  M  D  Y  I
   C  E  R  T  V  P  S  *  C  R  R  C  *  K  R  N  I  D  I  *  E  *  W  I  T  *
```

FIGURE 2B (suite)

```
              3830      3840      3850      3860      3870      3880      3890      3900
               |         |         |         |         |         |         |         |
         AATGATACACACAGAGGAAATATCAGTGAAAAGGATTTAATCGATATTCATTTGTTAAGAAATGAAGCGGGTAGTACA
          N  D  T  H  R  G  N  I  S  E  K  D  L  I  D  I  H  L  L  R  N  E  A  G  S  T
           M  I  H  T  E  E  I  S  V  K  R  I  •  S  I  F  I  C  •  E  M  K  R  V  V  Q
            •  Y  T  Q  R  K  Y  Q  •  K  G  F  N  R  Y  S  F  V  K  K  •  S  G  •  Y  N 3910      3920      3930      3940      3950      3960      3970
                     |         |         |         |         |         |         |
         ATATTAGATGATTCTAGAAGAAATGGAGAAATGACAGAAGGTAGCGAAAGTGATGTTGGAGAATTACAAGAACATAAT
          I  L  D  D  S  R  R  N  G  E  M  T  E  G  S  E  S  D  V  G  E  L  Q  E  H  N
           Y  •  M  I  L  E  E  M  E  K  •  Q  K  V  A  K  V  M  L  E  N  Y  K  N  I  I
            I  R  •  F  •  K  K  W  R  N  D  R  R  •  R  K  •  C  W  R  I  T  R  T  •  F 3980      3990      4000      4010      4020      4030      4040      4050
               |         |         |         |         |         |         |         |
         TTTAGCACACAACAAAAAGATGAAAAAGATTTTGACCAAATTGCGAGCGATAGAGAAAAAGAAGAAATTCAAAAATTA
          F  S  T  Q  Q  K  D  E  K  D  F  D  Q  I  A  S  D  R  E  K  E  E  I  Q  K  L
           L  A  H  N  K  K  M  K  K  I  L  T  K  L  R  A  I  E  K  K  K  K  F  K  N  Y
            •  H  T  T  K  R  •  K  R  F  •  P  N  C  E  R  •  R  K  R  R  N  S  K  I  T 4060      4070      4080      4090      4100      4110      4120      4130
               |         |         |         |         |         |         |         |
         CTTAATATAGGACATGAAGAGGATGAAGATGTATTAAAAATGGATAGAACAGAGGATAGTATGAGTGATGGAGTTAAT
          L  N  I  G  H  E  E  D  E  D  V  L  K  M  D  R  T  E  D  S  M  S  D  G  V  N
           L  I  •  D  M  K  R  M  K  M  Y  •  K  W  I  E  Q  R  I  V  •  V  M  E  L  I
            •  Y  R  T  •  R  G  •  R  C  I  K  N  G  •  N  R  G  •  Y  E  •  W  S  •  •

4140      4150      4160      4170      4180      4190      4200      4210
               |         |         |         |         |         |         |         |
         AGTCATTTGTATTATAATAATCTATCAAGTGAAGAAAAAATGGAACAATATAATAATAGAGATGCTTCTAAAGATAGA
          S  H  L  Y  Y  N  N  L  S  S  E  E  K  M  E  Q  Y  N  N  R  D  A  S  K  D  R
           V  I  C  I  I  I  I  Y  Q  V  K  K  K  W  N  N  I  I  I  E  M  L  L  K  I  E
            S  F  V  L  •  •  S  I  K  •  R  K  N  G  T  I  •  •  •  R  C  F  •  R  •  R
```

FIGURE 2B (suite)

```
              4220       4230       4240       4250       4260       4270       4280       4290
                |          |          |          |          |          |          |          |
        GAAGAAATATTGAATAGGTCAAACACAAATACATGTTCTAATGAACATTCATTAAAATATTGTCAATATATGGAAAGA
         E  E  I  L  N  R  S  N  T  N  T  C  S  N  E  H  S  L  K  Y  C  Q  Y  M  E  R
          K  K  Y  *  I  G  Q  T  Q  I  H  V  L  M  N  I  H  *  N  I  V  N  I  W  K  E
           R  N  I  E  *  V  K  H  K  Y  M  F  *  *  T  F  I  K  I  L  S  I  Y  G  K  K 4300       4310       4320       4330       4340       4350       4360
                |          |          |          |          |          |          |
        AATAAGGATTTATTAGAAACATGTTCTGAAGACAAAAGGTTACATTTATGTTGTGAAATATCAGATTATTGTTTAAAA
         N  K  D  L  L  E  T  C  S  E  D  K  R  L  H  L  C  C  E  I  S  D  Y  C  L  K
          I  R  I  Y  *  K  H  V  L  K  T  K  G  Y  I  Y  V  V  K  Y  Q  I  I  V  *  N
           *  G  F  I  R  N  M  F  *  R  Q  K  V  T  F  M  L  *  N  I  R  L  L  F  K  I 4370       4380       4390       4400       4410       4420       4430       4440
                |          |          |          |          |          |          |          |
        TTTTTCAATCCTAAATCGATAGAATACTTTGATTGTACACAAAAAGAATTTGATGACCCTACATATAATTGTTTTAGA
         F  F  N  P  K  S  I  E  Y  F  D  C  T  Q  K  E  F  D  D  P  T  Y  N  C  F  R
          F  S  I  L  N  R  *  N  T  L  I  V  H  K  K  N  L  M  T  L  H  I  I  V  L  E
           F  Q  S  *  I  D  R  I  L  *  L  Y  T  K  R  I  *  *  P  Y  I  *  L  F  *  K 4450       4460       4470       4480       4490       4500       4510       4520
                |          |          |          |          |          |          |          |
        AAACAAAGATTTACAAGTATGTCATGTTATAAAATTAAAAACAATATACATTAATATGTTAATAAAAAAAATAATATA
         K  Q  R  F  T  S  M  S  C  Y  K  I  K  N  N  I  H  *  Y  V  N  K  K  N  N  I
          N  K  D  L  Q  V  C  H  V  I  K  L  K  T  I  Y  I  N  M  L  I  K  K  I  I  Y
           T  K  I  Y  K  Y  V  M  L  *  N  *  K  Q  Y  T  L  I  C  *  *  K  K  *  Y  I 4530       4540       4550       4560       4570       4580       4590       4600
                |          |          |          |          |          |          |          |
        TTTTTTTCTCTTTTTCTTTTTTTTTTAATAGGTATGCATTATATTGCCGGGGGTGGTATAATAGCCCTTTTATTGTTTA
         F  F  S  L  F  L  F  F  *  *  V  C  I  I  L  P  G  V  V  *  *  P  F  Y  C  L
          F  F  L  F  F  F  F  F  N  R  Y  A  L  Y  C  R  G  W  Y  N  S  P  F  I  V  Y
           F  F  S  F  S  F  F  L  I  G  M  H  Y  I  A  G  G  G  I  I  A  L  L  L  F  I
```

FIGURE 2B (suite)

```
          4610      4620      4630      4640      4650      4660      4670      4680
            |         |         |         |         |         |         |         |
TTTTAGGTTCAGCCAGCTATAGGAAGAATTTGTAAGAAAAAAAGGATGAAGAAATATAAACAAAAATATAAATATATG
 F  •  V  Q  P  A  I  G  R  I  C  K  K  K  R  M  K  K  Y  K  Q  K  Y  K  Y  M
  F  R  F  S  Q  L  •  E  E  F  V  R  K  K  G  •  R  N  I  N  K  N  I  N  I  C
   L  G  S  A  S  Y  R  K  N  L  •  E  K  K  D  E  E  I  •  T  K  I  •  I  Y  A 4690      4700      4710      4720      4730      4740      4750
              |         |         |         |         |         |         |
CATATATATTTAAGTATTATAAGAACATATATATAAATAAATATGTATATTTTTATTTTATTATTATAGGGATGATGA
 H  I  Y  L  S  I  I  R  T  Y  I  •  I  N  M  Y  I  F  I  L  L  L  •  G  •  •
  I  Y  I  •  V  L  •  E  H  I  Y  K  •  I  C  I  F  L  F  Y  Y  Y  R  D  D  E
   Y  I  F  K  Y  Y  K  N  I  Y  I  N  K  Y  V  Y  F  Y  F  I  I  I  G  M  M  K 4760      4770      4780      4790      4800      4810      4820      4830
            |         |         |         |         |         |         |         |
AAAAGGATTCTACGATTCTAATTTAAATGATTCTGCTTTTGAATATAATAATAATAAATATAATAAATTACCTTATAT
 K  R  I  L  R  F  •  F  K  •  F  C  F  •  I  •  •  •  •  I  •  •  I  T  L  Y
  K  G  F  Y  D  S  N  L  N  D  S  A  F  E  Y  N  N  N  K  Y  N  K  L  P  Y  M
   K  D  S  T  I  L  I  •  M  I  L  L  L  N  I  I  I  I  N  I  I  N  Y  L  I  C 4840      4850      4860      4870      4880      4890      4900      4910
            |         |         |         |         |         |         |         |
GTGTAAGGAAAAAACTAAAAAACAAAAAAAAAAAAAAATATATATATATATATATATATTTACGGATGCATTTCCACA
 V  •  G  K  N  •  K  T  K  K  K  K  N  I  Y  I  Y  I  Y  I  Y  G  C  I  S  T
  C  K  E  K  T  K  K  Q  K  K  K  K  K  I  Y  I  Y  I  Y  I  F  T  D  A  F  P  H
   V  R  K  K  L  K  N  K  K  K  K  K  K  Y  I  Y  I  Y  I  Y  L  R  M  H  F  H  I 4920      4930      4940      4950      4960      4970      4980      4990
            |         |         |         |         |         |         |         |
TTCCTATTATTTCTTATTCTTATAATTTTTATTATTTATTTATTTATTTTTTTTTTCGTAGTTGATCAACAAATAAA
 F  L  L  F  L  I  L  I  I  F  I  I  Y  L  F  I  F  F  F  R  S  •  S  T  N  K
  S  Y  Y  F  L  F  L  •  F  L  L  F  I  Y  L  F  F  F  F  V  V  D  Q  Q  I  N
   P  I  I  S  Y  S  Y  N  F  Y  Y  L  F  I  Y  F  F  F  S  •  L  I  N  K  •  M
```

FIGURE 2B (suite)

```
        5000      5010      5020      5030      5040      5050
          |         |         |         |         |         |
TGTAGTAAATTCTGATTTATATTCGGAGGGTATTTATGATGACAACGACATTTTAA
  C  S  K  F  *  F  I  F  G  G  Y  L  *  *
   V  V  N  S  D  L  Y  S  E  G  I  Y  D  D  T  T  T  F  *
     *  *  I  L  I  Y  I  R  R  V  F  M  M
```

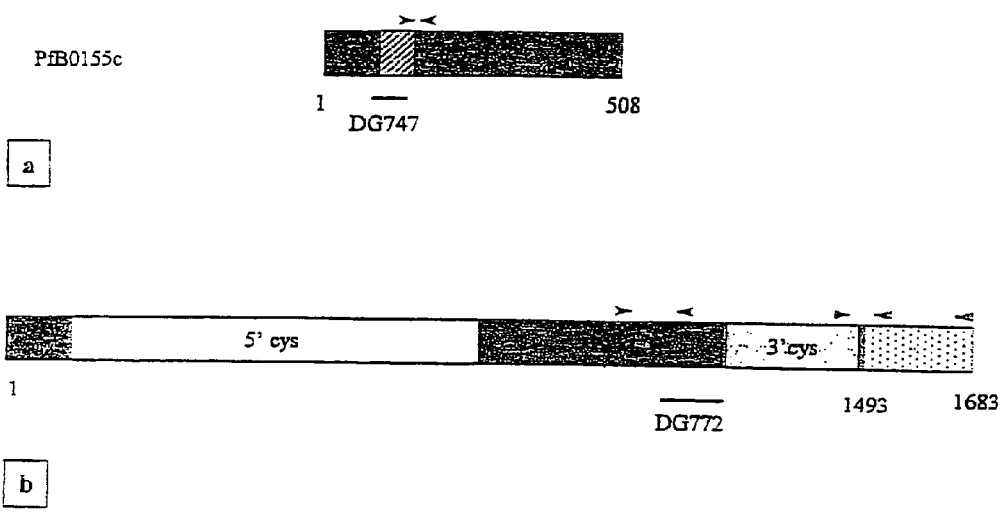
Figure 3.1

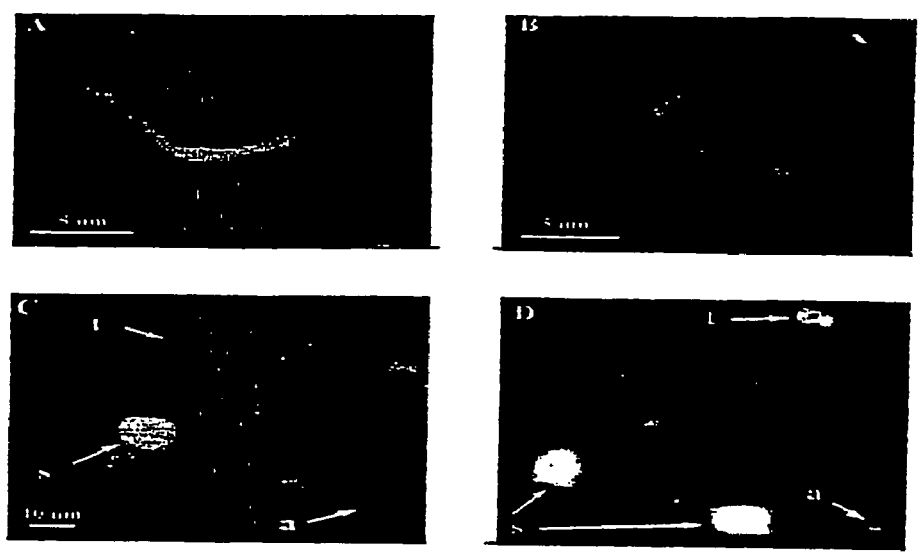
Figure 3.2

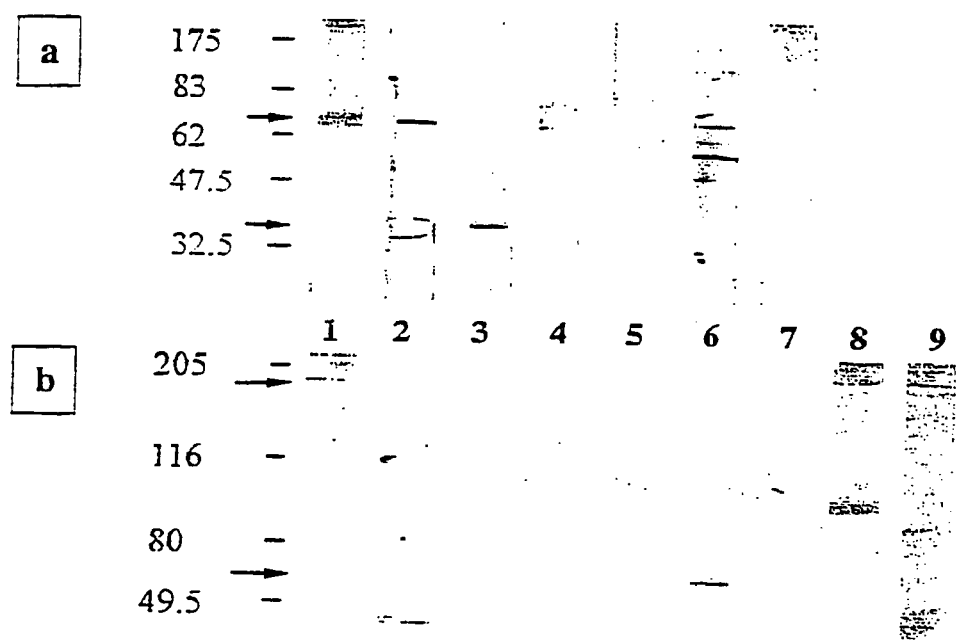
Figure 3.3

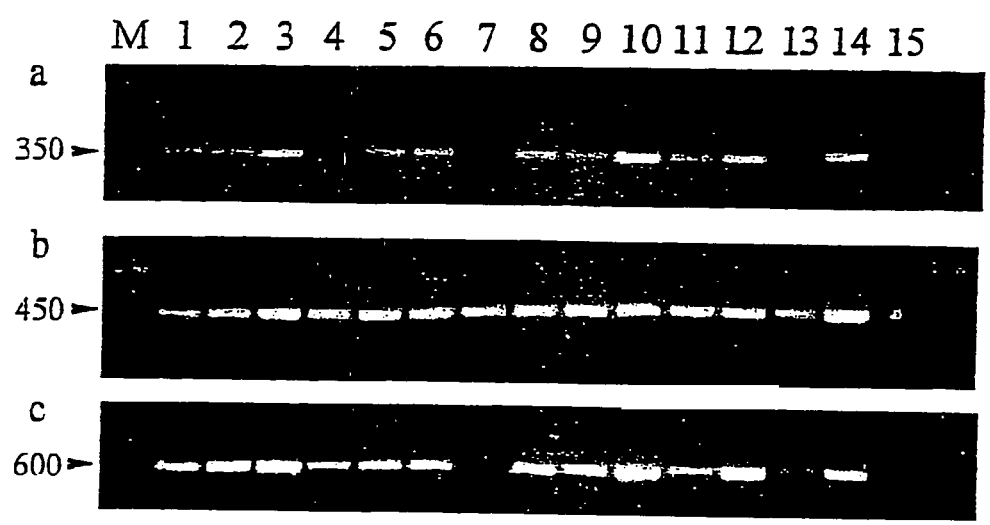
Figure 3.4

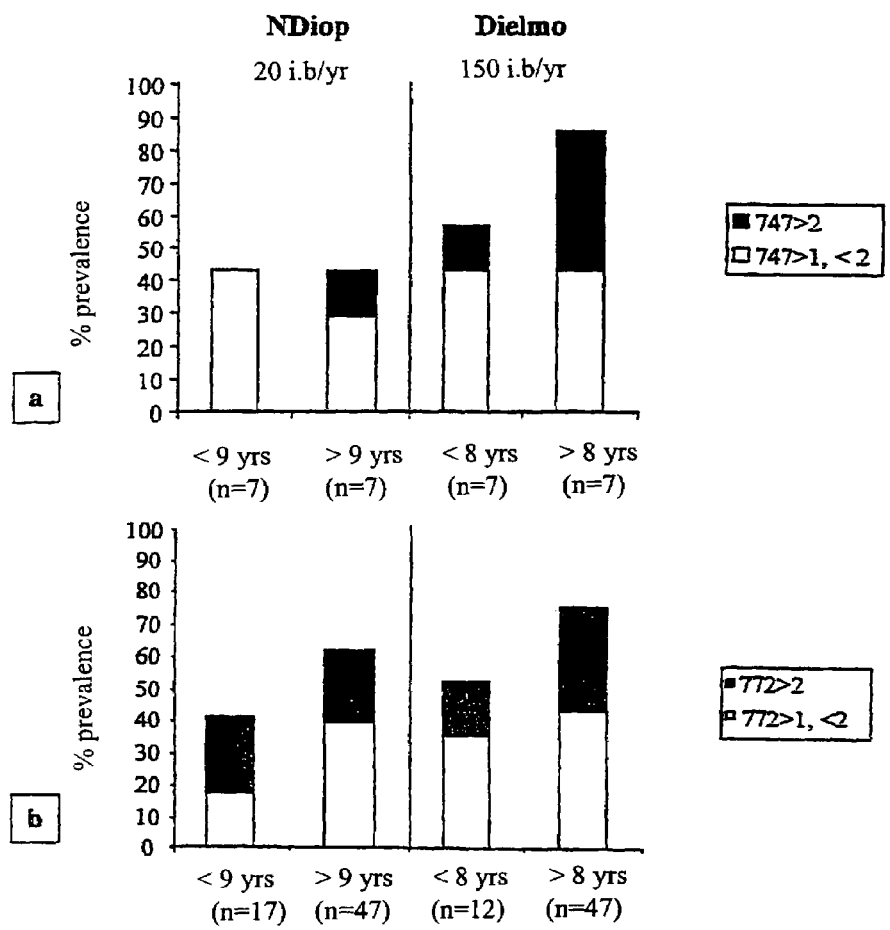
Figure 3.5

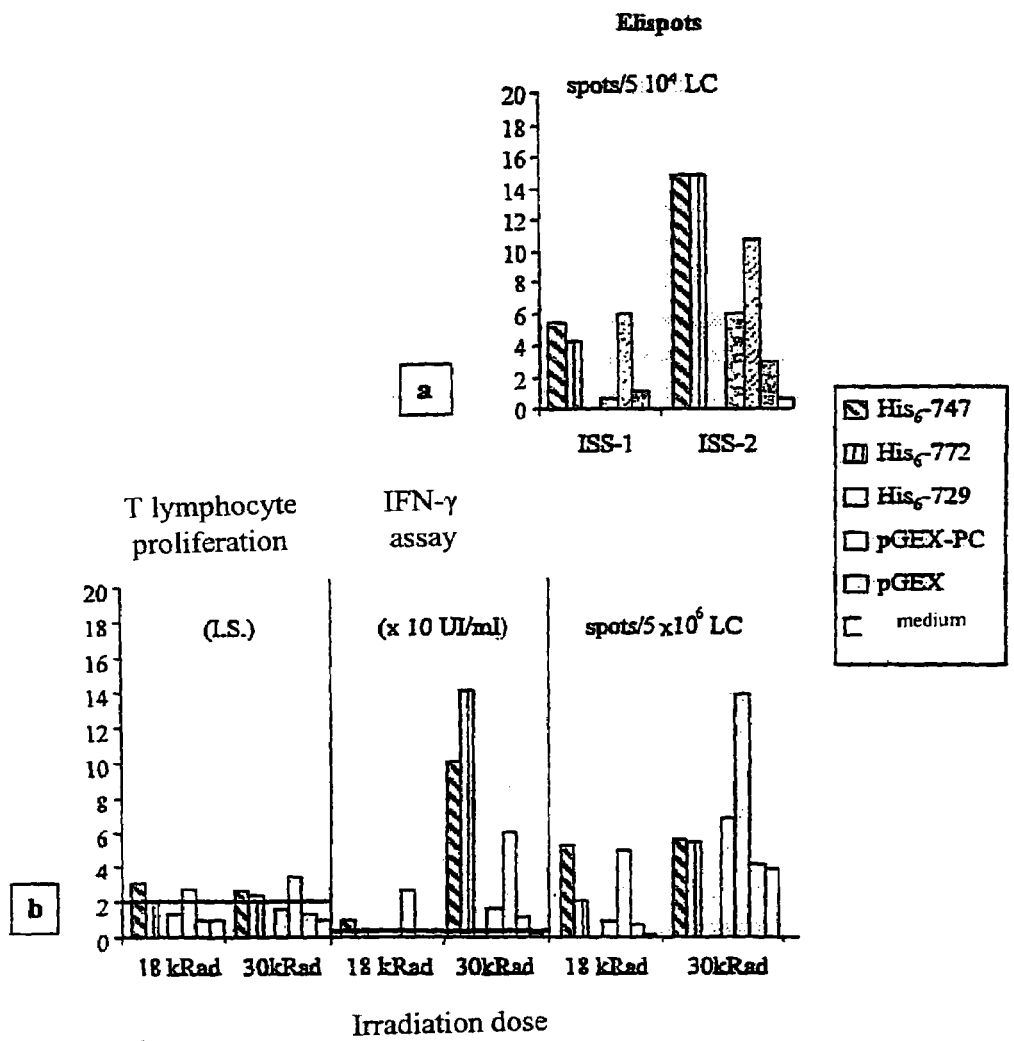
Figure 3.6

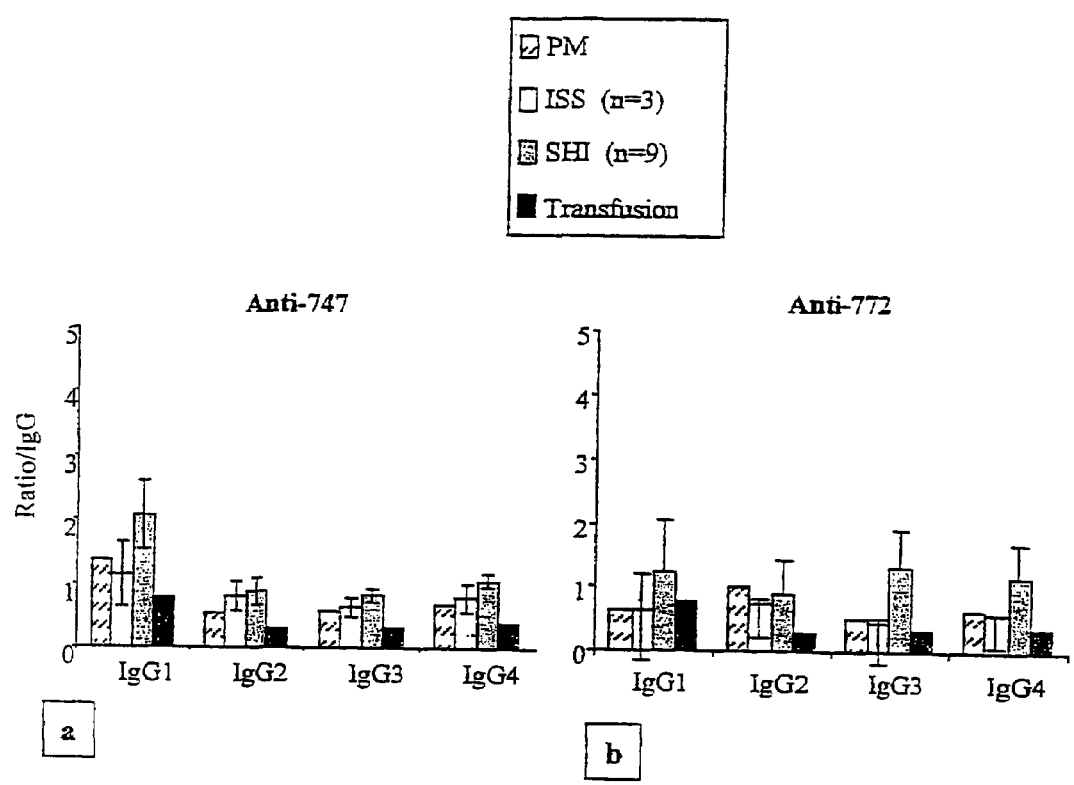
Figure 3.7

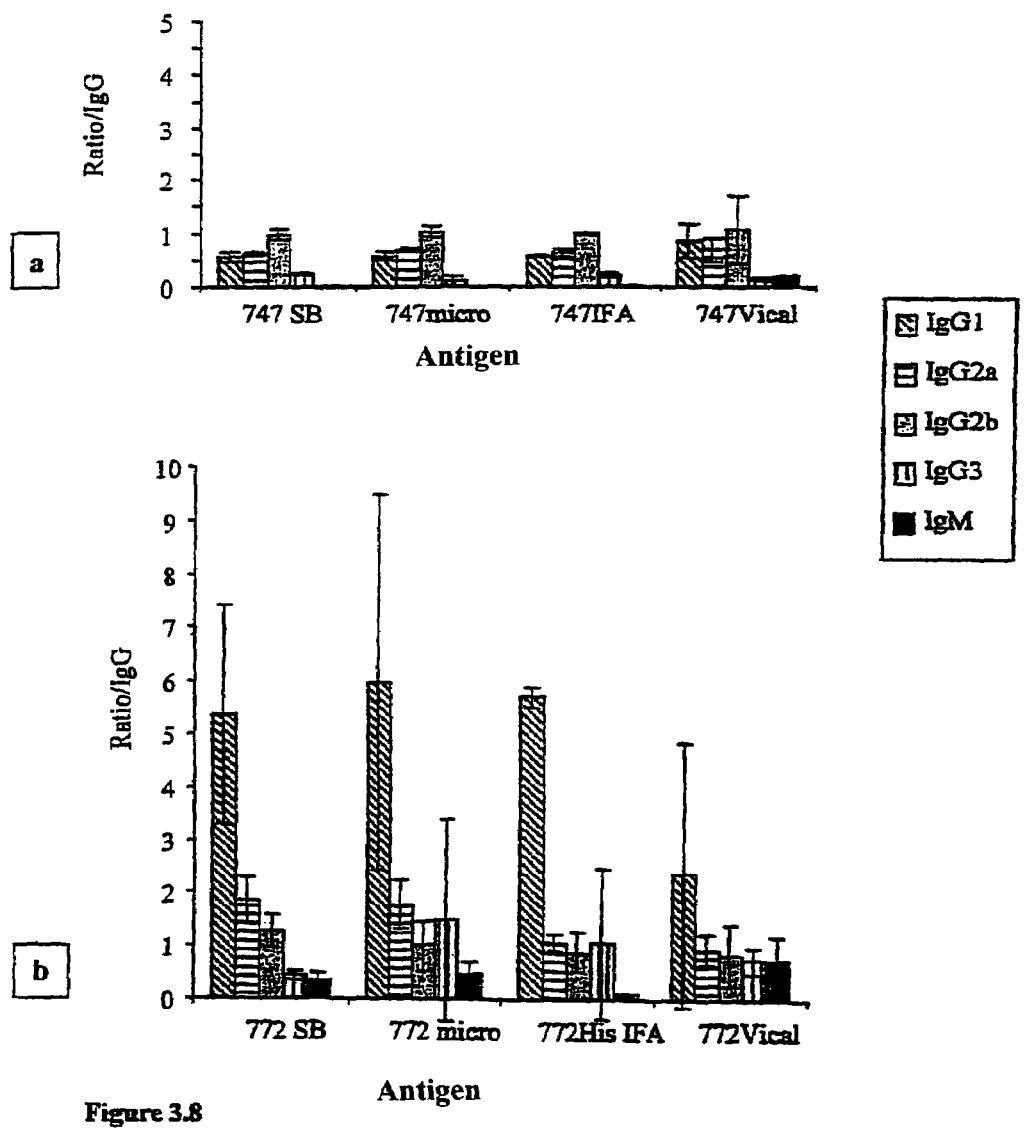
Figure 3.8

PLASMODIUM FALCIPARUM ANTIGENS AND THEIR VACCINE AND DIAGNOSTIC APPLICATIONS

CONTEXT OF THE INVENTION a) Field of the Invention

The present invention relates to novel *Plasmodium falciparum* antigens and to their vaccine and diagnostic applications. More particularly, the present invention relates to polypeptide molecules and immunogenic polynucleotide, to compositions comprising them, and to methods for diagnosis of and vaccination against malaria.

b) Brief Description of the Prior Art

Malaria is a disease caused by infection of protozoic parasites belonging to apicomplexes of the species *Plasmodium* and transmitted by female mosquitoes of the genus *Anopheles*. Despite the fact that since 1998, the WHO has classified malaria as one of the three infectious diseases of major interest to world health, alongside tuberculosis and AIDS, there is still no effective vaccine against this disease.

Previous studies have determined antigenic polypeptides for the pre-erythrocytic stage of the disease, in particular SALSA (Sporozoite Liver Stage Antigen) polypeptides described in European patent EP-A-0 407 230, LSA 1 (Liver Stage Antigen) polypeptides described in International patent application WO 92/13884 and LSA-3 described in French patent FR 2 735 478.

The present invention relates to novel polynucleotide and polypeptide molecules specific to the pre-erythrocytic stages and to their use as an active principle for an anti-malaria vaccine or in methods for diagnosing the disease.

SUMMARY OF THE INVENTION

Applicant has identified a series of 120 genomic DNA fragments coding for proteins expressed in the pre-erythrocytic stages, i.e., the sporozoite stage and/or the liver stage. Initial characterization of this series of clones has resulted in identification of the LSA-1 antigen, then SALSA, then STARP, then LSA-3. More recent work on 10 fragments from the same clone library coding for pre-erythrocytic stages have provided more information concerning 8 of them; 3 have been shown to be genes that are already known to be expressed in the erythrocytic stage and the other 5 are novel genes that have not been described to date, and for which expression during the pre-erythrocytic stages has been confirmed.

Further, work carried out using cells from volunteers protected by irradiated sporozoites, cells from chimpanzees protected by the same method and cells from chimpanzees such as *Aotus trivirgatus*, protected by immunization with the antigen LSA-3, have led to a characterization of cell responses with a high level of γ-interferon secretion, generally associated with a low level of antibody production, as being associated with the protected condition, and vice-versa.

Two of the novel pre-erythrocytic genes that were studied, DG747 and DG772, have several remarkable properties: they generate cell responses with a high level of γ-interferon, detected by ELISPOT in volunteers protected by irradiated sporozoites, which are also found for several regions of the LSA-3 antigen but which are absent for 4 regions of the LSA-1 antigen, two of SALSA, two of STARP and two of the "CircumSporozoite Protein". Those two clones are also positive in the same tests in chimpanzees protected by irradiated sporozoites. The differential response profile between the protected chimpanzees and chimpanzees that received irradiated sporozoites in too high dose, and not protected, is identical to that recorded with the LSA-3 molecule which is capable of inducing protection. This response profile corresponds, according to studies carried out with the rodent, to the capacity to induce specific cell recruitment on the intra-hepatic level. The complete sequence of the two genes has been identified. The corresponding proteins have high antigenicity in individuals exposed to the parasite in an endemic zone (reaction in 80% of adults in the endemic zone). Their location on the surface of the sporozoite and their production during intra-hepatic maturation of the parasite has been confirmed by various biological methods. Their immunogenicity in the animal in the form of recombinant proteins or in the form of plasmids (genetic immunization) has been demonstrated.

More particularly, one aspect the present invention concerns an isolated or purified polynucleotide comprising a nucleotide sequence with at least 60%, preferably at least 80% and more preferably at least 95% identity with SEQ ID NO:1 (DG747) or SEQ ID NO: 2 (DG772).

In a further aspect, the present invention concerns an isolated or purified polynucleotide comprising at least 10 consecutive nucleotides identical to SEQ ID NO:1 or SEQ ID NO: 2. The invention also concerns isolated or purified polynucleotides which hybridize under highly stringent conditions with a polynucleotide as defined above.

In a still further aspect, the present invention concerns an isolated or purified polypeptide coded by a polynucleotide as defined above. In a preferred implementation, the polypeptide of the invention has at least 60%, preferably at least 80% and more preferably at least 95% homology with SEQ ID NO: 3 (DG747) or SEQ ID NO: 4 (DG772). In a further preferred embodiment, the polypeptide of the invention comprises at least 5 consecutive amino acids identical to one of SEQ ID NOs: 3 to 8. In a still further preferred embodiment, the polypeptide of the invention has at least 40%, preferably at least 60%, more preferably at least 80% and still more preferably at least 95% identity with one of SEQ ID NOs: 3 to 8, 10 and 12. The invention also encompasses recombinant or chimeric polypeptides comprising at least one polypeptide as defined above.

In a further aspect, the present invention concerns an isolated or purified antigen consisting of a polynucleotide or a polypeptide as defined above.

In a still further aspect, the present invention concerns an antigenic conjugate constituted by a polynucleotide and/or a polypeptide as defined above; and a support onto which said polynucleotide/polypeptides are adsorbed. Said conjugate can advantageously be used to immunize individuals who have been infected or who are susceptible of being infected with malaria.

In a further aspect, the present invention concerns monoclonal or polyclonal antibodies, preferably humanized, specifically recognizing at least one of the polynucleotides, polypeptides and/or conjugates defined above. In a related aspect, the present invention concerns pharmaceutical compositions which comprise, as the active substance, one or more of said polyclonal or monoclonal antibodies in association with a pharmaceutically acceptable vehicle.

In accordance with a further aspect, the present invention concerns a cloning or expression vector (such as plasmids, cosmids or phages) comprising a polynucleotide sequence in accordance with the present invention. The invention also encompasses host cells comprising said vector, and more particularly recombinant *E. Coli* cells deposited at the C.N.C.M [National Collection of Microorganism Cultures], located at 28 Rue du Docteur Roux, F-75724, Paris, Cedex 15, on 23$^{rd}$ May 2001 with accession numbers I-2671 and I-2672.

In a further aspect, the present invention concerns an immunogenic composition comprising polynucleotides, polypeptides and/or conjugates as defined above; and a pharmaceutically acceptable vehicle.

A further related aspect of the present invention concerns an anti-malaria vaccine comprising polynucleotides, polypeptides and/or conjugates as defined above; and a pharmaceutically acceptable vehicle. Preferably, the compositions and vaccines of the present invention are used to produce drugs intended for the prevention and/or treatment of malaria.

In accordance with a further aspect, the present invention concerns methods and kits for in vitro diagnosis of malaria in an individual who is susceptible of being infected with *Plasmodium falciparum*. In accordance with a preferred implementation, the method comprises the following steps:
  a) bringing a biological tissue and/or fluid removed from an individual who is susceptible of being infected with *Plasmodium falciparum* into contact with an antibody as defined above under conditions allowing an immunological reaction to allow the formation of immune complexes; and
  b) detecting the immune complexes formed in vitro.

In accordance with a further preferred embodiment, the diagnostic method comprises the following steps:
  a) bringing a biological tissue and/or fluid removed from an individual susceptible of being infected with *Plasmodium falciparum* into contact with polynucleotides, polypeptides and/or those conjugates as defined above under conditions allowing an immunological reaction to allow the formation of immune complexes involving at least one of said elements and antibodies that may be present in said biological tissue or fluid; and
  b) detecting any immune complexes that are eventually formed in vitro.

In accordance with a preferred embodiment, the kit of the invention for in vitro diagnosis of malaria comprises the following elements:
  a) at least one element selected from the group formed by: polynucleotides, polypeptides and conjugates as defined above;
  b) reagents for constituting a medium suitable for a binding reaction between a test sample and at least one of the elements defined in a); and
  c) reagents allowing the detection of antigen-antibody complexes produced by said binding reaction, said reagents also possibly carrying a label or being susceptible of being themselves recognized by a labeled reagent.

In accordance with a further preferred embodiment, the kit of the invention comprises the following elements:
  antibodies as defined above;
  reagents for constituting a medium suitable for a binding reaction between a test sample and at least one said antibody; and
  reagents allowing the detection of antigen-antibody complexes produced by said binding reaction, said reagents also possibly carrying a label or susceptible of being themselves recognized by a labeled reagent.

One major advantage of the present invention is that it provides novel polynucleotide and polypeptide molecules specific to the pre-erythrocytic stages of malaria. The polynucleotide and polypeptide molecules of the invention have several remarkable properties. They generate cell responses with a high level of γ-interferon. The results obtained also suggest that the polynucleotide and polypeptide molecules of the invention have the capacity to induce specific cell recruitment on the intra-hepatic level. The invention also provides effective anti-malaria vaccines and diagnostic methods sensitive to malaria.

A number of other aims and advantages of the present invention will become apparent from the following non-limiting description of the invention.

BRIEF DESCRIPTION OF THE DRAWINGS

FIGS. 1A, 1B, 1C and 1D show nucleotide sequence listings (SEQ ID NOs: 1 and 2) and amino acid sequences (SEQ ID NOs: 3 and 4) of DG747 and DG772.

FIG. 1E shows the degenerate repeat sequences characteristic of the DG747 clone (SEQ ID NOs: 5-8).

FIG. 2A shows the gene sequence coding for DG747 (SEQ ID NOs: 9 and 10) extracted from the genome database for the 3D7 clone of *Plasmodium falciparum* (gene PfB00155). The greyed out areas (■) show the sequence corresponding to the DG747 clone. The difference with the sequence derived from strain T9.96 (positions 344, 357) is shown in bold in the sequence.

FIG. 2B shows the sequence of the gene coding for DG772 (SEQ ID NOs: 9 and 10) extracted from the genome database for the 3D7 clone of *Plasmodium falciparum*. The greyed out areas (■) show the sequence corresponding to the DG772 clone. Difference from the sequence derived from strain T9.96 (position 3612) is shown in bold in the sequence.

FIGS. 3.1(*a*) and 3.1(*b*) are diagrammatic representations of proteins corresponding to DG747 (a) and DG772 (b). The solid arrows indicate the position of primers used to study the fragment conservation. The open arrows indicate primers used in the RT-PCR reaction. 3.1(*a*): the hatched portion indicates a repeat region. 3.1(*b*): the two consensus regions 5' cys and 3' cys are shown on the gene. The dotted portion represents the assumed transmembrane regions and non-transcribed regions.

FIGS. 3.2A, 3.2B, 3.2C and 3.2D show IFATs of the sporozoite and blood stages of *P. falciparum* and sporozoites of *P. yoelii* with anti-DG747 or anti-DG772 antibodies. FIG. 3.2A, FIG. 3.2B: sporozoite of *P. falciparum* (A) or *P. yoelii* (B) labeled with anti-747 or anti-772; FIG. 3.2C, FIG. 3.2D: asynchronous blood stage labeled for anti-747 (C) or anti-772 (D); a, t, s: ring, trophozoite or schizont forms respectively.

FIGS. 3.3(*a*) and 3.3(*b*) show Western blots of *P. falciparum*, *P. yoelii* and *P. berghei* using anti-His$_6$-747 (a) and anti-His$_6$-772 (b) antibodies. Track 1: *P. falciparum* sporozoites; Track 2: *P. falciparum* blood stage, ring form; Track 3: *P. falciparum* blood stage, schizont form; Track 4: supernatant from asynchronous culture; Track 5: human red blood cells; Track 6: *P. yoelli* sporozoites; Track 7: *P. yoelii* blood stage; Track 8: *P. berghei* blood stage; 9: mouse red blood cells.

FIGS. 3.4(*a*), 3.4(*b*) and 3.4(*c*) show photographs of the results of PCR of the DNA from 12 different strains with specific primers for DG747 3.4(*a*) and DG772 3.4(*b*). The control, 3.4(*c*), is a constitutive gene, PCNA [Kilbey, 1993 #519]. The DNAs used were derived from the strains: NF54, B1, F32, D7, D25, D28, D41, D50, D51, H1, L1, Mad20, T9.96, PA (wells 1 to 14, left to right). Well 15 contains no DNA. The size of the PCR product, corresponding to that expected, is indicated to the side of the arrows.

FIGS. 3.5(a) and 3.5(b) illustrate by means of graphs the prevalence of humoral responses against $His_6$-747 (a) and $His_6$-772 (b) in two age groups and in two different endemic zones.

FIGS. 3.6(a) and 3.6(b) illustrate by means of graphs the cell responses against $His_6$-747 and $His_6$-772 in humans and chimpanzees immunized with irradiated sporozoites. FIG. 3.6a: Elispot detection of secretion of IFN-γ from cells deriving from humans immunized with irradiated sporozoites; FIG. 3.6b: cell responses of chimpanzees immunized with irradiate sporozoites, detected by stimulating the proliferation of T lymphocytes and secretion of IFN-γ (by assay and Elispots). I.S.: Stimulation index; UI: International Units; LC: Leukocytes (mononuclear peripheral blood cells). $His_6$-729, PC-pGEX: recombinants belonging to the LSA3 protein; pGEX: GST protein. Threshold values are indicated by a horizontal line on the graph.

FIGS. 3.7(a) and 3.7(b) illustrate by means of graphs the distribution of IgG isotypes in humoral responses against $His_6$-747 and $His_6$-772 from individuals differentially exposed to malaria. ISS: Volunteers immunized with irradiated sporozoites; SHI: Hyper-immune serum; Transfusion: Serum from persons who had contracted malaria by transfusion of infected blood. The level of responses detected by ELISA are shown with respect to the level of total IgG obtained. The standard deviation is shown on the graph.

FIGS. 3.8(a) and 3.8(b) illustrate by means of graphs humoral responses for mice immunized with four recombinant protein formulations. FIG. 3.8a: anti-747 responses; FIG. 3.8b: anti-772 responses; SB: with adjuvant SBS2A; micro: recombinant adsorbed onto microparticles; IFA-incomplete Freund's adjuvant; Vi: in the form of DNA in the vector VR1020 in PBS.

DETAILED DESCRIPTION OF THE INVENTION

The originality of the present invention is based on the development of novel polynucleotide and polypeptide molecules specific to the pre-erythrocytic stage of malaria and to their uses as an active principle in an anti-malaria vaccine or in methods for diagnosing the disease.

More particularly, the invention relates to polynucleotides with a nucleotide sequence of at least 10, 20, 30, 40, 50, 75, 100, 150 or 200 consecutive nucleotides and having at least 60%, 65%, 70%, 75% and preferably 80%, 85%, 90%, more preferably at least 95%, 97% or even 100% identity with SEQ ID NO:1 or 2. Other molecules of the invention hybridize under highly stringent conditions with the above nucleotide sequences, and more particularly with SEQ ID NOs: 1 and/or NO 2. A non-limiting example of highly stringent conditions is described in the following method:
 a) pre-hybridization and hybridization at 68° C. in a solution containing: 5×SSPE (1×SSPE=0.18 NaCl, 10 mM $NaH_2PO_4$); 5× Denhardt's solution; 0.05% (w/v) sodium dodecyl sulphate (SDS); and 100 μg/ml of salmon sperm DNA;
 b) washing twice at ambient temperature for 10 min in the presence of 2×SSPE and 0.1% SDS;
 c) washing at 60° C. for 15 min in the presence of 1×SSPE and 0.1% SDS; and
 d) washing at 60° C. for 15 min in the presence of 0.1× SSPE and 0.1% SDS.

The invention also relates to polypeptides (and fragments thereof) which are derived from the above nucleotide sequences and preferably polypeptides with at least 10, 20, 30, 40, 50, 75, 100, 150 or 200 consecutive amino acids and having at least 60%, 70%, 80%, 85% and preferably at least 90%, 95%, 97% or even 100% homology with one of the sequences selected from the group formed by SEQ ID NOs: 3 to 8, 10 and 12. Other molecules of the invention contain at least 10, 20, 30, 40, 50, 75, 100, 150 or even 200 consecutive amino acids having at least 60%, 70%, 80%, 85% and preferably at least 90%, 95%, 97% or even 100% identity with SEQ ID NOs: 3 to 8, 10 and 12.

It is well known in the field how homology and identity percentages between different sequences are determined. As an example, one method for analyzing the alignment of the nucleotide and peptide sequences of the invention is advantageously the GAP GCG™ (Genetic Computer Group) program from the UNIX™ (Wisconsin Sequence Analysis Package™) suite, the Needleman and Wunsch algorithm. The parameters used are the default parameters or the following parameters: to compare the nucleotide sequences: "gap penalty"=50; "gap extension penalty"=3; and to compare amino acid sequences: "gap penalty"=5; "gap extension penalty"=0.30.

The peptides of the present invention can be prepared using any suitable method. In particular, they can be obtained by chemical synthesis, but it is also possible to obtain them biologically using different vectors in suitable appropriated cell cultures such as that described below.

The molecules of the invention can be used as they are or they can be modified (chemical conjugates, fusion protein) if necessary. For example, it may be possible to envisage modifications (chemical or nucleotidic or peptidic) allowing the nucleotides/peptides to pass through certain biological barriers, to solubilize better, or to facilitate their incorporation into particular galenical forms, such as for example liposomes or microparticles. It should also be noted in this regard that the peptides of the present invention can be in the deglycosylated or glycosylated form, if necessary. A person who is conversant with the field of the invention could obtain different polynucleotides/polypeptides and would also be able to determine which of the polynucleotides/polypeptides obtained had a suitable biological activity.

Thus, the invention also pertains to a method for preparing a peptide of the invention, by transforming a host cell using an expression vector (plasmid, cosmid, virus, etc) comprising DNA sequences coding for the peptides of the invention, followed by culturing the transformed host cell and recovering the peptide in the culture medium.

The invention thus also concerns any vector (cloning and/or expression) and any host cell (prokaryotic or eukaryotic) transformed by said vector and comprising regulating elements allowing expression of the nucleotide sequence coding for a peptide of the invention.

More particularly, the invention relates to cells of recombinant *E. coli* containing an insert corresponding to the polynucleotides defined by SEQ ID NOs: 1 and 2. More preferably, the invention relates to *E. coil* cells containing an insert corresponding to the polynucleotides defined by SEQ ID NOs: 1 and 2 deposited at the CNCM on $23^{rd}$ May 2001 with accession numbers I-2671 and I-2672, respectively. Briefly, said cells were obtained by transforming a plasmid containing either an insert corresponding to the polynucleotides defined by SEQ ID NO: 1, or an insert corresponding to the polynucleotides defined by SEQ ID NO: 2 in the *E. coil* Dh5α strain. Each plasmid was obtained from a recombinant λgt11 phage containing the insert. PCP was carried out with primers flanking the insert and that amplified insert was digested with EcoR1 and sub-cloned into the $pTreHis_6$ vector (Invitrogen™) at the EcoR1 sites.

The use of vectors for the expression of proteins and peptides in the cells of a host, in particular the human, is known and will not be described in further detail. It may be advantageous to use vectors incorporating sequences that are capable of increasing the immunogenicity of the polynucleotides/polypeptides of the present invention, such as CPG sequences, the GMCSF (granulocyte macrophage colony stimulating factor) gene, or cytokine genes. The specific constructions clearly depend on the host, the epitope and on the vector employed.

The peptides of the present invention and the polynucleotides coding for them can also be used to prepare polyclonal or monoclonal antibodies that are capable of binding (preferably specifically) to at least one peptide/polynucleotide of the invention. The present invention thus also relates to such purified antibodies which can be obtained by very well known techniques, such as the technique described by Kolher and Milstein (Continuous cultures of fused cells secreting antibody of predefined specificity, Nature (1975), 262: 495-497).

In one advantageous implementation of the invention, at least one portion of the immunogenic peptides/polynucleotides of the invention is conjugated to a support onto which it is absorbed or bound in a covalent or non-covalent manner to its C- and/or N-terminal end. The support can be constituted by carrier molecules (natural or synthetic), which are physiologically acceptable and non toxic. Said carrier molecules can increase the immunogenicity of the peptides of the invention by means of complementary reactive groups respectively carried by the carrier molecule and the peptide. Examples of carrier molecules which can be mentioned are natural proteins such as tetanus anatoxin, ovalbumin, serum albumin, hemocyamines, PPD (purified protein derivative) of tuberculin, etc. Examples of synthetic macromolecular supports that can be mentioned for example, are polylysins or poly(D-L-alanine)-poly(L-lysine). Hydrocarbon or lipid supports that can be mentioned are saturated or unsaturated fatty acids. The support can also take the form of liposomes, particles and microparticles, vesicles, latex bead microspheres, polyphosphoglycans (PGLA) or polystyrene.

The invention also concerns vaccine/therapeutic (drug) compositions comprising the peptides/polynucleotides, conjugates and/or polyclonal or monoclonal antibodies described above, and a pharmaceutically acceptable vehicle. The invention also concerns immunogenic compositions capable of inducing protection by a challenge infection with *Plasmodiums*, both in vivo and in vitro and, preferably, protection by a challenge infection with *Plasmodium falciparum*. Preferably, the compositions of the invention allow the production of γ-interferon by the leukocytes of subjects immunized with irradiated sporozoites and/or the production of a humoral IgG response of the IgG1, IgG2, IgG3 and/or IgG4 type.

Said compositions may be advantageous for in vivo administration for the treatment or prevention of malaria in the human being. Clearly, the use of compositions based on antibody generally necessitates that they are compatible with administration to the human being. It may be antibody humanized by known techniques or directly expressed in situ from the DNA sequence, for example using the technique described by Ren E C, "Cellular and molecular approaches to developing human monoclonal antibodies as drugs" (1991), Ann Acad Med Singapore, 20: 66-70.

The compositions of the present invention can be in any of the usual solid or liquid forms for pharmaceutical administration, i.e., for example in liquid administration forms, as a gel, or any other support allowing controlled release, for example. Among usable compositions that can be cited are injectable compositions, more particularly intended for injection into the blood circulation in the human being.

The compositions of the invention can also comprise components that increase or susceptible to increase the immunogenicity of peptides, in particular other immunogenic peptides, immunity adjuvants which may or may not be specific, such as alum, QS21, Freund's adjuvant, $SBA_2$ adjuvant, montanide, polysaccharides or equivalent compounds.

The present invention also concerns compositions intended for administration to express the peptides described above in situ. As an example, when injecting "naked DNA" coding for the immunogenic peptides of the invention, this injection in some cases results in expression of the coded peptide and to an immune response against said peptide. It is also possible to use naked DNA systems, but comprising their own expression system or expression vectors as described above. The expression vectors are in some cases susceptible of improving the activity of the expressed peptides. Vaccination systems employing DNA sequences are known and have already been widely described in the literature. Examples of vaccination employing DNA sequences have been described in International patent application WO 95/111307 and in the publication of Bot et al (DNA immunization of newborn mice with a plasmid expressing nucleoprotein of influenza virus (1996), Viral Immunol, 9:207-210).

The invention also concerns in vitro methods for diagnosing malaria in an individual susceptible of being infected with *Plasmodium falciparum*.

In one embodiment of the invention, the method comprises the following steps:
 a) bringing a biological tissue and/or fluid removed from an individual who is susceptible of being infected with *Plasmodium falciparum* under conditions allowing an immunological reaction into contact with an antibody as defined above to allow the formation of immune complexes; and
 b) detecting immune complexes formed in vitro.

In one implementation of the invention, the diagnostic method comprises the following steps:
 a) bringing a biological tissue and/or fluid removed from an individual susceptible of being infected with *Plasmodium falciparum* under conditions allowing an immunological reaction into contact with polynucleotide/polypeptide molecules as defined above to allow the formation of immune complexes involving at least one of said molecules and antibodies that may be present in said biological tissue or fluid; and
 b) detecting any immune complexes that are formed in vitro.

The invention also concerns kits for diagnosing malaria in an individual. In one implementation of the invention, the kit comprises the following elements:
 a) at least one element selected from the group formed by: polynucleotide molecules, polypeptide molecules, and conjugates as described above;
 b) reagents for constituting a medium suitable for a binding reaction between a test sample and at least one of the molecules defined in a); and
 c) reagents allowing the detection of antigen-antibody complexes produced by said binding reaction, said reagents also possibly carrying a label or being susceptible of themselves being recognized by a labeled reagent.

In a further implementation of the invention, the kit comprises the following elements:
 antibodies as defined above;
 reagents for constituting a medium suitable for a binding reaction between a test sample and at least one said antibody; and reagents allowing the detection of antigen-antibody complexes produced by said binding reaction, said reagents also possibly carrying a label or susceptible of being themselves recognized by a labeled reagent.

Although the description of the present invention uses the term "peptide" and "polypeptide", it is clear that the invention is not limited to compounds formed by the union of a limited number of amino acids. In fact, the flexibility of recombinant techniques enables proteins comprising a plurality of identical or different epitopes to be formed which are susceptible of improving the immunogenic activity of the final product. The present invention therefore also encompasses immunogenic polymers comprising between two and ten peptides selected from the polypeptides defined above. Similarly, the present invention includes oligonucleotides having a nucleotide sequence coding for oligonucleotides incorporating one or more polynucleotides as defined above.

The examples below illustrate other characteristics and advantages of the present invention.

EXAMPLES

The examples below serve to illustrate the scope of uses of the present invention and do not limit that scope. Modifications and variations can be made without departing from the spirit and scope of the invention. Although methods or products equivalent to those described below can be employed to test or implement the present invention, preferred materials and methods have been described.

1) Introduction 1.1 History of Malaria

Malaria is a disease caused by infection of protozoic parasites belonging to apicomplexes of the species *Plasmodium* and transmitted by female mosquitoes of the genus *Anopheles*. Sustained effort and the eradication program begun in the 50s, financed by the WHO, have limited the zones in which the disease is propagated and reduced the number of infected persons. Since then, a reduction in the effectiveness of means for combating the parasite has caused an increase in cases of malaria compared with 20 years ago. Today, malaria is concentrated in the sub-tropical belt where between 300 and 500 million clinical cases are recorded annually, with a minimum of 3 million succumbing, mainly because of infection by *Plasmodium falciparum*. Following the appearance and extension of global resistance to the only effective drugs, and because the regions affected are extending, since 1998, the WHO has classified malaria among the three infectious diseases of major interest to the world public health, alongside tuberculosis and AIDS.

A description of malarial infection, the clinical signs of which are highly characteristic, can be found in the writings of the oldest civilizations, such as the Nei Ching, the great medical directory of the Chinese emperor Huang Ti (2700 BC), Mesopotamian tablets (2000 BC), Egyptian papyruses (1500 BC) and the Vedic writings (1500-800 BC). Part of Hippocrates' "book of epidemics" (460-370 BC) was devoted to the detailed description of tertiary or quaternary fevers and also mentions a relationship between splenomegaly and proximity to marshy zones. The term "paludism" designates a fever deriving from marshy zones (Latin: palude=marsh), which is also reflected in the term malaria (L: mall'aria) probably introduced by Sansovino in 1560 to describe the "bad air" issuing from the marshes. Draining those zones was one of the only known means of controlling malaria prior to the discovery of the infectious agent. Despite knowing the clinical signs, the parasite causing the disease was only discovered at the end of the 19$^{th}$ century.

In 1880, Charles Louis Alphonse Laveran observed the exflagellation of microgametes and altered hematia in blood (Laveran, 1880) and he associated these forms with the disease. His conclusions were controversial and were only accepted by 5 years later by others, in particular by the important Italian school. The mode of transmission of the disease remained unknown for 12 more years. In 1877, Patrick Manson demonstrated that the filariosis nematode (Elephantiasis) was transmitted by a mosquito. He was convinced that malaria followed a similar path. He advised Ronald Ross to focus his research on that matter and in 1897 this one described, for the first time, oocysts in mosquitoes that had fed on infected humans. Then, using bird *Plasmodium*, he was able to describe the entire life cycle of the parasite in the mosquito. This cycle was confirmed in 1898 for the plasmodial species in man by Italian researchers led by Battista Grassi.

For a long time it was believed that after inoculation by the mosquito, the sporozoite invaded the red blood cell of the host mammal directly, initiating the asexual and sexual blood cycle. An exo-erythrocytic cycle was described in 1908 in bird plasmodia by H de Beaupaire Aragao who demonstrated the development of atypical forms, in endothelial cells and macrophages, capable of releasing forms invading the red blood cells and of transforming into the typical pigmented forms of the parasite. However, it was believed that the tissue cycle was a particular form of those plasmodial species. It was only when observations during the course of induced malarial infections and closely followed in individuals (such as malariotherapy in the 1920-50s) were made that the presence of a supplementary tissue stage was postulated then actively researched. The pre-erythrocytic forms of the parasites of primates and humans were only discovered in 1948 when H E Shortt and P C C Garnham described hepatic forms derived from inoculations of sporozoites of *P. cynomolgi* (close to *P. vivax*) in the rhesus monkey (Shortt and Garnham, 1948). In 1951, the same stages were described for *Plasmodium falciparum* (Shortt et al, 1951) in a remarkable experiment in which a liver biopsy was removed from a volunteer who had been inoculated with millions of sporozoites. However, fresh outbreaks due to *P. vivax* or *P. ovale* were not explained, and the hypothesis of a "secondary" exo-erythrocytic cycle was expressed. Much after, this phenomenon was demonstrated experimentally. Then, a "dormant" stage of the hepatic form, the hypnozoite, was described in 1980 (Krotoski et al, 1980) for *P. cynomolgi*, the equivalent for the primate of *P. vivax*. This form is responsible for relapses after the parasite has been absent for a long time in the blood/exposure to parasites, and are characteristic of *P. vivax* and *P. ovale*. Recently, a supplemental stage, the merophore, a form deriving from blood forms, has been observed in the spleen and lymphatic ganglia of mice infected with murine *Plasmodium* (*P. yoelii*, *P. chabaudi* and *P. vinckei*) (Landau et al, 1999). This step of the cycle still remains to be described in plasmodial human species.

The parasite cycle, as understood today, is shown in FIG. 1 (the portions between parentheses are forms described for other species of *Plasmodium*, but not for *Plasmodium falciparum*).

1.2 Means for Combating the Spread of Malaria: The Need for Developing a Vaccine Since the start of the twentieth century, the two discoveries of the causal agent of the disease and of the disease vector have allowed rational defenses against malaria to be developed against malaria by attacking the parasite in the vertebrate host using drugs or by targeting the mosquito vector either with larvicides, or with insecticides, or using mosquito nets. The success in eliminating the disease in temperate zones after the second world war has led to the development of a malaria eradication program which culminated in the 60s when DDT was the principal tool against mosquitoes and chloroquine was the principal drug against the parasite. The size of the targeted endemic territories was thus reduced (quasi eradication in temperate zones) and the number of persons affected by the disease was initially reduced. However, the successes in tropical zones were short-lived. The number of patients has not stopped increasing, partly because of demographic increases, partly because of the appearance of resistance to insecticides and to the available drugs.

The appearance of resistance has required re-orientation towards other combating means. The existence of a natural immunity induced by exposure to parasites and the observation that the passive transfer of immunoglobulins from immune persons reduces parasitemia, and effective and sterilizing immunization by sporozoites attenuated by irradiation have rendered reasonable the postulation of a vaccine against malaria, the development of which thus constitutes a public health priority on a global scale.

1.3 The Search for Salvation by Immunity

Natural immunity against malaria is characterized by very slow development and the fact that it does not result in sterilizing protection. In hyperendemic zones, the acquisition of natural immunity against the erythrocytic stages manifests itself in children initially by tolerance to the parasite (anti-toxic immunity) then with age by a reduction in the parasite load in the blood (anti-parasitic immunity).

These observations, made during epidemiological studies, were confirmed by experimental infections. Malaria therapy applied to persons with neurosyphilis (Boyd and Coggeshall, 1938; Ciuca et al, 1943; James, 1936), allowed parameters to be defined which were involved in the acquisition of immunity in carefully controlled experiments. It was shown that acquired immunity was firstly dependant on the species and on the strain and secondly differed as a function of the stage of the infecting parasitic cycle. Until now, the precise mechanisms of anti-malarial immunity remain to be elucidated.

Because the clinical signs and transmission are uniquely due to the blood stages and that these are the most accessible both in vitro and in vivo, the majority of vaccine studies have concerned these stages. About thirty antigens expressed in erythrocytic parasites have been identified, particularly by monoclonal antibodies, and considered as vaccine candidates. However, tests with inducing protective immunity by the rare antigens that have been tested in man have remained fruitless until now.

The first immunization with pre-erythrocytic stages was attempted by the Sergent brothers in Algeria (Sergent and Sergent, 1910). The capacity of protecting in a sterilizing manner (absence of any blood parasitemia) was only obtained by immunization with sporozoites attenuated by irradiation. This approach was initiated by studies in the bird with sporozoites irradiated with UV radiation (Mulligan et al, 1941), and were repeated 20 years later with rodent plasmodia using sporozoites irradiated with X rays and later with γ rays, the dose of which could readily be controlled (Nussenzweig et al, 1967; Richards, 1966); immunity could be maintained by repeating with non-attenuated sporozoites (Orjih et al, 1982). In man, such protection was also obtained (Clyde, 1975; McCarthy and Clyde, 1977); however it was only induced after a very large number of inoculations with irradiated sporozoites and so such a vaccine procedure cannot be applied on a large scale.

For a long time, it was believed that protection was correlated with an observed phenomenon when sporozoites were incubated with immune serum, CS (Circum sporozoite) precipitation (Vanderberg et al, 1969). The major protein recognized by that serum, the CS protein, was thus considered to be responsible for that immunity. Since then it has formed the basis of many vaccine studies in many experimental models. However, until now, none of the studies has been able to reproduce an immunity as good as that induced by irradiated sporozoites.

A critical evaluation of the previous experimental results has led to the postulation that the hepatic stage and not the sporozoite is at the origin of sterilizing immunity (Druilhe and Marchand, 1989). The principal indication was the fact that protection could only be induced by inoculation with viable sporozoites, intravenously, capable of invading a hepatocyte and developing therein, and that hepatic forms derived from irradiated sporozoites persisted (Ramsey et al, 1982). Further, eliminating the hepatic stages would cause susceptibility to infections by sporozoites in previously protected animals (Londono et al, 1991; Scheller and Azad, 1995).

The hepatic stage has unique characteristics. The hepatocyte is a nucleated cell that is metabolically highly active and expresses molecules of the major histocompatibility complex. Hepatic schizogony causes the formation of between 10000 and 30000 merozoites while 4 to 32 merozoites are released by a blood schizont. Merozoites from these two stages have morphological differences, but it is not known whether functional or molecular differences exist as only blood merozoites have been able to be studied extensively.

Because only a few hepatocytes in the liver are infected and that in vitro, culture techniques remain delicate and difficult, this has constituted a major obstacle to developing knowledge regarding the hepatic stage and the search for antigens expressed at that stage.

1.4 Screening for Specific Stage Antigens

The first strategy for establishing stage-specific expression is the generation of libraries of complementary DNA from messenger RNA from different stages. This was accomplished several times for the blood stages (Chakrabarti et al, 1994; Watanabe et al, 2001) and more recently once for the sporozoite stage (Fidock et al, 2000). However, that approach is not possible for the hepatic stage of human plasmodia. A further mean is the generation of specific antibodies in animal models. This is easy for the erythrocytic stages but for the hepatic stage, a number of attempts have failed as injecting the hepatic stages of *Plasmodium falciparum* have only induced a very few antibodies in mice. A final approach is immunological screening based on the use of antibodies from naturally immunized individuals. That approach has demonstrated, for the first time, that antigens other than CS are present on the sporozoite surface (Galey et al, 1990).

1.5 Laboratory Strategy for Identifying Antigens Expressed at the Pre-Erythrocytic Stages In order to overcome the difficulty of screening at pre-erythrocytic stages, a strategy for screening *Plasmodium falciparum* antigens potentially expressed in the sporozoite and hepatic stages has been developed (Marchand and Druilhe, 1990).

The principle was to seek individuals in whom the predominant immune response was against the pre-erythrocytic stages. We obtained serum from individuals (PM serums) living in an endemic zone for over 20 years and who had never clinical events as they were permanently under prophylactic treatment with chloroquine (a schizonticide effective against the blood stages, but with no effect on the hepatic stages). The corresponding serum only weakly recognized blood stages under Western Blot and IFI (titers of less than 1/200), while titers against the sporozoite and hepatic stages of the parasite were in the range 1/3200 to 1/6400 in IFI and they labeled several polypeptides on protein extracts from *Plasmodium falciparum* sporozoites; the serum thus contained antibodies specific to antigens expressed in the pre-erythrocytic stages.

Those serums were used to screen a gene library from *Plasmodium falciparum* (constructed by Odile Mercereau Puijalon). The genomic DNA from the parasitic clone T9-96 was methylated and digested with Dnase 1, and fragments with a size of 200 to 2500 base pairs were introduced into the EcoR1 site of the λgt11 phage (Guérin-Marchand et al, 1987).

Of the 7 million fragments of DNA that were generated, 2000 clones producing a recombinant antigen recognized by hyperimmune serum (HIS) from immune individuals living in the endemic zone were then screened with the PM serum. 120 clones were then selected and stage-specific expression of the corresponding antigens was determined by IFI tests, with immunopurified human antibodies on each recombinant protein, on sporozoites, the hepatic stages and the blood stages of *P. falciparum, P. yeolii* and occasionally with *P. berghei* and *P. vivax*.

The first antigen to be studied and against which the humoral responses were the greatest in several serums from individuals living in an endemic zone was the Liver Stage Antigen, LSA-1 (Guérin-Marchand et al, 1987). It remains the only characterized antigen to be expressed uniquely at the hepatic stage.

Following LSA-1, 3 antigens, STARP, SALSA and LSA-3, were selected from the various criteria and characterized on the molecular level (Bottius et al, 1996; Daubersies et al, 2000; Fidock et al, 1994), and immunologically by L. Benmohammed, K. Brahimi, J.-P. Sauzet and B Perlaza (BenMohammed et al, 1997; Perlaza et al, 1998; Sauzet et al, 2001). Those antigens are expressed both on the sporozoite surface and in the hepatic stage.

LSA-3 is the only antigen that is differentially recognized by serum from volunteers or chimpanzees protected by immunization with irradiated sporozoites. It is the only one to have induced sterilizing and long term protection in chimpanzees (Daubersies et al, 2000), and will soon be tested in phase I and II clinical trials.

2) Material and Methods 2.1 Molecular Biological Techniques 2.1.1. Bacterial Strains DH5α: supE44 ΔlacU169(φ80 lacZ ΔM15) hsdR17 recA1 gyrA96 thi-1 relA1.

2.1.2. Parasite Strains:

NF54 from an isolate from a European patient infected in Africa (ATCC MRA151) (Walliker et al, 1987).

3D7, the reference strain used in the genome project, is a clone from the (ATCC MRA151) strain (Walliker et al, 1987).

T9.96, a strain from a Thai patient, ATCC: MRA153, (Thaithong et al, 1984).

For the polymorphism tests, distinct strains were employed: B1 (Brazil); F32, D7, D28, D50 from Tanzania; D28 from Senegal, D41 from India; D51 from Myanmar, L1 from Liberia; H1 from Honduras, Mad20 from Papua New Guinea, and PA from Palo Alto, South West America (Stricker et al, 2000).

The sporozoites were derived from the NF54 strain and obtained by passage through *Anopheles Gambiae* REF.

2.1.3. PCR from Phage Extracts or Phage DNA

The Expand High Fidelity Kit™ (Mannheim Boehringer, Germany) was used as indicated by the supplier with 2 mM of $MgCl_2$, 3.5 units of Taq polymerase, 0.2 mM of deoxyribonucleotides (dNTP), 50 nM of 21D primers 5' (CCTGGAGC-CCGTCAGTATCGGCGG; SEQ ID NO: 13) and 26D primers 3' (GGTAGCGACCGGCGCTCAGCTGG; SEQ ID NO: 14) and 2 μl of purified DNA or phage extract. The reaction comprised initial denaturation for 2 minutes at 94° C., followed by 35 consecutive cycles of 15 seconds of denaturation at 94° C., 30 seconds hybridization at 50° C., and 2 minutes elongation at 68° C. The cycle was followed by incubation at 68° C. for 5 minutes.

2.1.3.1. Sub-Cloning in Histidine, pNAK and Topo Vectors

Depending on the amplification product of the phages, three procedures were employed:

The PCR products with a smear or a very small yield and being smaller and almost impossible to detect by digesting the DNA of the corresponding phage were cloned using a vector allowing direct cloning of the PCR product without successive digestion of a restriction enzyme using the TopoTA Cloning™ kit (Invitrogen, Netherlands). Topo cloning was also carried out for fragments for which only the sequence was to be determined.

PCR products with a size of less than 1 Kbp were digested, precipitated with ethanol and re-suspended in half of the initial volume of $H_2O$, then digested with 10 U of the restriction enzyme EcoR1 for 1 hour at 37° C., separated on a 2% agarose gel, purified on gel using the Qiagen gel extraction kit to give a volume of 50 μl.

Large less abundant PCR products (more than 1000 bp) were isolated from phage DNA purified by digestion with EcoR1, then by extraction of the insert on agarose gel.

2.1.3.2. Study of Gene Polymorphism in Different Parasitic Strains

The following primers were used to identify size polymorphisms of specific regions corresponding to the antigens studied.

```
747-1:
AAAAGTGATGATAGAAATGCTTGTG (5');    SEQ ID NO: 15

747-2:
TTTTGTTGATCTTACTTATTTCACC (3');    SEQ ID NO: 16

772-1:
CGGAATCAGGTTTAAATCCAAC (5');       SEQ ID NO: 17

772-2:
AGATCGTTTTTCATCAGGGGG (3');.       SEQ ID NO: 18
```

The cyclic reaction was carried out using a program comprising an initial denaturation step at 94° C. for 15 seconds, followed by 39 cycles comprising denaturation at 94° C. for 2 minutes, hybridization at 52° C. for 1 minute and elongation at 72° C. for 2 minutes. A 5 minute step at 72° C. terminated the reaction.

PCR was carried out using an Appligène Crocodile III™. The products were then analyzed on agarose gel.

2.1.4. DNA Purification 2.1.4.1. Recombinant Analysis

The positive PCR colonies were inoculated into 3 ml of medium containing the antibiotic corresponding to the vector used (100 μg/ml of ampicillin for Topo and Histidine, 20

μg/ml of kanamycin for the Vical vector) and 2 ml of the inoculum was used in preparing the plasmidic DNA with the Qiagen™ Miniprep Kit. The DNA obtained was successively digested with the restriction enzymes used in cloning and underwent to an agarose gel electrophoresis, to detect insertion of the fragment.

2.1.4.2. Fragment Isolation 100 ml of Luria Broth medium supplemented with a suitable antibiotic was inoculated with 1 bacterial colony comprising the recombinant and incubated at 37° C. overnight in a thermostated bath with vigorous agitation. The next day, the bacterial culture was harvested and the plasmic DNA was purified as described (Qiagen maxiprep™, Qiagen, Germany).

2.1.4.3. Immunization of Naked DNA Constructs

In order to eliminate endotoxins, which are present in bacteria and which can cause non specific responses during mouse immunizations, the DNA of the constructs was purified from 2 l of recombinant bacterial cultures, using the Qiagen EndoFree Plasmid Giga™ kit (Qiagen, Germany).

2.1.4.4. Purification of Recombinant DNA Phases

The phages were re-amplified on LB agarose dishes, by depositing 5 μl onto Topagar taken with 200 μl of Y1090 inoculum and leaving at 37° C. overnight.

A larger quantity was then produced in liquid culture. Firstly, a plaque pricked onto the dish was incubated with 200 μl of Y1090 inoculum and left at 37° C. with stirring for 15 minutes. Then 5 ml of antibiotic-free medium supplemented with 10 mM of $MgSO_4$ was added, and the culture was left with stirring for 4 hours until lysis occurred. 50 μl of Chloroform was added and it was centrifuged at 7000 g for 10 minutes. After centrifugation, the supernatant free of cell debris was recovered. This stock was used to produce 500 ml of liquid culture phage: the equivalent of $7.5 \times 10^8$ pfu (plaque-forming units) was added to 500 μl of cells of a culture inoculated overnight with Y1090, and 500 μl of 10 mM $MgCl_2/CaCl_2$. It was incubated at 37° C. for 15 minutes and added to 500 ml of antibiotic-free LB medium. Lysis of the bacteria observed by the appearance of filaments in the culture was followed until lysis was complete (4-5 h). Then the culture was centrifuged at 6000 g for 15 minutes at 4° C., the supernatant was recovered and stored at 4° C. overnight.

The next day, the DNA was purified with the Lambda Maxi Kit™ (Qiagen, Germany) adjusting the start of the protocol with a larger volume of starting supernatant. The final residue was re-suspended in 500 μl of TE buffer.

2.1.4.5. From Parasites

100 μl of culture residue from red blood cells with 10% parasitemia was re-suspended in 100 μl of PBS, pH 7.2 and purified using the Qiaamp DNA Mini Kit™ (Qiagen, Germany). About 5 μg of DNA was obtained from 100 μl of the residue of the 10% parasitic culture.

2.1.5. Purification of Total Parasitic RNA

We used two methods, depending on the desired quantity of RNA. For large quantities, the method described by Kyes et al (2000) was used, while to obtain preparations in more restricted quantities, we used the RNeasy Kit™ (Qiagen, Germany).

2.1.6. RT-PCR

RT-PCR was carried out using the RT-PCR kit of Qiagen (Germany). Specific primers for each gene and situated, if possible, so that it was possible to distinguish between the products from amplification of genomic DNA and RNA (around the introns) were used. A first reverse transcription reaction was carried out at 50° C. for 30 minutes, then a PCR reaction was carried out under the same conditions as those described for PCR of parasitic DNA with selected primers, sometimes followed by a second reaction (nested PCR) with primers located in the sequence for the first amplified PCR product. However, the hybridization temperature varied as a function of the primers used (between 50° C. and 60° C.).

2.1.7. Purification of Histidine Recombinants 2 l of Luria Broth medium supplemented with 100 ng/ml of ampicillin was inoculated with 50 ml of bacterial culture containing the recombinant plasmid. The growth of bacteria was followed by measuring the bacterial turbidity at 600 nm and at the desired optical density (between 0.5 and 1), a concentration of IPTG in the range 0.5 and 1 mM depending on the recombinant was added to the culture and induction lasted between 2 h and 4 h.

The cells were then harvested and the bacterial residue was re-suspended in a buffer of 20 mM of $NaPO_4$, pH 7.4 and 8 M of urea (TU) (25 ml/liter of bacterial culture). The cell suspension then underwent sonication, 10 shocks of 1 minute each, and the supernatant containing the recombinant proteins was recovered by centrifugation at 10000 g for 10 minutes, and filtered at 0.22 μm. An affinity purification step was carried out on a Nickel column. A 1 ml column (HiTrap™, Pharmacia, Sweden) was washed as indicated by the supplier and 1 ml of $NiCl_2$ was applied, followed by others washes. The column was then washed with 5 ml of TU, and the supernatant was applied to the column. A wash with 10 ml of TU was then carried out ant the recombinant eluted with an increasing gradient of imidazole, a competitor for histidine. Depending on the purified recombinant, different concentrations were used, and the results obtained are summarized in the table below. The protein pool was then dialyzed against a pH 6 L-histidine buffer, and chromatographed on an anion exchange column (HiTrapQ™, Pharmacia, Sweden) to eliminate a portion of the Lipo Poly Saccharides (LPS) or endoxins which induce non-specific responses (Morrison and Ryan, 1987).

| Histidine recombinant purification table | | | | | | |
|---|---|---|---|---|---|---|
| Recom- | Induction[1] | | | OD after induc- tion | Protein location, molecular weight[2] | Imidazole (mM)[3] | NaCl (mM)[4] |
| binant | OD | IPTG | Time | | | | |
| 747 | 0.5 | 0.5 | 4 h | 2.7 | Mem, 18 | 50 | 360 |
| 772 | 0.5 | 0.5 | 4 h | 2.2 | SN, 35 | 36 | 120 |

[1]OD measured at 600 nm, the concentration of IPTG (mM); and the induction time before harvest;
[2]After sonication, and centrifugation of a suspension of bacteria containing no urea (8 M) in the buffer, the supernatant and the residue containing the bacterial membrane debris was tested using Western blot to detect where the recombinant protein was located. In the presence of urea all proteins were soluble and the purification procedures were thus applied in the presence of 8 M urea.
[3]The concentration of imidazole at which the protein was eluted on the HiTrap-Ni ™ column.
[4]The concentration of NaCl at which the protein was eluted on the HiTrap-Q ™ column.

2.2. Immunological Techniques 2.2.1. ELISAs (Enzyme Linked ImmunoSorbant Assay)

The optimum conditions were determined with 100 μl of antigen solution at a concentration of 10, 5 or 1 μg/ml coated onto plates in 50 mM of Carbonate, pH 9.6 or 1×PBS, pH 7.4 by incubating plates overnight at 4° C. Saturation was achieved, either in PBS supplemented with 3% of skimmed milk, or 1% of BSA (calf serum albumin) at ambient temperature or at 37° C. for 2 hours. Dilution of serums 100 or 200 times was carried out either with 1.5% PBS/milk, or with 1% PBS/BSA, and incubation was carried out at ambient temperature or at 37° C. for 1 h.

Incubation with secondary antibodies coupled with HRPO (horseradish peroxidase) diluted by 1/2000 in the serum diluting buffer was carried out at ambient temperature, and visualizations were done using TMB buffers (peroxidase substrate and peroxidase solution B) (Kirkegaard and Perry Laboratories, USA) mixed volume for volume immediately prior to use, 100 µl of which was distributed in each well. The blue stained reactions were stopped by adding the same volume of a 1 M solution of phosphoric acid. The reactions were viewed at 450 nm in a Multiscan Ascent™ (Labsystems) reader.

The results with mice are expressed as a Ratio (an arbitrary unit with respect to the level of response in naive controls) and in the experiments in which the number of isotypes were studied, as the ratio of total IgG determined in the same experiment.

2.2.2. Immunopurification of Specific Antibodies

For the immunopurification of specific antibodies against $His_6$ recombinants, a method described by Brahimi et al, (1993) was employed. 100 µl/well of the antigen solution in PBS, pH 7.2, at a concentration of 5 µg/ml was adsorbed onto Nunc Maxisorp™ plates (Nunc, Denmark), and the plates were incubated at +4° C. overnight. The hyperimmune serum was then incubated at a dilution of 1/50 for 1 hour at ambient temperature, the plates were washed and the antibodies were eluted by adding glycine at 0.2 M pH 2.5, incubation for 3 minutes and recovering followed by neutralizing the pH with Tris, 1M, pH 11. Immunopurification from β-galactosidase fusion recombinants was carried out on nitrocellulose filters, as described by Beall and Mitchell, (1986).

2.2.3. SDS-PAGE and Western Blot

Depending on the test samples, gels with different percentages of acrylamide (BioRad™ 29.1:1 ratio) (5, 7.5, 10 or 12%) were used. After migration in a Tris/glycine buffer (pH 8.5) with the minigel kit (Biorad, USA), the gels were either stained with Coomassie blue or underwent transfer to nitrocellulose filters (0.45 µm) in the Trans-Blot™ cell (BioRad).

After transfer, the proteins were viewed by staining with 0.2% of Ponceau red in a solution of acetic acid (5%), then the filter was saturated with TBS/5% skimmed milk for 30 minutes. The human antibodies, immunopurified without dilution, and the serum diluted to 1/100 or 1/200 in TBS/5% milk/0.05% Tween™, were incubated for 1 to 2 hours at ambient temperature. The filter was then washed 3 times for 10 minutes in TBS/0.05% Tween™ and incubated with antiserums coupled with alkaline phosphatase diluted to 1/5000 for 30 minutes. After washing in the same buffer, color reactions were produced by adding NBT (330 µg/ml) and BCIP (165 µg/ml) (Promega, Germany) diluted in Tris buffer, pH 9.

2.2.4. IFI (Indirect ImmunoFluorescence)

All incubations at 37° C. were carried out in a moist chamber to avoid drying out the tissues or cells to be studied. The buffers were filtered with a 0.22 µm filter to prevent contamination by other microorganisms and background noise.

2.2.4.1. Sporozoite Stage

After dissection of the salivary glands of mosquitoes infected with the parasite, the sporozoites were fixed with 0.01% of glutaraldehyde in PBS and washed carefully with PBS.

In order to study labeling only on the sporozoite surface, Galey et al, (1990) developed a technique for "wet" fixation with a suspension of sporozoites attached to polylysin. The titration slides (Polylabo, France) were coated with 1 µl of 50 mg/ml polylysin solution then left to dry overnight at 37° C. 1 µl of a suspension of sporozoites (20/µl) was deposited on each well and incubated overnight in a moist chamber at 4° C. Intra-parasitic detection was carried out by fixation of the sporozoites in acetone.

2.2.4.2. Hepatic Stage

Sections fixed with Carnoy's fixative and paraffined were prepared by 3 baths of xylene each for 10 minutes, 3 baths of absolute alcohol, each of 5 min, 2 baths of distilled water, each of 5 minutes, and dried in the open air. The sections were then rehydrated for 10 minutes in filtered PBS, pH 7.4. Sections for freezing were fixed in acetone for 10 minutes.

2.2.4.3. Blood Stage

Blood slides were fixed in acetone for 10 minutes and compartments for each test sample were defined by drawing edges with a Pentel red label on the smear.

The remainder of the technique was identical for each of the three stages: after fixing, the test antibodies (diluted in PBS) were deposited into each well, cup or compartment, and the slide was incubated at 37° C. in a moist chamber for 1 hour. The slides were washed 3 times for 10 minutes in 1×PBS, then incubated with an anti-human or mouse anti-IgG (depending on the specific antibodies used), coupled with fluorescein (Alexis) diluted by 1/200 in PBS and 1/50000 Evans blue, incubated for 30 minutes at 37° C. in a moist chamber, washed three times in 1×PBS, and covered with a slide after one drop of glycerin buffer (PBS, 30% glycerol) had been deposited. The slide was observed under a UV microscope (Olympus™ BH2).

2.2.5. Mouse Immunizations 2.2.5.1. With Recombinant Histidines

Protocols a, b and c were essentially employed to obtain specific serums, while protocols b, c and d were used to carry out challenge infections with *P. yoelii*.

a) IFA/Alum Adjuvant

Female 6-week old BALB/c mice received a first intraperitoneal injection of 500 µl with a mixture of 20 µg of antigen ($His_6$-249, $His_6$-680, $His_6$-747, $His_6$-772), 2 mg/ml of alum ($Al(OH)_3$), and incomplete Freund's adjuvant (AIF), volume for volume, supplemented with 0.9% NaCl.

The two subsequent injections, each at fortnightly intervals, were carried out with the same quantity of antigen in the same volume, but without AIF, and with methiolate, a preservative, in an amount of 0.05%.

The mice were sampled (500 µl) 2 weeks before immunization, 1 month and 6 weeks after the first immunization, onto EDTA and the plasma was recovered and stored at −20° C.

b) CFA

Female 6 week old BALB/c mice received 3 subcutaneous injections every fortnight at the base of the tail of a mixture constituted by 100 µl of complete Freund's adjuvant and 10 µg of antigen ($His_6$-114 or $His_6$-662) in 100 µl of PBS. 1 week after the third injection, mouse serum was removed and the responses were tested using ELISA against the recombinant and using IFI on the sporozoites. 18 days after the final injection, the mice were subjected to a challenge infection with *P. yoelii* sporozoites.

c) SBAS$_2$ (Smith and Klein Beecham Adjuvant)

Female 7 week old C3H mice received three subcutaneous injections at the base of the tail of 100 µl of a mixture constituted by 57 µl of adjuvant mixed with 43 µl of antigen (His$_6$-249, His$_6$-747 or His$_6$-772) corresponding to 10 µg, the injections being separated by 3 weeks each time. 10 days after the last immunization, the mice were sampled and the corresponding serum was harvested.

d) Microparticles

The antigen solutions (His$_6$-249, His$_6$-747 or His$_6$-772) was adsorbed onto polystyrene microparticles 0.5 µm in diameter (Polysciences Inc, USA) by incubation at 37° C. with agitation for 4 hours in a glycine solution, pH 8.0. Adsorption of the antigen was verified by the capacity of the microbeads to agglutinate with a serum specific to the adsorbed antigen. Female 7 week old C3H mice received three subcutaneous injections at the base of the tail of 100 µl of a mixture constituted by microbeads coated with the antigen corresponding to 10 µg, the injections being separated by 3 weeks each time. 10 days after the final immunization, the mice were sampled and the corresponding serum was harvested.

2.2.5.2. With Recombinant DNA 6 week old BALB/c and C3H mice were injected three times at 8 week intervals intramuscularly with 100 µl of antigen (pNAK114, pNAK249, pNAK438, pNAK571, pNAK747, pNAK772) in PBS, pH 7.4, then a fourth time 12 weeks after the third injection. Blood was sampled 1 week after the third and fourth immunization onto EDTA, and the serum was harvested after incubation of the sample overnight at 4° C.

The spleens from 3 mice/group were removed after the fourth immunization and the cell response stimulation was studied. After a fifth booster, 8 weeks after the fourth injection, the mice underwent a challenge infection with *P. yoelii* sporozoites.

2.2.6. Challenge Infection with Sporozoites and Blood Stage

Sporozoites from *Anopheles stephensii* mosquitoes infected with the 1.1 clone from *P. yoelii yoelii* were obtained by a method (Ozaki et al, 1984) consisting of isolating the thoracic cage of the mosquito and obtaining sporozoites by centrifugation through glass wool, which sporozoites were then washed by successive re-suspension in PBS after centrifugation.

The mice were infected with *P. yoelii* sporozoites retroorbitally with 150 to 200 sporozoites (200 µl/injection) and parasitemia was monitored by smears on day 3 following infection until the 12$^{th}$ post-infection day, both in immunized animals and in naïve mice infected with the same batch of sporozoites.

Blood stages removed from other mice infected with *P. yoelii* were washed with PBS and the equivalent of $5 \times 10^4$ parasites was injected intraperitoneally.

2.2.7. Study of Cell Responses

To study both the induction of specific T cells proliferation and the secretion of cytokines capable of stimulating the immune response, we studied the stimulation of mouse splenocytes by antigens and the secretion of IFN-γ by these cells.

2.2.7.1 Proliferation of T Lymphocytes

The spleens were removed from mices; suspensions of splenocytes were washed twice in RPMI 1640™ (Gibco, France) and the cells were re-suspended to a final concentration of $5 \times 10^6$ cells/ml in RPMI supplemented with 100 U/ml of penicillin, 2 mM of L-glutamine, 10 mM Hepes, 50 µM β-mercaptoethanol, 1.5% of foetal calf serum (FCS) and 0.5% of normal mouse serum. 100 µl/well of each suspension was distributed into 96-well round bottom plates (Costar, USA) and the recombinant proteins to be tested were added in a concentration of 50 mg/ml. These tests were carried out in triplicate. After 48 hours of incubation (37° C. with 5% CO$_2$), 50 µl/well of culture supernatant was removed and stored at −70° C. before determining the IFN-γ titer. 50 µl/well of supernatant was removed to assay the cytokines. In order to detect DNA replication due to stimulation of division, 50 µl of a solution of tritiated thymidine ($^3$H) (Amersham Life Science, England) at 1 µCi/well was added during the last 12 hours of incubation. The cells were harvested in an automatic cell harvester (Skatron Inc, Sterling, Va., USA), and incorporation of $^3$H Thymidine quantified by scintillation. The results were expressed as the Stimulation Index (SI) and the proliferation was considered to be positive when the S.I. was above 2.

2.2.7.2 Detection of γ Interferon (IFN-γ) Secretion

The titers of IFN-γ in culture supernatants were determined using a sandwich ELISA method. Maxisorp™ plates (Nunc, Denmark) with flat bottoms were coated with a rat monoclonal antibody anti-primary mouse-IFN-γ (R4-6A2) (Pharmingen, San Diego, Calif.) diluted in a 0.1 M carbonate buffer, pH 9.6, and left overnight at 4° C. Between each step of the procedure, the plates were washed several times with PBS buffer supplemented with 0.05% Tween™ (PBS-T). The plates were then saturated with 3% bovine serum albumin (BSA, Sigma Chemicals, St Louis, USA) in PBS-T. Non-diluted supernatants were added to the wells and the plates were incubated overnight at 4° C., followed by incubation for 1 h at ambient temperature with a secondary biotinylated rat anti-mouse IFN-γ monoclonal antibody (XMG1.2™, Pharmingen, San Diego, Calif.) diluted in PBS-T. The steps for labeling with antibodies coupled with peroxidase were identical to those used in the ELISA technique (A.2.1).

2.2.7.3. Detection of Cells Secreting IFN-γ by Elispot

The number of cells secreting IFN-γ was determined in non stimulated splenocytes 40 hours after being freshly isolated and incubated with antigens. Microtitrating plates (Multiscreen-HA™ sterile plate, Millipore) were coated with 50 µl of a solution containing 5 µg/ml of anti-IFN-γ antibody (18181D™, Becton Dickinson Co). After incubating overnight at 4° C., the wells were washed and saturated with a 5% FCS solution. Suspensions of cells at $5 \times 10^5$ cells/well were incubated with the antigen in an amount of 50 µg/ml in a total volume of 200 µl for 40 h at 37° C. in a moist atmosphere with 5% CO$_2$. The plates were then washed three times with PBS-T and three times with PBS alone and the wells were then coated with 50 µl of biotinylated anti-mouse IFN-γ antibody solution (Becton Dickinson Co, USA) diluted to 1/200 and incubated overnight at 4° C. The plates were then washed in the same manner as before, before adding 50 µl per well of alkaline phosphatase coupled with streptavidin (Boehringer-Mannheim, Germany) in a dilution of 1/2000 in PBS. After incubating for 1 h, and washing the plates, spots were detected by developing a colored reaction with BCIP/NBT reagents at 50 µg/ml in the region in which individual cells had secreted IFN-γ. The results are expressed as the number of cells forming spots with respect to $5 \times 10^6$ splenocytes.

2.2.8. Serums and Cells 2.2.8.1. From Individuals Naturally Exposed to the Parasite 10 serums from adults living in a highly endemic zone (Ivory Coast) and naturally protected were employed in ELISA studies and immunopurifications of antibodies specific to the antigens being studied.

Serum from individuals in two age ranges of 0-9 years or over 12 years were selected from Ndiop and Dielmo villages (Rogier and Trape, 1995; Trape et al, 1994). Ndiop is located in an endemic zone which records about 20 infectious bites/year, and Dielmo, in a zone which records 150 infectious bites/year. Each serum in one of the two regions corresponded in age and sex to a serum from the other region.

2.2.8.2. From Animals or Humans Immunized with Irradiated Sporozoites

Two chimpanzees were immunized either with sporozoites irradiated at 18 kRad, or at 30 kRad by 4 injections each of $5 \times 10^6$ sporozoites, intravenously. The first 3 immunizations were carried out at 1 month intervals, while the $4^{th}$ was carried out 4 months after the third. Their serum and peripheral blood cells were studied in cell response tests and humoral response tests after 3 immunizations. The two animals were infected by intravenous injection of $4 \times 10^4$ sporozoites (low dose) each of *Plasmodium falciparum* and only the chimpanzee immunized with 18 kRad irradiated sporozoites was protected (did not develop blood parasitemia).

Two human volunteers immunized by the same means received a booster with a new batch of irradiated sporozoites, and peripheral blood cells were studied in Elispot tests. Further, the serum from 4 human volunteers immunized with irradiated sporozoites was also at the disposal of the Applicant.

2.2.8.3. From Individuals Exposed Differentially to the Parasite

We had at our disposal serum from 8 individuals naturally exposed to the parasite but under permanent chloroquine treatment, which eliminated the blood stages at a very early form and the serum from 5 individuals accidentally infected by transfusion of blood infected with *Plasmodium falciparum*.

3) Results 3.0: Example 1

Identification of Two Novel Antigens DG47 and DG772 from *Plasmodium falciparum* Recognized by Volunteers Immunized with Irradiated Sporozoites The DG747 and DG772 clones were selected not simply because of the initial criteria imposed (detection on sporozoites and the hepatic stage, and recognition by hyperimmune serum), but because several supplementary characteristics interested us: DG747 had no cross reactivity with other proteins from the PM library, and DG772 had only one cross reactivity, with LSA-1, the only antigen identified as being expressed only at the hepatic stage of *Plasmodium falciparum*. Further, specific antibodies for the two proteins labeled *P. yoelii* sporozoites.

An initial sequencing revealed that these two clones contained inserts belonging to genes that were unknown until now, but the sequence of which was available on databases for the *Plasmodium falciparum* genome. We thus decided to work on the molecular characterization of stage expression, gene conservation, and an immunological characterization (antigenicity, immunogenicity) of these novel antigens. The results show that a) these two antigens induced an immune response in individuals or animals exposed only to the pre-erythrocytic stages both artificially (by immunization) and naturally (on the ground); b) they are recognized by serum from individuals naturally exposed to the entire life cycle of the parasite, both in zones of weak and of highly endemic nature. Further, we have evaluated in the mouse their immunogenic potential and protective potential by immunization and challenge infection by *P. yoelii*.

3.1. Sequence Analysis

DG747 codes for a 59 amino acid polypeptide the 40 C-terminal amino acids (aa) of which form part of a repetitive structure of 5×8 aa rich in arginine and lysine. This sequence is identical to aa 81-140 of the PfB0155c gene (1524 bp, 508 aa) located on chromosome 2 (FIG. 3.1*a*). This gene, which codes for a putative protein (Gardner et al, 1999) comprises neither the predicted introns nor signal peptides, nor regions homologous with other proteins from *Plasmodium* or other organisms. The corresponding protein has a theoretical molecular mass of 59 kDa, and a neutral isoelectric point (Ip) (7.5), but certain regions have highly variable Ip, for example the region found in DG747 has a positive charge at neutral pH.

DG772 contains a 333 bp insert, which are translated into 111 aa contained in an open reading frame. This polypeptide corresponds to the region of 1146-1256 aa of a protein with 1493 amino acids coded by a gene located on chromosome 1 (FIG. 3.1*b*). The theoretical mass of the protein is 173 kDa and the isoelectric point is 5.05. The protein is mainly constituted by polar amino acids and does not contain hydrophobic sites, at least in the N-terminal portion, where it may have a GPI anchoring site. The gene contains no repetitions and the translated nucleotide sequence has a great homology with proteins of the "EBP" family (Adams et al, 1992), i.e. with the 5'cys and 3'cys regions which are characteristic of this family.

3.2. Stage Expression and Gene Conservation

In order to evaluate stage expression of the two proteins more precisely, we used IFI and Western Blot techniques on different stages of *Plasmodium falciparum* and on murine parasites *P. yoelii* and *P. berghei*.

The surface of *Plasmodium falciparum* sporozoites was labeled with antibodies (human or mouse) specific to DG747 and DG772, but the erythrocytic stages were labeled differently for the two groups of antibodies. The anti-His$_6$-747 (anti-747) antibodies labeled the young stages but little, and labeled the mature schizont stages strongly, with localized labeling around the knob structures (FIG. 3.2 image A), while the anti-His$_6$-772 (anti-772) antibodies labeled the parasite in a more homogeneous manner throughout the erythrocytic stage. In the murine species *P. yoelii* and *P. berghei*, the surface of the sporozoites was strongly labeled by the specific antibodies of the two antigens.

In order to define the size of the detected proteins, we also carried out Western Blot on protein extracts from blood parasites of *Plasmodium falciparum* with the same antibodies (FIGS. 3.3*a* and *b*).

The anti-747 antibodies labeled a polypeptide of about 70 kDa both in ring extracts and in schizont extracts, while no band was detected in non parasitic erythrocytes. The polypeptide detected by anti-772 antibodies was larger, with a molecular mass of 150 kDa, and was detected both in the rings and in the schizonts. Labeling of the protein extracts from *P. yoelii* detected a 70 kDa polypeptide for the anti-747 antibodies in the sporozoites and the blood stages and a 60 kDa polypeptide for the anti-772 antibodies, only detected in *P. yoelii* sporozoites.

Further, to confirm the presence of proteins and their constancy of expression on the sporozoite surface deriving from several different parasites, we examined, by IFI, batches of sporozoites deriving from different Thai isolates of *Plasmodium falciparum*. The anti-772 serum had labeled all sporozoites, while only 7 out of 10 of the test isolates were labeled with anti-747. Similarly, PCR amplifications with primers specific for the two gene fragments (indicated in FIGS. 3.1a and 3.1b) were carried out with DNA from the blood stages of 12 different strains of *Plasmodium falciparum* (FIG. 3.4). The PCR products corresponding to DG772 were amplified from 12 samples and their size was similar, while primers specific for DG747 could only amplify a fragment from 9 of the 12 DNAs. It should be pointed out that all of the parasite lines used in this study (T9-96, NF54 and 3D7) contain the corresponding genes. These results indicate a variation in the level of expression or the presence of DG747 in parasitic strains, as in total only 15 out of 22 parasites appeared to contain the DG747 gene or showed a positive reaction in IFI.

3.3. Recognition by the Human Immune System in Endemic Zones

In addition to the study regarding the constancy of expression of the antigen, we studied the prevalence of humoral responses of individuals living in highly (Dielmo) or weakly (Ndiop) endemic zones, and in two groups of different ages in these two zones (FIGS. 3.5a and 3.5b).

We observed the same prevalence (40%) against 747 in the weakly endemic zone, except that the number of individuals who responded strongly (intensity of response compared with controls) increased with age. In the highly endemic zone, the number of those responding against 747 increased with age, as well as the intensity of the response, and the prevalence in adults, who can be considered to have acquired immunity, was 85%. Further, these responses appear to correlate with exposure to the sporozoite, as the antibody count is higher in individuals of a given age group in a stronger transmission zone. However, in a similar zone, the response did not change significantly during low transmission seasons (dry season) (results not shown) which could correspond to the response against the blood stages and/or indicate that the anti-747 immune response is long-term. The response induced by DG747 increased in prevalence and intensity as a function of exposure and the duration of exposure to the parasite (age).

The anti-772 response increased like anti-747 as a function of age, but with a much lower increase compared with the degree of transmission observed between Ndiop and Dielmo and compared with age. The degree of anti-772 responses, measured as a % prevalence and intensity, was higher for young individuals than for anti-747 responses, but lower in strength (75%) than the anti-747 (85%) in Dielmo in immune individuals.

3.4. Comparison of Responses Induced by Different Stages of the Parasite

We had the advantage of being in possession of cells from individuals immunized with irradiated sporozoites, and serum from persons exposed to the parasitic infection in different manners.

3.4.1 Cell Responses

All of the studies were carried out in close collaboration with Jean-Pierre Sauzet in the laboratory. Because of the small amount of material available, we restricted our analyses in order to detect what we had previously defined as one of the important criteria (role in protection) to evaluate a vaccinal potential in the pre-erythrocytic stage. We studied the secretion of IFN-γ from cells from 2 individuals immunized with irradiated sporozoites of *Plasmodium falciparum*, as we have observed, when analyzing other antigens, in particular LSA3 (a vaccine candidate studied in our laboratory (Daubersies et al, 2000)), that the degree of secretion of this cytokine appears to be correlated with protection. In these two volunteers, the number of cells secreting IFN-γ against DG747 and DG772 was as high as with recombinants from LSA3 (729 and PC), (FIG. 3.6a). Further, we have examined whether the immune cell responses measured by proliferation of T lymphocytes and secretion of IFN-γ differed between two chimpanzees immunized with sporozoites irradiated of *Plasmodium falciparum*, but one of which was not protected (FIG. 3.6b).

Cells from the immune system of the animal immunized with viable irradiated sporozoites (18 kRad) and subsequently protected, recognized antigens DG747 and DG772, as did cells from the animal immunized with non-viable irradiated sporozoites (30 kRad), and not protected during a challenge infection.

Lymphocyte proliferation was at the limit of the threshold value, while the degree of secretion of IFN-γ was high, both for the quantity of cytokine detected and for the number of secreting cells (detected by Elispot). This was the case both for effectively immunized animals and for those which were not protected. However, it appears that the response levels were greater for animals immunized with sporozoites irradiated at 30 kRad. The responses induced by 747 were stronger than those induced by 772, and both were stronger than those induced by LSA3.

Cells removed from animals that have undergone supplemental immunization by irradiated sporozoites were damaged during transport from the primatology center in Africa, and thus we could not study the presence of a "boost" induced against said antigens.

3.4.2. Study of Humoral Responses

We were not in possession of cells from all human groups exposed in a different manner to parasitic infection, but we could study in detail the humoral response (IgG isotypes) from volunteers immunized with irradiated sporozoites (ISS, only exposed to pre-erythrocytic stages), from naturally immune individuals living in a highly endemic zone (exposed to all stages of the parasite), and from an individual having accidentally been infected with malaria by blood transfusion (only exposed to blood stages) (FIGS. 3.7a and 3.7b).

For the two antigens, the biggest difference was observed for the cytophilic isotype IgG1 the amount of which was much higher in serum from immune individuals (SHI) than in serum from a patient infected by transfusion or ISS volunteers. The responses from these two last groups were fairly similar and did not bring about an imbalance between cytophilic antibodies (IgG1 and IgG3) and non cytophilic antibodies (IgG2 and IgG4). We also noted that the serum from an individual exposed for a long time to the parasite, but under permanent prophylaxis (PM), has the same profile of isotypes as the ISS.

3.5. Immunogenicity in the Mouse

Mice from two different strains were immunized with recombinants in the form of proteins, with different adjuvants or in the form of "naked" DNA constructions, without adjuvant.

A preliminary study with the naked DNA construction comprising no signal sequence allowing export of the synthesized protein was carried out. The immunized mice generated no humoral response, whether for the two antigens of for other study simultaneously. However, we detected specific anti-747 and anti-772 cell responses. Both T lymphocyte proliferation and the degree of IFN-γ secretion were tested for the two mouse strains, C3H and BALB/c. The response profiles are shown in Tables 3.1a and 3.1b which show that for the case of cell responses from mice immunized with pNAK747, there was both proliferation and IFN-γ secretion stimulation, while for pNAK772, T cell proliferation was only slightly stimulated compared with stimulation of IFN-γ secretion which was considerable. Among all immunized mice, the highest level of IFN-γ secretion was observed when the level of proliferation stimulation was lowest.

Vaccinations with other formulations (recombinant protein and naked DNA with a signal sequence) have both induced a humoral response in the mice (FIG. 3.8). All of the serum from said immunized mice recognized the native protein in IFI tests and the labeling corresponded with that observed for immunopurified human antibodies.

The anti-747 responses have a similar profile for all immunized mice and all of the formulations used, with an isotype response with IgG2b preponderance. The anti-772 responses were also similar between the mouse and vaccine formulations, but with a clear predominance of IgG1. The isotype profile thus depends on the immunogen rather than on the mode of presentation employed. However, the end point titers were much higher when we immunized with recombinant proteins (1/200000) compared with DNA (1/2000), and the titers from the serum of mice immunized with $His_6$-772, were higher than those with $His_6$-747.

Since we observed a cross reactivity with the sporozoite stage of *P. yoelii*, we tested the protective potential of these antigens by infecting mice immunized with recombinant proteins with sporozoites from that species. Parasitemia was monitored by observation of the blood forms on smears from day 3 of the infection and for 12 consecutive days. We observed no protection regardless of the mouse strain employed, as parasitemia was detected on the same day as that for non immunized mice, and the graph was similar to that for control mice (results not shown).

3.6. Supplemental Data 3.6.1. DG772

Using RT-PCR on the total RNA from sporozoites and blood parasites, the inventors could determine the splicing sites for the messenger RNA corresponding to the coding gene. The primer sequence was extracted from the genome data of *Plasmodium falciparum*.

The amplification products had identical sizes in the sporozoite stages and in the blood stages, and differed from the size of the product obtained by amplification of genomic DNA, and sequencing the splicing sites showed that they were identical (see the introns indicated in the Figure).

The gene coding for DG772 belonged to a family of proteins identified by a shared motif. All the proteins from the EBP (Erythrocyte Binding Proteins) family share conserved motifs from cysteine residues the arrangement of which is similar for all the proteins. However, the degree of identity does not exceed 31% (max 57% homology), even in the most highly conserved regions.

3.6.2. Immunogenicity Tests Envisaged in Humans

From our results obtained in mice, we can confirm that the antigens DG747 and DG772, employed both in the form of DNA and in the form of recombinant protein, are immunogenic. Further, because the recombinant proteins are recognized by immunized individuals and protected against infection by *Plasmodium falciparum* sporozoites, it indicates a role for those antigens in pre-erythrocytic immunity. A test in primates and in particular in chimpanzees could allow the optimum formulation for clinical tests in human beings to be selected.

In phase I trials, to study the immunogenicity and safety of the product, we envisage three formulations, all prepared under GMP conditions: 1) the antigen in the form of a recombinant protein purified from the *Lactococcuc lactis* bacterium (use permitted in humans) supplemented with SBAS2 (GSK) adjuvant; 2) the DNA construct in the Vical™ vector (Avantis Pasteur); and 3) synthetic lipopeptides injected without any adjuvant (see LSA3). Those formulations would be distributed by subcutaneous injection (into the deltoid). Our preliminary tests show that the antigens $His_6$-747 and $His_6$-772 induce cell responses and humoral responses in individuals who have only been exposed to the pre-erythrocytic stages. We would then study the cell responses and humoral responses in individuals immunized by the selected formulations by comparing them with those observed in individuals immunized with sporozoites attenuated by irradiation and protected against a challenge infection by non-attenuated sporozoites. Depending on those responses, a challenge infection with *Plasmodium falciparum* sporozoites would be envisaged.

3.6.3. Homology with Other Nucleotide Sequences

Southern blot hybridization under stringent standard conditions (0.1×SSC, 60° C.) only gave rise to hybridization with the corresponding gene.

3.6.4. Identification of Homology Using Bioinformatics Means

Research was carried out using BLAST™ software (tblastx and blastn) using all available databases for the *Plasmodium falciparum* genome and databases for other organisms. The parameters were the default parameters found at ncbi.nlm.nih.gov/BLAST/.

3.7. Discussion

This work, which forms part of a study of antigens expressed in the pre-erythrocytic stages, allowed us to provide an initial characterization and evaluation of the vaccine potential of two novel *Plasmodium falciparum* antigens. These two antigens have different characteristics on the molecular level. Firstly, the protein of which DG747 forms a part contains repeats, while the molecule containing DG772 has not direct repeat. The Pfb0155c gene coding for DG747 is small (1524 bp) and contains a repeat region to which DG747 belongs. We could not detect the presence of the gene by PCR in all strains, nor observe reactivity with all of the sporozoite strains studied. The observed absence could be due to a genuine gene deletion or to the experimental procedures. One of the primers used to detect the portion coding for DG747 crosses the repeat portion, which could cause difficulties in amplifying a gene containing a larger repeat, or in detecting a gene containing fewer repeats. Further, this is also the case when using indirect immunofluorescence detection, or any number of variations in the repeats may change the affinity of the specific antibodies, if the target epitope crosses that region. The expression detected by IFI appears to be present throughout the asexual parasitic cycle in the vertebrate host (we have not analyzed the sexual stages). Despite the presence of repeats in DG747, we have not detected cross reactivity with other *Plasmodium falciparum* antigens. The entire gene sequence was not homologous with other plasmodial proteins identified up to now, and we also had no indications of any biological function.

DG772 contains no repeats and its presence appears to be constant, whether detected by PCR or by IFI. On the biological level, the gene coding for DG772 appears to be interesting. We have found, by sequence homology, that this gene of 5300 bp with an open reading frame forms part of the EBP (Erythrocytic Binding Protein) family (Adams et al, 1992), but the sequence of DG772 does not belong to the conserved regions of that family; it shares only a small portion of sequences with the N-terminal end of the 3'cys region. Further, there are no cross reactivities nor sequence homologies with DG249, a further clone forming part of one of the consensus portions of the gene coding for EBA-175. It may be that DG772 forms part of a region that confers particularity on each molecule of this family. The presence of two molecules from the EBP family (EBA-175 and 772) on sporozoites could imply that several molecules of this family exist could be alternatively involved in the invasion process as described in the blood stages.

A knowledge of prevalence is useful when evaluating a vaccine candidate, and the prevalences obtained for DG747 and DG772, 85% and 75%, are high. This study has shown the high antigenicity of a small portion of two molecules, and has suggested that it would be interesting to study other epitopes from the same molecule in more detail. The humoral response detected against DG747 and DG772 in permanently exposed individuals indicates that there is a preponderance of the IgG1 response (cytophilic type) developed during sustained exposure which is not found in the case of transfusional malaria. In contrast, profiles of humoral responses obtained for two groups exposed to the pre-erythrocytic stages of shorter or longer duration (PM and ISS) are similar and the IgG1 level is low, which indicates that this isotype results from repeated exposure to the antigen in the blood stages. A study of cell responses in these same zones should be carried out to obtain a more precise idea of the immune responses induced by those antigens.

At the pre-erythrocytic stages, we observed an induction of the cell response by these antigens both in chimpanzees and in humans. We have observed the secretion of IFN-γ, described as a factor involved in protection against pre-erythrocytic stages. The difference in response observed in chimpanzees as a function of the irradiation dose could mean that the antigens are recognized both on sporozoites and in the hepatic stages. Sporozoites irradiated at 30 kRad are incapable of penetrating into the hepatocyte, and the detected responses are thus only due to that exposure, while sporozoites irradiated at 18 kRad develop in the hepatocyte, and the detected responses are thus due to this stage. It would be interesting to study more closely the responses induced in these two animals (MHC1 restriction), and the response "boost" induced during several successive immunizations. This work has also shown that in these two antigen fragments, T epitopes and B epitopes both exist.

The immunogenicity induced by the two antigens in the mouse is different, with an IgG1 predominance for DG772, which is not observed for DG747. In contrast, we have not observed any differences in response as a function of formulations, which is interesting as the presentation of the molecules is not identical for each formulation. The cell responses obtained only for the formulation that did not induce detectable humoral responses shows that there was both lymphocyte proliferation and IFNγ secretion, dependent on the mouse.

TABLE D1

Summary of pre-erythrocytic malaria antigens known at the present day*

| Antigen | References[1] | Expression stages[2] | | | | Location[3] | Structures | |
|---|---|---|---|---|---|---|---|---|
| | | S | H | SSA | SSS | | Intron | Reps |
| CS | Nardin et al 1982 | + | j | − | − | CHR3 | + | + |
| LSA1 | Guerin-Marchand et al 1987 | + | j, m | − | − | CHR4 | − | + |
| TRAP | Robson et al 1988 | + | j, m | m | − | CHR13 | − | + |
| PfHsp70 | Renia et al 1990 | + | j, m | j, m | − | CHR13 | | + |
| STARP | Fidock et al 1994 | + | j, m | − | − | CHR12 | + | + |
| EXP-1 | Koenen et al 1984 Sanchez et al 1994 | − | m | j, m | Nt | CHR12 | − | + |
| Pfs16 | Bruce et al 1990 | + | nt | − | + | ? | − | − |
| SALSA | Bottius et al 1996 | + | j, m | − | − | CHR2 | + | − |
| LSA3 | Daubersies et al 2000 | + | j, m | − | − | CHR2 | + | + |
| PfEMP3 | Pasloske et al 1993 Gruner et al 2001 | + | j, m | j, m | − | CHR2 | + | + |
| GLURP | Borre et al 1991 | + | m | j, m | Nt | CHR10 | − | + |
| EBA-175 | Camus and Hadley, 1985 | + | j, m | j, m | − | CHR4, 13 ? | + | − |
| DG747 | | | j, m | j, m | − | CHR2 | ? | + |
| DG772 | | | j, m | j, m | − | CHR1 | + | − |

*The antigens shaded in gray are the antigens characterized in the present application.
NT: not tested
[1]The presence of other antigens (MSP-1) in the pre-erythrocytic stages has also been suggested, but the preliminary results still have to be confirmed. The underscored references indicate the year in which pre-erythrocytic expression was discovered.
[2]S: sporozoite; H: hepatic stage, young and mature; SSA: asexual blood stage, young and mature; SSS sexual blood stage. 3. ST: sub-telomeric. The bold characters indicate the form of the stage in which labeling is the most intense.
[3]The majority of chromosomal location detection was carried out by homology identification using databases.

TABLE 3.1a

Stimulation of cell proliferation and secretion of IFN-γ by
His$_6$-747 after 3 immunizations with pNAK747

| Mouse strain | Lymphocyte proliferation stimulation index | | Gamma interferon IU/ml | |
|---|---|---|---|---|
| | His$_6$-747 | pGEX-NN | His$_6$-747 | pGEX-NN |
| C3H | 8.6 ± 3.0 | 3.2 ± 1.1 | 7.0 ± 0.4 | 4.0 ± 0.9 |
| C3H | 23.6 ± 5.9 | 8.8 ± 2.9 | 7.0 ± 0.7 | 4.0 ± 0.2 |
| C3H | 3.0 ± 0.9 | 1.1 ± 0.1 | 16.0 ± 1.9 | 1.0 ± 2.1 |
| Positive | 2/3 | — | 1/3 | — |
| BALB/c | 2.7 ± 0.2 | 1.3 ± 0.2 | 40.0 ± 5.0 | 24.0 ± 3.0 |
| BALB/c | 23.6 ± 4.3 | 3.0 ± 0.3 | 15.0 ± 4.4 | 8.0 ± 1.8 |
| BALB/c | 33.7 ± 7.2 | 5.9 ± 0.3 | 16.0 ± 1.5 | 10.0 ± 4.2 |
| Positive | 2/3 | — | 3/3 | — | pGEX-NN: *Plasmodium falciparum* antigen, not cross-reactive with His$_6$-747.
Positive results are shown in bold.

TABLE 3.1b

Stimulation of cell proliferation and secretion of IFN-γ by
His$_6$-772 after 3 immunizations with pNAK772

| Mouse strain | Lymphocyte proliferation stimulation index | | Gamma interferon IU/ml | |
|---|---|---|---|---|
| | His$_6$-772 | pGEX-NN | His$_6$-772 | pGEX-NN |
| C3H | 0.9 ± 0.1 | 0.7 ± 0.1 | 23.9 ± 2.0 | 10.7 ± 2.9 |
| C3H | 0.9 ± 0.2 | 0.6 ± 0.1 | 1.7 ± 2.0 | 3.3 ± 2.1 |
| C3H | 0.8 ± 0.2 | 0.9 ± 0.2 | 6.6 ± 0.1 | 5.8 ± 2.6 |
| Positive | 0/3 | — | 1/3 | — |
| BALB/c | 3.5 ± 0.3 | 2.7 ± 0.4 | 24.0 ± 2.2 | 10.8 ± 3.0 |
| BALB/c | 1.9 ± 0.3 | 1.2 ± 0.4 | 31.3 ± 7.1 | 5.6 ± 0.9 |
| BALB/c | 3.2 ± 0.9 | 1.5 ± 0.2 | 25.0 ± 12.1 | 6.9 ± 1.5 |
| Positive | 1/3 | — | 3/3 | — | pGEX-NN: *Plasmodium falciparum* antigen, not cross-reactive with His$_6$-772.
Positive results are shown in bold.

TABLE 4.1

Cell responses in mice after 5 immunizations with pNAK438*

| Mouse | Proliferation (IS) | IFN-γ secretion | Antibodies |
|---|---|---|---|
| C3H | 2.3 ± 0.3 | 2.2 ± 2.0 | — |
| C3H | 1.8 ± 1.1 | 15.6 ± 4.0 | — |
| C3H | 3.2 ± 1.3 | 0.5 ± 0.2 | — |
| Positive | 2/3 | 1/3 | — |
| BALB/c | 4.3 ± 1.6 | 26.2 ± 6.3 | — |
| BALB/c | 5.3 ± 0.6 | 29.3 ± 8.5 | — |
| BALB/c | 15.3 ± 2.2 | 12.7 ± 8.7 | — |
| Positive | 3/3 | 3/3 | — |

*The level of responses is shown with respect to the responses obtained by a threshold value. The threshold value was calculated by taking the mean of the responses of non-immunized animals and that of animals immunized against a non-relevant antigen such as OspC, a protein from *Borrelia burgdorferi*.

TABLE 4.2

Detection of expression by IFI with immunopurified human
antibodies or specific anti-His$_6$-680 mouse serum

| Parasites* | a-His$_6$-680 mouse or human |
|---|---|
| *Plasmodium falciparum* NF54 sporozoites | ++ |
| *P. yoelii* clone 1.1 sporozoites | ++ |
| *Plasmodium falciparum* hepatic stage | ++ |
| Blood stage T23 rings/schizonts | ++/+++ (75%) |
| NF54 blood stage rings/schizonts | ++/+++ (75%) |

*Plasmodium falciparum* sporozoites from NF54 strain.
T23: strain of Thai provenance;
NF54: strain of African origin.

TABLE 5.1

Cross reactivities detected in Western blots
between members of the Pf11-1 family

| | P43 | P263 | P322 | P453 | P525 | P563 | P571 |
|---|---|---|---|---|---|---|---|
| E43 | ■ | ■ | ■ | ■ | ■ | ■ | ■ |
| E263 | ■ | ■ | ■ | ■ | ■ | ■ | ■ |
| E322 | ■ | ■ | ■ | ■ | ■ | ■ | ■ |
| E453 | ■ | ■ | ■ | ■ | ■ | ▒ | ■ |
| E525 | ■ | ■ | ■ | ■ | ■ | ■ | ■ |
| E563 | ■ | ■ | ■ | ▒ | ■ | ■ | ■ |
| E571 | ▒ | ▒ | ▒ | ▒ | ▒ | ▒ | ■ |
| E676f | ▒ | ▒ | ▒ | ▒ | ▒ | ■ | ■ |
| E571 | ▒ | ▒ | ▒ | ▒ | ▒ | ▒ | ■ |

■ Strong reaction
▒ Medium reaction

E: immunopurified antibodies (eluted), on corresponding recombinant proteins.
P: recombinant protein.

TABLE 5.2

Cross reactivities on nucleotide level between
clones of the Pf11-1 family*

| PM clones | PCR571 (1) | Control probe |
|---|---|---|
| 43 | +++ | ++ |
| 88 | ++ | 0 |
| 322 | +++++ | +++++ |
| 525 | ++++ | +++++ |
| 563 | ++++ | ++++ |
| 571 | +++++ | +++++ |
| 676f | +++++ | ++++ |
| 729E | +++ | +++++ |
| 263 | ++++ | NT |
| 381 | ++ | NT |
| 453 | +++ | NT |

*Signal intensity symbolized by plus signs.
NT: not tested

TABLE 5.3

Homologies of clone sequences studied by BLAST

| Clone | Nucelotide size (bp)[1] | Amino acid repeats | Homology Nucleotides Proteins | Degree of homology with 571 Nucleotides Proteins |
|---|---|---|---|---|
| DG43 | 900 | PIVeELLEE | Pf11-1 Part 1: 94%, 100% (=88) | 80%, 80% |
| DG88 | 900 | PIVeELLEE | Pf11-1 Part 1: 94%, 100% (=43) | Idem DG43 |
| DG263-7 | 253 | None | *Plasmodium falciparum* Chr 12 95%, 60% | — |
| DG263-8 | 176 | None | P.f. CHR12 95%, 45%, human chr22 58% | — |
| DG322-1 | 500 | — | — | — |
| DG322-2 | 2000 | PeeVLEEvl | Pf11-1 86%, 65% | 79% |
| DG381 | 400 | PEklvEEVI | plastid tRNA 100%, CHR2 71% | — |
| DG453 | 300 | PIVEEvVEE | Pf11-1 Part 2 88%, 83% | 93%, 72% |
| DG525 | 450 | PeleEVEvl | GLURP R2 98%, 100% | — |
| DG563 | 438 | PIVEEvvEE | Pf11-1 Part 4: 86%, Part 1 68% | 75%, 56% |
| DG571 | 550 | PEEiIEEiv | Pf11-1 Part 5 87%, 55% | 100%, 100% |
| DG676f | 2000 | PvVEEvLEE | Pf11.1 Part 4 88%, Part 5 75% | 74%, 44% |
| DG729E | 1.7 | — | mal3P5 100% | — |

[1]Estimated size with respect to PCR products obtained, or the precise size when the entire clone has been sequenced.
CHR: chromosome;
part: portion

TABLE 5.4

IFI reactivity tested with antibodies specific to $His_6$-571 and Vi571

| Parasites | a-$His_6$-571, aVi571 mouse or human |
|---|---|
| *Plasmodium falciparum* NF54 sporozoites | ++ |
| *P. yoelli* clone 1.1 sporozoites | ++ |
| *Plasmodium falciparum* hepatic stage | ++ |
| T23 blood stage rings/schizonts | ++/+++ (75%) |
| NF54 blood stage rings/schizonts | ++/+++ (75%) |

TABLE 5.5

Cell response in mice immunized with pNAK571

| | Lymphocyte proliferation stimulation index | | Gamma interferon IU/ml | |
|---|---|---|---|---|
| Mouse strain | 571 pGEX | NNpGEX | 571 pGEX | NNpGEX |
| C3H dead | 0.9 ± 0.1 | 0.7 ± 0.05 | 31.0 ± 2.5 | 21.21 ± 10.6 |
| C3H | 0.9 ± 0.2 | 0.7 ± 0.1 | 30.2 ± 2.6 | 10.50 ± 2.03 |
| C3H | 0.8 ± 0.2 | 0.9 ± 0.2 | 16.8 ± 0.1 | 6.65 ± 2.8 |
| Positive | 0/3 | — | 2/3 | — |
| BALB/c | 3.5 ± 0.3 | 2.7 ± 0.13 | 23.1 ± 0.9 | 10.36 ± 2.2 |
| BALB/c | 1.9 ± 0.3 | 1.2 ± 0.1 | 15.9 ± 2.1 | 8.63 ± 3.9 |
| BALB/c (dead) | 3.2 ± 0.9 | 1.5 ± 0.1 | 5.3 ± 1.3 | 1.06 ± 0.5 |
| Positive | 2/3 | — | 3/3 | — |

NNpGEX: GST fusion recombinant of non relevant LSA3.

Although the present invention has been described with respect to preferred implementations, it would be clear to persons skilled in the art or science in question that it would be possible to introduce variations and modifications without departing from the scope of the invention described and claimed in this document.

What is claimed is:

1. An isolated or purified polypeptide consisting of SEQ ID NO: 3 (DG747).

2. An isolated or purified polypeptide comprising:
   a) a peptide sequence with at least 40 consecutive amino acids identical to SEQ ID NO: 3 (DG747); or
   b) a polypeptide having 95% identity with the sequence as claimed in claim 1.

3. A recombinant or chimeric recombinant polypeptide, comprising an isolated or purified polypeptide as claimed in claim 1.

4. An isolated or purified antigen comprising:
   a) an isolated or purified polypeptide as claimed in claim 2 or
   b) a recombinant or chimeric recombinant polypeptide comprising at least one polypeptide according to a).

5. An antigenic conjugate comprising at least one isolated or purified antigen as claimed in claim 4 and a support on which said antigen is adsorbed.

6. A conjugate according to claim 5, wherein the support is microspheres, microparticles of latex beads, polyphosphoglycan microparticles (PGLA), or polystyrene microparticles.

7. A process for immunizing individuals who are infected or susceptible of being infected with malaria comprising administering to the individuals a conjugate as claimed in claim 5.

8. A method of treating malaria comprising administering a product to a human, wherein the product comprises:
   a) at least one isolated or purified antigen as claimed in claim 4 or
   b) an antigenic conjugate comprising at least one isolated or purified antigen as claimed in claim 4 and a support on which said antigen is adsorbed.

9. An in vitro process of detecting malaria in an individual susceptible of being infected with *Plasmodium falciparum*, wherein the process comprises:
   a) bringing a biological sample removed from an individual susceptible of being infected with *Plasmodium falciparum* into contact with at least one isolated or purified antigen as claimed in claim 4 or an antigenic conjugate comprising at least one isolated or purified antigen as claimed in claim 4 and a support on which said antigen is adsorbed under conditions allowing the formation of an immune complex between the at least one antigen or the antigenic conjugate and an antibody that may be present in said biological sample, wherein said biological sample is a biological fluid, biological tissue, or biological fluid and biological tissue; and
   b) detecting in vitro any immune complex formed.

10. A recombinant or chimeric recombinant polypeptide comprising an isolated or purified polypeptide as claimed in claim 2.

11. A process as claimed in claim 9, wherein step a) further comprises bringing the biological tissue, the biological fluid, or the biological tissue and biological fluid into contact with at least one epitope from CS, MSP-1, MSP-3, LSA-1, TRAP, STARP, SALSA, SALSA 1, SALSA II, or LSA-3.

12. An isolated or purified polypeptide comprising the 64 amino acids of SEQ ID NO: 3 (DG747).

13. An isolated or purified polypeptide comprising:
   a) a polypeptide with at least 40 consecutive amino acids identical to the sequence claimed in claim 12; or
   b) a polypeptide having 95% identity with the sequence claimed in claim 12.

* * * * *

```
                        SEQUENCE LISTING

<160> NUMBER OF SEQ ID NOS: 18

<210> SEQ ID NO 1
<211> LENGTH: 192
<212> TYPE: DNA
<213> ORGANISM: Plasmodium falciparum

<400> SEQUENCE: 1
gaattccata tgcacgatta catatatgat gatcgtatct acaataatga taaagagaaa     60
aatgttataa aaagtgataa taaaaatgtt ataaaaagtg ataataaaaa tgattataaa    120
```

```
aagtgtaata aaaatgttat aaaaagtgat aataaaaatg ttataaaaag tgataataaa      180
aatgtggaat tc                                                         192

<210> SEQ ID NO 2
<211> LENGTH: 351
<212> TYPE: DNA
<213> ORGANISM: Plasmodium falciparum

<400> SEQUENCE: 2
gaattcccag atcctcgaag taatgaccaa gaagatgcta ctgacgatgt tgtagaaaat      60
agtagagatg ataataatag tctctctaat agcgtagata atcaaagtaa tgttttaaat     120
agagaagatc ctattgcttc tgaaactgaa gttgtaagtg aacctgagga ttcaagtagg     180
ataatgacta cagaagttcc aagtactact gtaaaacccc ctgatgaaaa acgatctgaa     240
gaagtaggag aaaaagaagc taagaaaatt aaagtagaac tgttgtacc aagagccatt     300 ggagaaccaa tggaaaattc tgtgagcgta cagtcccctc ctaaggaatt c              351

<210> SEQ ID NO 3
<211> LENGTH: 64
<212> TYPE: PRT
<213> ORGANISM: Plasmodium falciparum

<400> SEQUENCE: 3

Glu Phe His Met His Asp Tyr Ile Tyr Asp Asp Arg Ile Tyr Asn Asn
1               5                   10                  15

Asp Lys Glu Lys Asn Val Ile Lys Ser Asp Asn Lys Asn Val Ile Lys
            20                  25                  30

Ser Asp Asn Lys Asn Asp Tyr Lys Lys Cys Asn Lys Asn Val Ile Lys
        35                  40                  45

Ser Asp Asn Lys Asn Val Ile Lys Ser Asp Asn Lys Asn Val Glu Phe
    50                  55                  60

<210> SEQ ID NO 4
<211> LENGTH: 117
<212> TYPE: PRT
<213> ORGANISM: Plasmodium falciparum

<400> SEQUENCE: 4

Glu Phe Pro Asp Pro Arg Ser Asn Asp Gln Glu Asp Ala Thr Asp Asp
1               5                   10                  15

Val Val Glu Asn Ser Arg Asp Asp Asn Asn Ser Leu Ser Asn Ser Val
            20                  25                  30

Asp Asn Gln Ser Asn Val Leu Asn Arg Glu Asp Pro Ile Ala Ser Glu
        35                  40                  45

Thr Glu Val Val Ser Glu Pro Glu Asp Ser Ser Arg Ile Met Thr Thr
    50                  55                  60

Glu Val Pro Ser Thr Thr Val Lys Pro Pro Asp Glu Lys Arg Ser Glu
65                  70                  75                  80

Glu Val Gly Glu Lys Glu Ala Lys Glu Ile Lys Val Glu Pro Val Val
            85                  90                  95

Pro Arg Ala Ile Gly Glu Pro Met Glu Asn Ser Val Ser Val Gln Ser
            100                 105                 110

Pro Pro Lys Glu Phe
        115

<210> SEQ ID NO 5
```

```
<211> LENGTH: 5
<212> TYPE: PRT
<213> ORGANISM: Plasmodium falciparum

<400> SEQUENCE: 5

Asp Asn Lys Asn Val
1               5

<210> SEQ ID NO 6
<211> LENGTH: 5
<212> TYPE: PRT
<213> ORGANISM: Plasmodium falciparum

<400> SEQUENCE: 6

Asp Asn Lys Asn Asp
1               5

<210> SEQ ID NO 7
<211> LENGTH: 6
<212> TYPE: PRT
<213> ORGANISM: Plasmodium falciparum

<400> SEQUENCE: 7

Asp Lys Glu Lys Asn Val
1               5

<210> SEQ ID NO 8
<211> LENGTH: 7
<212> TYPE: PRT
<213> ORGANISM: Plasmodium falciparum

<400> SEQUENCE: 8

Lys Ser Asp Asn Lys Asn Val
1               5

<210> SEQ ID NO 9
<211> LENGTH: 1524
<212> TYPE: DNA
<213> ORGANISM: Plasmodium falciparum
<220> FEATURE:
<221> NAME/KEY: CDS
<222> LOCATION: (1)..(1524)
<223> OTHER INFORMATION:

<400> SEQUENCE: 9
```

| | | | | | | | | | | | | | | | | |
|---|---|---|---|---|---|---|---|---|---|---|---|---|---|---|---|---|
| atg | aag | acg | aca | aaa | gaa | aat | gac | aat | aat | aac | ata | gta | cat | tat | gta | 48 |
| Met | Lys | Thr | Thr | Lys | Glu | Asn | Asp | Asn | Asn | Asn | Ile | Val | His | Tyr | Val | |
| 1 | | | | 5 | | | | | 10 | | | | | 15 | | |
| gat | tgg | ata | aac | cag | att | ttt | aaa | aag | aat | tct | tta | caa | tgt | gat | tta | 96 |
| Asp | Trp | Ile | Asn | Gln | Ile | Phe | Lys | Lys | Asn | Ser | Leu | Gln | Cys | Asp | Leu | |
| | | | 20 | | | | | 25 | | | | | 30 | | | |
| tat | ttt | ttg | gat | gac | aac | aaa | gaa | aaa | gat | gtt | agt | aag | aaa | aga | aaa | 144 |
| Tyr | Phe | Leu | Asp | Asp | Asn | Lys | Glu | Lys | Asp | Val | Ser | Lys | Lys | Arg | Lys | |
| | | 35 | | | | | 40 | | | | | 45 | | | | |
| gct | caa | ttg | aag | gat | gaa | tat | gat | aat | ata | tca | agg | agc | aaa | gaa | aat | 192 |
| Ala | Gln | Leu | Lys | Asp | Glu | Tyr | Asp | Asn | Ile | Ser | Arg | Ser | Lys | Glu | Asn | |
| 50 | | | | | 55 | | | | | 60 | | | | | | |
| att | aat | aat | tcc | aaa | aaa | ata | aaa | aat | gaa | tta | agt | ata | aaa | gat | aat | 240 |
| Ile | Asn | Asn | Ser | Lys | Lys | Ile | Lys | Asn | Glu | Leu | Ser | Ile | Lys | Asp | Asn | |
| 65 | | | | | 70 | | | | | 75 | | | | | 80 | |
| atg | cac | gat | tac | ata | tat | gat | gat | cgt | atc | tac | aat | aat | gat | aaa | gag | 288 |
| Met | His | Asp | Tyr | Ile | Tyr | Asp | Asp | Arg | Ile | Tyr | Asn | Asn | Asp | Lys | Glu | |
| | | | | 85 | | | | | 90 | | | | | 95 | | |
| aaa | aat | gtt | ata | aaa | agt | gat | aat | aaa | aat | gtt | ata | aaa | agt | gat | aat | 336 |

```
                Lys Asn Val Ile Lys Ser Asp Asn Lys Asn Val Ile Lys Ser Asp Asn
                                100                 105                 110 aaa aat gat tat aaa aag tgt aat aaa aat gtt ata aaa agt gat aat                  384
Lys Asn Asp Tyr Lys Lys Cys Asn Lys Asn Val Ile Lys Ser Asp Asn
            115                 120                 125 aaa aat gtt ata aaa agt gat aat aaa aat gtt ata aaa agt gat aat                  432
Lys Asn Val Ile Lys Ser Asp Asn Lys Asn Val Ile Lys Ser Asp Asn
130                 135                 140 aaa aat gtt ata aaa agt gat tat aaa agt gat gat aga aat gct tgt                  480
Lys Asn Val Ile Lys Ser Asp Tyr Lys Ser Asp Asp Arg Asn Ala Cys
145                 150                 155                 160 gat att tat aaa agt aat aaa aaa aat gtt cct gat aat tgc cat ata                  528
Asp Ile Tyr Lys Ser Asn Lys Lys Asn Val Pro Asp Asn Cys His Ile
                165                 170                 175 tat gat gat aat agt tca gtt gaa aat tta gat gga aaa aat aaa tta                  576
Tyr Asp Asp Asn Ser Ser Val Glu Asn Leu Asp Gly Lys Asn Lys Leu
            180                 185                 190 aat aat ata agg aac ata cat aat gat aac tca tct tca tgc gat ata                  624
Asn Asn Ile Arg Asn Ile His Asn Asp Asn Ser Ser Ser Cys Asp Ile
        195                 200                 205 tcc gat ata aaa agt gaa gat gaa tat ata gaa cca tat gaa aaa aag                  672
Ser Asp Ile Lys Ser Glu Asp Glu Tyr Ile Glu Pro Tyr Glu Lys Lys
210                 215                 220 aat gaa gaa aat ata aat gaa tat aag aat aag aaa aat ata gcc aat                  720
Asn Glu Glu Asn Ile Asn Glu Tyr Lys Asn Lys Lys Asn Ile Ala Asn
225                 230                 235                 240 gaa aat ata aaa gaa gga aag agt tca att tat aat gat gaa cat aat                  768
Glu Asn Ile Lys Glu Gly Lys Ser Ser Ile Tyr Asn Asp Glu His Asn
                245                 250                 255 tat aat tca tta tta tat aat tct tgt aat ggt gaa ata agt aag atc                  816
Tyr Asn Ser Leu Leu Tyr Asn Ser Cys Asn Gly Glu Ile Ser Lys Ile
            260                 265                 270 aac aaa ata agt agt cat aat aat att gat aat aat atg gat aat tat                  864
Asn Lys Ile Ser Ser His Asn Asn Ile Asp Asn Asn Met Asp Asn Tyr
        275                 280                 285 aat acg ttt gca aat gtg aat aat ttt ata ata tat tcc tca gat gat                  912
Asn Thr Phe Ala Asn Val Asn Asn Phe Ile Ile Tyr Ser Ser Asp Asp
    290                 295                 300 gaa gat aat ata tca aat tat tat aat ggt aaa gac gta tta aat gat                  960
Glu Asp Asn Ile Ser Asn Tyr Tyr Asn Gly Lys Asp Val Leu Asn Asp
305                 310                 315                 320 gag att atg ttc cct ata aaa ttt aat ttt gaa aaa tta aaa aaa aat                 1008
Glu Ile Met Phe Pro Ile Lys Phe Asn Phe Glu Lys Leu Lys Lys Asn
                325                 330                 335 att tat gta ata gag cat ata gac aaa ata tat tat gat aca ttt tta                 1056
Ile Tyr Val Ile Glu His Ile Asp Lys Ile Tyr Tyr Asp Thr Phe Leu
            340                 345                 350 aat aaa aat cca agt gaa aaa agt gtt ttt atg aat gat gaa tct act                 1104
Asn Lys Asn Pro Ser Glu Lys Ser Val Phe Met Asn Asp Glu Ser Thr
        355                 360                 365 ggt tat ttg aaa aat gat gtg aat gac aaa tgt gtt gtt gat aat ata                 1152
Gly Tyr Leu Lys Asn Asp Val Asn Asp Lys Cys Val Val Asp Asn Ile
    370                 375                 380 aat gtt att aat cct tct agt gtg aat acg ttg agt aat att tca aat                 1200
Asn Val Ile Asn Pro Ser Ser Val Asn Thr Leu Ser Asn Ile Ser Asn
385                 390                 395                 400 att agg aat gaa aaa ata gaa aat aat aat aag aat gaa aaa tta ata                 1248
Ile Arg Asn Glu Lys Ile Glu Asn Asn Asn Lys Asn Glu Lys Leu Ile
                405                 410                 415
```

|  |  |  |  |  |  |  |  |  |  |  |  |  |  |  |  |
|---|---|---|---|---|---|---|---|---|---|---|---|---|---|---|---|
| aaa | tca | tat | cct | aca | caa | tca | aaa | aat | gtt | atg | agt | aca | ttt | tcc | ttt | 1296 |
| Lys | Ser | Tyr | Pro | Thr | Gln | Ser | Lys | Asn | Val | Met | Ser | Thr | Phe | Ser | Phe |
|  |  |  | 420 |  |  |  | 425 |  |  |  |  | 430 |

```
         420                 425                 430 tgg aat att gaa aag gag aca ttt ata aca aaa cct ttg tat gca caa    1344
Trp Asn Ile Glu Lys Glu Thr Phe Ile Thr Lys Pro Leu Tyr Ala Gln
            435                 440                 445 aat ttg aga aaa aaa caa ttt agt tta tta gat gaa tct gaa gag atg    1392
Asn Leu Arg Lys Lys Gln Phe Ser Leu Leu Asp Glu Ser Glu Glu Met
    450                 455                 460 ata aga aat tat tca tct aat caa tat tct ata aaa ttt gta cca aga    1440
Ile Arg Asn Tyr Ser Ser Asn Gln Tyr Ser Ile Lys Phe Val Pro Arg
465                 470                 475                 480 cat tta tta tat gta atg agt caa gtt gct tct cga tcc ttt ttt gat    1488
His Leu Leu Tyr Val Met Ser Gln Val Ala Ser Arg Ser Phe Phe Asp
                485                 490                 495 cct tta tat aga aag cag tta ttt ttt cgt tac taa                    1524
Pro Leu Tyr Arg Lys Gln Leu Phe Phe Arg Tyr
            500                 505

<210> SEQ ID NO 10
<211> LENGTH: 507
<212> TYPE: PRT
<213> ORGANISM: Plasmodium falciparum

<400> SEQUENCE: 10

Met Lys Thr Thr Lys Glu Asn Asp Asn Asn Asn Ile Val His Tyr Val
1               5                   10                  15

Asp Trp Ile Asn Gln Ile Phe Lys Lys Asn Ser Leu Gln Cys Asp Leu
            20                  25                  30

Tyr Phe Leu Asp Asp Asn Lys Glu Lys Asp Val Ser Lys Lys Arg Lys
        35                  40                  45

Ala Gln Leu Lys Asp Glu Tyr Asp Asn Ile Ser Arg Ser Lys Glu Asn
    50                  55                  60

Ile Asn Asn Ser Lys Lys Ile Lys Asn Glu Leu Ser Ile Lys Asp Asn
65                  70                  75                  80

Met His Asp Tyr Ile Tyr Asp Asp Arg Ile Tyr Asn Asn Asp Lys Glu
                85                  90                  95

Lys Asn Val Ile Lys Ser Asp Asn Lys Asn Val Ile Lys Ser Asp Asn
            100                 105                 110

Lys Asn Asp Tyr Lys Lys Cys Asn Lys Asn Val Ile Lys Ser Asp Asn
        115                 120                 125

Lys Asn Val Ile Lys Ser Asp Asn Lys Asn Val Ile Lys Ser Asp Asn
    130                 135                 140

Lys Asn Val Ile Lys Ser Asp Tyr Lys Ser Asp Asp Arg Asn Ala Cys
145                 150                 155                 160

Asp Ile Tyr Lys Ser Asn Lys Lys Asn Val Pro Asp Asn Cys His Ile
                165                 170                 175

Tyr Asp Asp Asn Ser Ser Val Glu Asn Leu Asp Gly Lys Asn Lys Leu
            180                 185                 190

Asn Asn Ile Arg Asn Ile His Asn Asp Asn Ser Ser Cys Asp Ile
        195                 200                 205

Ser Asp Ile Lys Ser Glu Asp Glu Tyr Ile Glu Pro Tyr Glu Lys Lys
    210                 215                 220

Asn Glu Glu Asn Ile Asn Glu Tyr Lys Asn Lys Asn Ile Ala Asn
225                 230                 235                 240

Glu Asn Ile Lys Glu Gly Lys Ser Ser Ile Tyr Asn Asp Glu His Asn
                245                 250                 255
```

```
Tyr Asn Ser Leu Leu Tyr Asn Ser Cys Asn Gly Glu Ile Ser Lys Ile
            260                 265                 270

Asn Lys Ile Ser Ser His Asn Ile Asp Asn Asn Met Asp Asn Tyr
        275                 280                 285

Asn Thr Phe Ala Asn Val Asn Asn Phe Ile Ile Tyr Ser Ser Asp Asp
            290                 295                 300

Glu Asp Asn Ile Ser Asn Tyr Tyr Asn Gly Lys Asp Val Leu Asn Asp
305                 310                 315                 320

Glu Ile Met Phe Pro Ile Lys Phe Asn Phe Glu Lys Leu Lys Lys Asn
                325                 330                 335

Ile Tyr Val Ile Glu His Ile Asp Lys Ile Tyr Tyr Asp Thr Phe Leu
                340                 345                 350

Asn Lys Asn Pro Ser Glu Lys Ser Val Phe Met Asn Asp Glu Ser Thr
            355                 360                 365

Gly Tyr Leu Lys Asn Asp Val Asn Asp Lys Cys Val Val Asp Asn Ile
        370                 375                 380

Asn Val Ile Asn Pro Ser Ser Val Asn Thr Leu Ser Asn Ile Ser Asn
385                 390                 395                 400

Ile Arg Asn Glu Lys Ile Glu Asn Asn Lys Asn Glu Lys Leu Ile
                405                 410                 415

Lys Ser Tyr Pro Thr Gln Ser Lys Asn Val Met Ser Thr Phe Ser Phe
            420                 425                 430

Trp Asn Ile Glu Lys Glu Thr Phe Ile Thr Lys Pro Leu Tyr Ala Gln
        435                 440                 445

Asn Leu Arg Lys Lys Gln Phe Ser Leu Leu Asp Glu Ser Glu Glu Met
            450                 455                 460

Ile Arg Asn Tyr Ser Ser Asn Gln Tyr Ser Ile Lys Phe Val Pro Arg
465                 470                 475                 480

His Leu Leu Tyr Val Met Ser Gln Val Ala Ser Arg Ser Phe Phe Asp
                485                 490                 495

Pro Leu Tyr Arg Lys Gln Leu Phe Phe Arg Tyr
            500                 505

<210> SEQ ID NO 11
<211> LENGTH: 5050
<212> TYPE: DNA
<213> ORGANISM: Plasmodium falciparum
<220> FEATURE:
<221> NAME/KEY: CDS
<222> LOCATION: (1)..(4464)
<223> OTHER INFORMATION:
<220> FEATURE:
<221> NAME/KEY: CDS
<222> LOCATION: (4557)..(4634)
<223> OTHER INFORMATION:
<220> FEATURE:
<221> NAME/KEY: CDS
<222> LOCATION: (4751)..(4837)
<223> OTHER INFORMATION:
<220> FEATURE:
<221> NAME/KEY: CDS
<222> LOCATION: (4973)..(5047)
<223> OTHER INFORMATION:

<400> SEQUENCE: 11 atg aaa ggg aaa atg aat atg tgt ttg ttt ttt ttc tat tct ata tta      48
Met Lys Gly Lys Met Asn Met Cys Leu Phe Phe Phe Tyr Ser Ile Leu
1               5                   10                  15 tat gtt gta tta tgt acc tat gta tta ggt ata agt gaa gag tat ttg     96
Tyr Val Val Leu Cys Thr Tyr Val Leu Gly Ile Ser Glu Glu Tyr Leu
```

```
                    20                  25                  30
aag gaa agg ccc caa ggt tta aat gtt gag act aat aat aat aat    144
Lys Glu Arg Pro Gln Gly Leu Asn Val Glu Thr Asn Asn Asn Asn
         35                  40                  45 aat aat aat aat aat aat agt aat agt aac gat gcg atg tct ttt gta    192
Asn Asn Asn Asn Asn Asn Ser Asn Ser Asn Asp Ala Met Ser Phe Val
 50              55                  60 aat gaa gta ata agg ttt ata gaa aac gag aag gat gat aaa gaa gat    240
Asn Glu Val Ile Arg Phe Ile Glu Asn Glu Lys Asp Asp Lys Glu Asp
 65              70                  75                  80 aaa aaa gtg aag ata ata tct aga cct gtt gag aat aca tta cat aga    288
Lys Lys Val Lys Ile Ile Ser Arg Pro Val Glu Asn Thr Leu His Arg
                 85                  90                  95 tat cca gtt agt tct ttt ctg aat atc aaa aag tat ggt agg aaa ggg    336
Tyr Pro Val Ser Ser Phe Leu Asn Ile Lys Lys Tyr Gly Arg Lys Gly
             100                 105                 110 gaa tat ttg aat aga aat agt ttt gtt caa aga tca tat ata agg ggt    384
Glu Tyr Leu Asn Arg Asn Ser Phe Val Gln Arg Ser Tyr Ile Arg Gly
         115                 120                 125 tgt aaa gga aaa aga agc aca cat aca tgg ata tgt gaa aat aaa ggg    432
Cys Lys Gly Lys Arg Ser Thr His Thr Trp Ile Cys Glu Asn Lys Gly
     130                 135                 140 aat aat aat ata tgt att cct gat aga cgt gta caa tta tgt ata aca    480
Asn Asn Asn Ile Cys Ile Pro Asp Arg Arg Val Gln Leu Cys Ile Thr
145                 150                 155                 160 gct ctt caa gat tta aaa aat tca gga tct gaa acg act gat aga aaa    528
Ala Leu Gln Asp Leu Lys Asn Ser Gly Ser Glu Thr Thr Asp Arg Lys
                 165                 170                 175 tta tta aga gat aaa gta ttt gat tca gct atg tat gaa act gat ttg    576
Leu Leu Arg Asp Lys Val Phe Asp Ser Ala Met Tyr Glu Thr Asp Leu
             180                 185                 190 tta tgg aat aaa tat ggt ttt cgt gga ttt gat gat ttt tgt gac gat    624
Leu Trp Asn Lys Tyr Gly Phe Arg Gly Phe Asp Asp Phe Cys Asp Asp
         195                 200                 205 gta aaa aat agt tat tta gat tat aaa gat gtt ata ttt gga acc gat    672
Val Lys Asn Ser Tyr Leu Asp Tyr Lys Asp Val Ile Phe Gly Thr Asp
     210                 215                 220 tta gat aaa aat aat ata tca aag tta gta gag gaa tca tta aaa cgt    720
Leu Asp Lys Asn Asn Ile Ser Lys Leu Val Glu Glu Ser Leu Lys Arg
225                 230                 235                 240 ttt ttt aaa aaa gat agt agt gta ctt aat cct act gct tgg tgg aga    768
Phe Phe Lys Lys Asp Ser Ser Val Leu Asn Pro Thr Ala Trp Trp Arg
                 245                 250                 255 agg tat gga aca aga cta tgg aaa act atg ata cag cca tat gct cat    816
Arg Tyr Gly Thr Arg Leu Trp Lys Thr Met Ile Gln Pro Tyr Ala His
             260                 265                 270 tta gga tgt aga aaa cct gat gag aat gaa cct cag ata aat aga tgg    864
Leu Gly Cys Arg Lys Pro Asp Glu Asn Glu Pro Gln Ile Asn Arg Trp
         275                 280                 285 att ctg gaa tgg ggg aaa tat aat tgt aga tta atg aag gag aaa gaa    912
Ile Leu Glu Trp Gly Lys Tyr Asn Cys Arg Leu Met Lys Glu Lys Glu
     290                 295                 300 aaa ttg tta aca gga gaa tgt tct gtt aat aga aaa aaa tct gac tgc    960
Lys Leu Leu Thr Gly Glu Cys Ser Val Asn Arg Lys Lys Ser Asp Cys
305                 310                 315                 320 tca acc gga tgt aat aat gag tgt tat acc tat agg agt ctt att aat    1008
Ser Thr Gly Cys Asn Asn Glu Cys Tyr Thr Tyr Arg Ser Leu Ile Asn
                 325                 330                 335 aga caa aga tat gag gtc tct ata tta gga aaa aaa tat att aaa gta    1056
```

```
                Arg Gln Arg Tyr Glu Val Ser Ile Leu Gly Lys Lys Tyr Ile Lys Val
                            340                 345                 350 gta cga tat act ata ttt agg aga aaa ata gtt caa cct gat aat gct       1104
Val Arg Tyr Thr Ile Phe Arg Arg Lys Ile Val Gln Pro Asp Asn Ala
                355                 360                 365 ttg gat ttt tta aaa tta aat tgt tct gag tgt aag gat att gat ttt       1152
Leu Asp Phe Leu Lys Leu Asn Cys Ser Glu Cys Lys Asp Ile Asp Phe
        370                 375                 380 aaa ccc ttt ttt gaa ttt gaa tat ggt aaa tat gaa gaa aaa tgt atg       1200
Lys Pro Phe Phe Glu Phe Glu Tyr Gly Lys Tyr Glu Glu Lys Cys Met
385                 390                 395                 400 tgt caa tca tat att gat tta aaa atc caa ttt aaa aat aat gat att       1248
Cys Gln Ser Tyr Ile Asp Leu Lys Ile Gln Phe Lys Asn Asn Asp Ile
                405                 410                 415 tgt tca ttt aat gct caa aca gat act gtt tct agc gat aaa aga ttt       1296
Cys Ser Phe Asn Ala Gln Thr Asp Thr Val Ser Ser Asp Lys Arg Phe
        420                 425                 430 tgt ctt gaa aag aaa gaa ttt aaa cca tgg aaa tgt gat aaa aat tct       1344
Cys Leu Glu Lys Lys Glu Phe Lys Pro Trp Lys Cys Asp Lys Asn Ser
435                 440                 445 ttt gaa aca gtt cat cat aaa ggt gta tgt gtg tca ccg aga aga caa       1392
Phe Glu Thr Val His His Lys Gly Val Cys Val Ser Pro Arg Arg Gln
        450                 455                 460 ggt ttt tgt tta gga aat ttg aac tat cta ctg aat gat gat att tat       1440
Gly Phe Cys Leu Gly Asn Leu Asn Tyr Leu Leu Asn Asp Asp Ile Tyr
465                 470                 475                 480 aat gta cat aat tca caa cta ctt atc gaa att ata atg gct tct aaa       1488
Asn Val His Asn Ser Gln Leu Leu Ile Glu Ile Ile Met Ala Ser Lys
                485                 490                 495 caa gaa gga aag tta tta tgg aaa aaa cat gga aca ata ctt gat aac       1536
Gln Glu Gly Lys Leu Leu Trp Lys Lys His Gly Thr Ile Leu Asp Asn
        500                 505                 510 cag aat gca tgc aaa tat ata aat gat agt tat gtt gat tat aaa gat       1584
Gln Asn Ala Cys Lys Tyr Ile Asn Asp Ser Tyr Val Asp Tyr Lys Asp
515                 520                 525 ata gtt att gga aat gat tta tgg aat gat aac aac tct ata aaa gtt       1632
Ile Val Ile Gly Asn Asp Leu Trp Asn Asp Asn Asn Ser Ile Lys Val
                530                 535                 540 caa aat aat tta aat tta att ttt gaa aga aat ttt ggt tat aaa gtt       1680
Gln Asn Asn Leu Asn Leu Ile Phe Glu Arg Asn Phe Gly Tyr Lys Val
545                 550                 555                 560 gga aga aat aaa ctc ttt aaa aca att aaa gaa tta aaa aat gta tgg       1728
Gly Arg Asn Lys Leu Phe Lys Thr Ile Lys Glu Leu Lys Asn Val Trp
                565                 570                 575 tgg ata tta aat aga aat aaa gta tgg gaa tca atg aga tgt gga att       1776
Trp Ile Leu Asn Arg Asn Lys Val Trp Glu Ser Met Arg Cys Gly Ile
        580                 585                 590 gac gaa gta gat caa cgt aga aaa act tgt gaa aga ata gat gaa cta       1824
Asp Glu Val Asp Gln Arg Arg Lys Thr Cys Glu Arg Ile Asp Glu Leu
595                 600                 605 gaa aac atg cca caa ttc ttt aga tgg ttt tca caa tgg gca cat ttc       1872
Glu Asn Met Pro Gln Phe Phe Arg Trp Phe Ser Gln Trp Ala His Phe
                610                 615                 620 ttt tgt aag gaa aaa gaa tat tgg gaa tta aaa tta aat gat aaa tgt       1920
Phe Cys Lys Glu Lys Glu Tyr Trp Glu Leu Lys Leu Asn Asp Lys Cys
625                 630                 635                 640 aca ggt aat aat gga aaa tcc tta tgt cag gat aaa aca tgt caa aat       1968
Thr Gly Asn Asn Gly Lys Ser Leu Cys Gln Asp Lys Thr Cys Gln Asn
        645                 650                 655
```

```
                                                                 -continued gtg tgt act aat atg aat tat tgg aca tat act aga aaa tta gct tat     2016
Val Cys Thr Asn Met Asn Tyr Trp Thr Tyr Thr Arg Lys Leu Ala Tyr
        660                 665                 670 gaa ata caa tcc gta aaa tat gat aaa gat aga aaa tta ttt agt ctt     2064
Glu Ile Gln Ser Val Lys Tyr Asp Lys Asp Arg Lys Leu Phe Ser Leu
    675                 680                 685 gct aaa gac aaa aat gta act aca ttt tta aag gaa aat gca aaa aat     2112
Ala Lys Asp Lys Asn Val Thr Thr Phe Leu Lys Glu Asn Ala Lys Asn
690                 695                 700 tgt tct aat ata gat ttt aca aaa ata ttc gat cag ctt gac aaa ctc     2160
Cys Ser Asn Ile Asp Phe Thr Lys Ile Phe Asp Gln Leu Asp Lys Leu
705                 710                 715                 720 ttt aag gaa aga tgt tca tgt atg gat aca caa gtt tta gaa gta aaa     2208
Phe Lys Glu Arg Cys Ser Cys Met Asp Thr Gln Val Leu Glu Val Lys
                725                 730                 735 aac aaa gaa atg tta tct ata gac tca aat agt gaa gat gcg aca gat     2256
Asn Lys Glu Met Leu Ser Ile Asp Ser Asn Ser Glu Asp Ala Thr Asp
            740                 745                 750 ata agt gag aaa aat gga gag gaa gaa tta tat gta aat cac aat tct     2304
Ile Ser Glu Lys Asn Gly Glu Glu Glu Leu Tyr Val Asn His Asn Ser
        755                 760                 765 gtg agt gtc gca agt ggt aat aaa gaa atc gaa aag agt aag gat gaa     2352
Val Ser Val Ala Ser Gly Asn Lys Glu Ile Glu Lys Ser Lys Asp Glu
    770                 775                 780 aag caa cct gaa aaa gaa gca aaa caa act aat gga act tta acc gta     2400
Lys Gln Pro Glu Lys Glu Ala Lys Gln Thr Asn Gly Thr Leu Thr Val
785                 790                 795                 800 cga act gac aaa gat tca gat aga aac aaa gga aaa gat aca gct act     2448
Arg Thr Asp Lys Asp Ser Asp Arg Asn Lys Gly Lys Asp Thr Ala Thr
                805                 810                 815 gat aca aaa aat tca cct gaa aat tta aaa gta cag gaa cat gga aca     2496
Asp Thr Lys Asn Ser Pro Glu Asn Leu Lys Val Gln Glu His Gly Thr
            820                 825                 830 aat gga gaa aca ata aaa gaa gaa cca cca aaa tta cct gaa tca tct     2544
Asn Gly Glu Thr Ile Lys Glu Glu Pro Pro Lys Leu Pro Glu Ser Ser
        835                 840                 845 gaa aca tta caa tca caa gaa caa tta gaa gca gaa gca caa aaa caa     2592
Glu Thr Leu Gln Ser Gln Glu Gln Leu Glu Ala Glu Ala Gln Lys Gln
    850                 855                 860 aaa caa gaa gaa gaa cca aaa aaa aaa caa gaa gaa gaa cca aaa aaa     2640
Lys Gln Glu Glu Glu Pro Lys Lys Lys Gln Glu Glu Glu Pro Lys Lys
865                 870                 875                 880 aaa caa gaa gaa gaa caa aaa cga gaa caa gaa caa aaa caa gaa caa     2688
Lys Gln Glu Glu Glu Gln Lys Arg Glu Gln Glu Gln Lys Gln Glu Gln
                885                 890                 895 gaa gaa gaa gaa caa aaa caa gaa gaa gaa caa caa ata caa gat caa     2736
Glu Glu Glu Glu Gln Lys Gln Glu Glu Glu Gln Gln Ile Gln Asp Gln
            900                 905                 910 tca caa agt gga tta gat caa tcc tca aaa gta gga gta gcg agt gaa     2784
Ser Gln Ser Gly Leu Asp Gln Ser Ser Lys Val Gly Val Ala Ser Glu
        915                 920                 925 caa aat gaa att tct tca gga caa gaa caa aac gta aaa agc tct tca     2832
Gln Asn Glu Ile Ser Ser Gly Gln Glu Gln Asn Val Lys Ser Ser Ser
    930                 935                 940 cct gaa gta gtt cca caa gaa aca act agt gaa aat ggg tca tca caa     2880
Pro Glu Val Val Pro Gln Glu Thr Thr Ser Glu Asn Gly Ser Ser Gln
945                 950                 955                 960 gac aca aaa ata tca agt act gaa cca aat gag aat tct gtt gta gat     2928
Asp Thr Lys Ile Ser Ser Thr Glu Pro Asn Glu Asn Ser Val Val Asp
                965                 970                 975
```

-continued

| | |
|---|---|
| aga gca aca gat agt atg aat tta gat cct gaa aag gtt cat aat gaa<br>Arg Ala Thr Asp Ser Met Asn Leu Asp Pro Glu Lys Val His Asn Glu<br>               980                        985                        990 | 2976 |
| aat atg agt gat cca aat aca aat act gaa cca gat gca tct tta aaa<br>Asn Met Ser Asp Pro Asn Thr Asn Thr Glu Pro Asp Ala Ser Leu Lys<br>        995                     1000                     1005 | 3024 |
| gat gat aag aag gaa gtt gat gat gcc aaa aaa gaa ctt caa tct<br>Asp Asp Lys Lys Glu Val Asp Asp Ala Lys Lys Glu Leu Gln Ser<br>1010                 1015                    1020 | 3069 |
| act gta tca aga att gaa tct aat gaa cag gac gtt caa agt aca<br>Thr Val Ser Arg Ile Glu Ser Asn Glu Gln Asp Val Gln Ser Thr<br>1025                 1030                    1035 | 3114 |
| cca ccc gaa gat act cct act gtt gaa gga aaa gta gga gat aaa<br>Pro Pro Glu Asp Thr Pro Thr Val Glu Gly Lys Val Gly Asp Lys<br>1040                 1045                    1050 | 3159 |
| gca gaa atg tta act tct ccg cat gcg aca gat aat tct gag tcg<br>Ala Glu Met Leu Thr Ser Pro His Ala Thr Asp Asn Ser Glu Ser<br>1055                 1060                    1065 | 3204 |
| gaa tca ggt tta aat cca act gat gac att aaa aca act gat ggt<br>Glu Ser Gly Leu Asn Pro Thr Asp Asp Ile Lys Thr Thr Asp Gly<br>1070                 1075                    1080 | 3249 |
| gtt gtt aaa gaa caa gaa ata tta ggg gga ggt gaa agt gca act<br>Val Val Lys Glu Gln Glu Ile Leu Gly Gly Gly Glu Ser Ala Thr<br>1085                 1090                    1095 | 3294 |
| gaa aca tca aaa agt aat tta gaa aaa cct aag gat gtt gaa cct<br>Glu Thr Ser Lys Ser Asn Leu Glu Lys Pro Lys Asp Val Glu Pro<br>1100                 1105                    1110 | 3339 |
| tct cat gaa ata tct gaa cct gtt ctt tct ggt aca act ggt aaa<br>Ser His Glu Ile Ser Glu Pro Val Leu Ser Gly Thr Thr Gly Lys<br>1115                 1120                    1125 | 3384 |
| gaa gaa tca gag tta tta aaa agt aaa tcg ata gag acg aag ggg<br>Glu Glu Ser Glu Leu Leu Lys Ser Lys Ser Ile Glu Thr Lys Gly<br>1130                 1135                    1140 | 3429 |
| gaa aca gat cct cga agt aat gac caa gaa gat gct act gac gat<br>Glu Thr Asp Pro Arg Ser Asn Asp Gln Glu Asp Ala Thr Asp Asp<br>1145                 1150                    1155 | 3474 |
| gtt gta gaa aat agt aga gat gat aat aat agt ctc tct aat agc<br>Val Val Glu Asn Ser Arg Asp Asp Asn Asn Ser Leu Ser Asn Ser<br>1160                 1165                    1170 | 3519 |
| gta gat aat caa agt aat gtt tta aat aga gaa gat cct att gct<br>Val Asp Asn Gln Ser Asn Val Leu Asn Arg Glu Asp Pro Ile Ala<br>1175                 1180                    1185 | 3564 |
| tct gaa act gaa gtt gta agt gaa cct gag gat tca agt agg ata<br>Ser Glu Thr Glu Val Val Ser Glu Pro Glu Asp Ser Ser Arg Ile<br>1190                 1195                    1200 | 3609 |
| atg act aca gaa gtt cca agt act act gta aaa ccc cct gat gaa<br>Met Thr Thr Glu Val Pro Ser Thr Thr Val Lys Pro Pro Asp Glu<br>1205                 1210                    1215 | 3654 |
| aaa cga tct gaa gaa gta gga gaa aaa gaa gct aaa gaa att aaa<br>Lys Arg Ser Glu Glu Val Gly Glu Lys Glu Ala Lys Glu Ile Lys<br>1220                 1225                    1230 | 3699 |
| gta gaa cct gtt gta cca aga gcc att gga gaa cca atg gaa aat<br>Val Glu Pro Val Val Pro Arg Ala Ile Gly Glu Pro Met Glu Asn<br>1235                 1240                    1245 | 3744 |
| tct gtg agc gta cag tcc cct cct aat gta gaa gat gtt gaa aaa<br>Ser Val Ser Val Gln Ser Pro Pro Asn Val Glu Asp Val Glu Lys<br>1250                 1255                    1260 | 3789 |
| gaa aca ttg ata tct gag aat aat gga tta cat aat gat aca cac<br>Glu Thr Leu Ile Ser Glu Asn Asn Gly Leu His Asn Asp Thr His | 3834 |

```
                                   -continued
     1265                 1270                 1275
aga gga  aat atc agt gaa aag gat tta atc gat att cat ttg tta         3879
Arg Gly  Asn Ile Ser Glu Lys Asp Leu Ile Asp Ile His Leu Leu
    1280             1285                 1290 aga aat  gaa gcg ggt agt aca ata tta gat gat tct aga aga aat         3924
Arg Asn  Glu Ala Gly Ser Thr Ile Leu Asp Asp Ser Arg Arg Asn
    1295             1300                 1305 gga gaa  atg aca gaa ggt agc gaa agt gat gtt gga gaa tta caa         3969
Gly Glu  Met Thr Glu Gly Ser Glu Ser Asp Val Gly Glu Leu Gln
    1310             1315                 1320 gaa cat  aat ttt agc aca caa caa aaa gat gaa aaa gat ttt gac         4014
Glu His  Asn Phe Ser Thr Gln Gln Lys Asp Glu Lys Asp Phe Asp
    1325             1330                 1335 caa att  gcg agc gat aga gaa aaa gaa gaa att caa aaa tta ctt         4059
Gln Ile  Ala Ser Asp Arg Glu Lys Glu Glu Ile Gln Lys Leu Leu
    1340             1345                 1350 aat ata  gga cat gaa gag gat gaa gat gta tta aaa atg gat aga         4104
Asn Ile  Gly His Glu Glu Asp Glu Asp Val Leu Lys Met Asp Arg
    1355             1360                 1365 aca gag  gat agt atg agt gat gga gtt aat agt cat ttg tat tat         4149
Thr Glu  Asp Ser Met Ser Asp Gly Val Asn Ser His Leu Tyr Tyr
    1370             1375                 1380 aat aat  cta tca agt gaa gaa aaa atg gaa caa tat aat aat aga         4194
Asn Asn  Leu Ser Ser Glu Glu Lys Met Glu Gln Tyr Asn Asn Arg
    1385             1390                 1395 gat gct  tct aaa gat aga gaa gaa ata ttg aat agg tca aac aca         4239
Asp Ala  Ser Lys Asp Arg Glu Glu Ile Leu Asn Arg Ser Asn Thr
    1400             1405                 1410 aat aca  tgt tct aat gaa cat tca tta aaa tat tgt caa tat atg         4284
Asn Thr  Cys Ser Asn Glu His Ser Leu Lys Tyr Cys Gln Tyr Met
    1415             1420                 1425 gaa aga  aat aag gat tta tta gaa aca tgt tct gaa gac aaa agg         4329
Glu Arg  Asn Lys Asp Leu Leu Glu Thr Cys Ser Glu Asp Lys Arg
    1430             1435                 1440 tta cat  tta tgt tgt gaa ata tca gat tat tgt tta aaa ttt ttc         4374
Leu His  Leu Cys Cys Glu Ile Ser Asp Tyr Cys Leu Lys Phe Phe
    1445             1450                 1455 aat cct  aaa tcg ata gaa tac ttt gat tgt aca caa aaa gaa ttt         4419
Asn Pro  Lys Ser Ile Glu Tyr Phe Asp Cys Thr Gln Lys Glu Phe
    1460             1465                 1470 gat gac  cct aca tat aat tgt ttt aga aaa caa aga ttt aca agt         4464
Asp Asp  Pro Thr Tyr Asn Cys Phe Arg Lys Gln Arg Phe Thr Ser
    1475             1480                 1485 atgtcatgtt ataaaattaa aaacaatata cattaatatg ttaataaaaa aaataatata   4524
tttttttctc ttttttctttt tttttaatag gt atg cat tat att gcc ggg ggt   4577
                                    Met His  Tyr Ile Ala Gly Gly
                                        1490             1495 ggt ata ata gcc ctt tta ttg ttt att tta ggt tca gcc agc tat         4622
Gly Ile Ile Ala Leu Leu Leu Phe Ile Leu Gly Ser Ala Ser Tyr
            1500                 1505                 1510 agg aag aat ttg taagaaaaaa aggatgaaga aatataaaca aaaatataaa         4674
Arg Lys Asn Leu tatatgcata tatatttaag tattataaga acatatatat aaataaatat gtatattttt   4734
attttattat tatagg gat gat gaa aaa gga ttc tac gat tct aat tta       4783
                Asp Asp Glu Lys Gly Phe  Tyr Asp Ser Asn Leu
                    1515             1520                 1525 aat gat tct gct ttt gaa tat aat aat aat aaa tat aat aaa tta         4828
Asn Asp Ser Ala Phe Glu Tyr Asn Asn Asn Lys Tyr Asn Lys Leu
```

-continued

```
                  1530              1535              1540
cct tat atg tgtaaggaaa aaactaaaaa acaaaaaaaa aaaaaaatat          4877
Pro Tyr Met atatatatat atatatattt acggatgcat ttccacattc ctattattc ttattcttat  4937 aattttatt atttatttat ttattttttt ttttc gta gtt gat caa caa ata    4990
                                      Val Val Asp Gln Gln Ile
                                                        1545 aat gta gta aat tct gat tta tat tcg gag ggt att tat gat gac      5035
Asn Val Val Asn Ser Asp Leu Tyr Ser Glu Gly Ile Tyr Asp Asp
1550              1555                  1560 aca acg aca ttt taa                                              5050
Thr Thr Thr Phe
1565
```

<210> SEQ ID NO 12
<211> LENGTH: 1568
<212> TYPE: PRT
<213> ORGANISM: Plasmodium falciparum

<400> SEQUENCE: 12

```
Met Lys Gly Lys Met Asn Met Cys Leu Phe Phe Phe Tyr Ser Ile Leu
1               5                   10                  15

Tyr Val Val Leu Cys Thr Tyr Val Leu Gly Ile Ser Glu Glu Tyr Leu
            20                  25                  30

Lys Glu Arg Pro Gln Gly Leu Asn Val Glu Thr Asn Asn Asn Asn
        35                  40                  45

Asn Asn Asn Asn Asn Asn Ser Asn Ser Asn Asp Ala Met Ser Phe Val
    50                  55                  60

Asn Glu Val Ile Arg Phe Ile Glu Asn Glu Lys Asp Asp Lys Glu Asp
65                  70                  75                  80

Lys Lys Val Lys Ile Ile Ser Arg Pro Val Glu Asn Thr Leu His Arg
                85                  90                  95

Tyr Pro Val Ser Ser Phe Leu Asn Ile Lys Lys Tyr Gly Arg Lys Gly
            100                 105                 110

Glu Tyr Leu Asn Arg Asn Ser Phe Val Gln Arg Ser Tyr Ile Arg Gly
        115                 120                 125

Cys Lys Gly Lys Arg Ser Thr His Thr Trp Ile Cys Glu Asn Lys Gly
    130                 135                 140

Asn Asn Asn Ile Cys Ile Pro Asp Arg Arg Val Gln Leu Cys Ile Thr
145                 150                 155                 160

Ala Leu Gln Asp Leu Lys Asn Ser Gly Ser Glu Thr Thr Asp Arg Lys
                165                 170                 175

Leu Leu Arg Asp Lys Val Phe Asp Ser Ala Met Tyr Glu Thr Asp Leu
            180                 185                 190

Leu Trp Asn Lys Tyr Gly Phe Arg Gly Phe Asp Asp Phe Cys Asp Asp
        195                 200                 205

Val Lys Asn Ser Tyr Leu Asp Tyr Lys Asp Val Ile Phe Gly Thr Asp
    210                 215                 220

Leu Asp Lys Asn Asn Ile Ser Lys Leu Val Glu Ser Leu Lys Arg
225                 230                 235                 240

Phe Phe Lys Lys Asp Ser Ser Val Leu Asn Pro Thr Ala Trp Trp Arg
                245                 250                 255

Arg Tyr Gly Thr Arg Leu Trp Lys Thr Met Ile Gln Pro Tyr Ala His
            260                 265                 270

Leu Gly Cys Arg Lys Pro Asp Glu Asn Glu Pro Gln Ile Asn Arg Trp
```

```
            275                 280                 285
Ile Leu Glu Trp Gly Lys Tyr Asn Cys Arg Leu Met Lys Glu Lys Glu
            290                 295                 300
Lys Leu Leu Thr Gly Glu Cys Ser Val Asn Arg Lys Lys Ser Asp Cys
305                 310                 315                 320
Ser Thr Gly Cys Asn Asn Glu Cys Tyr Thr Tyr Arg Ser Leu Ile Asn
                325                 330                 335
Arg Gln Arg Tyr Glu Val Ser Ile Leu Gly Lys Lys Tyr Ile Lys Val
            340                 345                 350
Val Arg Tyr Thr Ile Phe Arg Arg Lys Ile Val Gln Pro Asp Asn Ala
        355                 360                 365
Leu Asp Phe Leu Lys Leu Asn Cys Ser Glu Cys Lys Asp Ile Asp Phe
    370                 375                 380
Lys Pro Phe Phe Glu Phe Glu Tyr Gly Lys Tyr Glu Glu Lys Cys Met
385                 390                 395                 400
Cys Gln Ser Tyr Ile Asp Leu Lys Ile Gln Phe Lys Asn Asn Asp Ile
                405                 410                 415
Cys Ser Phe Asn Ala Gln Thr Asp Thr Val Ser Ser Asp Lys Arg Phe
            420                 425                 430
Cys Leu Glu Lys Lys Glu Phe Lys Pro Trp Lys Cys Asp Lys Asn Ser
        435                 440                 445
Phe Glu Thr Val His His Lys Gly Val Cys Val Ser Pro Arg Arg Gln
    450                 455                 460
Gly Phe Cys Leu Gly Asn Leu Asn Tyr Leu Leu Asn Asp Asp Ile Tyr
465                 470                 475                 480
Asn Val His Asn Ser Gln Leu Leu Ile Glu Ile Met Ala Ser Lys
                485                 490                 495
Gln Glu Gly Lys Leu Leu Trp Lys Lys His Gly Thr Ile Leu Asp Asn
            500                 505                 510
Gln Asn Ala Cys Lys Tyr Ile Asn Asp Ser Tyr Val Asp Tyr Lys Asp
        515                 520                 525
Ile Val Ile Gly Asn Asp Leu Trp Asn Asp Asn Ser Ile Lys Val
    530                 535                 540
Gln Asn Asn Leu Asn Leu Ile Phe Glu Arg Asn Phe Gly Tyr Lys Val
545                 550                 555                 560
Gly Arg Asn Lys Leu Phe Lys Thr Ile Lys Glu Leu Lys Asn Val Trp
                565                 570                 575
Trp Ile Leu Asn Arg Asn Lys Val Trp Glu Ser Met Arg Cys Gly Ile
            580                 585                 590
Asp Glu Val Asp Gln Arg Arg Lys Thr Cys Glu Arg Ile Asp Glu Leu
        595                 600                 605
Glu Asn Met Pro Gln Phe Phe Arg Trp Phe Ser Gln Trp Ala His Phe
    610                 615                 620
Phe Cys Lys Glu Lys Glu Tyr Trp Glu Leu Lys Leu Asn Asp Lys Cys
625                 630                 635                 640
Thr Gly Asn Asn Gly Lys Ser Leu Cys Gln Asp Lys Thr Cys Gln Asn
                645                 650                 655
Val Cys Thr Asn Met Asn Tyr Trp Thr Tyr Thr Arg Lys Leu Ala Tyr
            660                 665                 670
Glu Ile Gln Ser Val Lys Tyr Asp Lys Asp Arg Lys Leu Phe Ser Leu
        675                 680                 685
Ala Lys Asp Lys Asn Val Thr Thr Phe Leu Lys Glu Asn Ala Lys Asn
    690                 695                 700
```

-continued

```
Cys Ser Asn Ile Asp Phe Thr Lys Ile Phe Asp Gln Leu Asp Lys Leu
705                 710                 715                 720

Phe Lys Glu Arg Cys Ser Cys Met Asp Thr Gln Val Leu Glu Val Lys
            725                 730                 735

Asn Lys Glu Met Leu Ser Ile Asp Ser Asn Ser Glu Asp Ala Thr Asp
        740                 745                 750

Ile Ser Glu Lys Asn Gly Glu Glu Leu Tyr Val Asn His Asn Ser
            755                 760                 765

Val Ser Val Ala Ser Gly Asn Lys Glu Ile Glu Lys Ser Lys Asp Glu
770                 775                 780

Lys Gln Pro Glu Lys Glu Ala Lys Gln Thr Asn Gly Thr Leu Thr Val
785                 790                 795                 800

Arg Thr Asp Lys Asp Ser Asp Arg Asn Lys Gly Lys Asp Thr Ala Thr
                805                 810                 815

Asp Thr Lys Asn Ser Pro Glu Asn Leu Lys Val Gln Glu His Gly Thr
                820                 825                 830

Asn Gly Glu Thr Ile Lys Glu Pro Pro Lys Leu Pro Glu Ser Ser
            835                 840                 845

Glu Thr Leu Gln Ser Gln Glu Gln Leu Glu Ala Glu Ala Gln Lys Gln
        850                 855                 860

Lys Gln Glu Glu Glu Pro Lys Lys Gln Glu Glu Pro Lys Lys
865                 870                 875                 880

Lys Gln Glu Glu Glu Gln Lys Arg Glu Gln Gln Lys Gln Glu Gln
                885                 890                 895

Glu Glu Glu Glu Gln Lys Gln Glu Glu Gln Gln Ile Gln Asp Gln
            900                 905                 910

Ser Gln Ser Gly Leu Asp Gln Ser Ser Lys Val Gly Val Ala Ser Glu
        915                 920                 925

Gln Asn Glu Ile Ser Ser Gly Gln Glu Gln Asn Val Lys Ser Ser Ser
    930                 935                 940

Pro Glu Val Val Pro Gln Glu Thr Thr Ser Glu Asn Gly Ser Ser Gln
945                 950                 955                 960

Asp Thr Lys Ile Ser Ser Thr Glu Pro Asn Glu Asn Ser Val Val Asp
                965                 970                 975

Arg Ala Thr Asp Ser Met Asn Leu Asp Pro Glu Lys Val His Asn Glu
            980                 985                 990

Asn Met Ser Asp Pro Asn Thr Asn Thr Glu Pro Asp Ala Ser Leu Lys
        995                 1000                1005

Asp Asp Lys Lys Glu Val Asp Ala Lys Lys Glu Leu Gln Ser
    1010                1015                1020

Thr Val Ser Arg Ile Glu Ser Asn Glu Gln Asp Val Gln Ser Thr
    1025                1030                1035

Pro Pro Glu Asp Thr Pro Thr Val Glu Gly Lys Val Gly Asp Lys
    1040                1045                1050

Ala Glu Met Leu Thr Ser Pro His Ala Thr Asp Asn Ser Glu Ser
    1055                1060                1065

Glu Ser Gly Leu Asn Pro Thr Asp Asp Ile Lys Thr Thr Asp Gly
    1070                1075                1080

Val Val Lys Glu Gln Glu Ile Leu Gly Gly Gly Glu Ser Ala Thr
    1085                1090                1095

Glu Thr Ser Lys Ser Asn Leu Glu Lys Pro Lys Asp Val Glu Pro
    1100                1105                1110
```

```
Ser His Glu Ile Ser Glu Pro Val Leu Ser Gly Thr Thr Gly Lys
1115                1120                1125

Glu Glu Ser Glu Leu Leu Lys Ser Lys Ser Ile Glu Thr Lys Gly
1130                1135                1140

Glu Thr Asp Pro Arg Ser Asn Asp Gln Glu Asp Ala Thr Asp Asp
1145                1150                1155

Val Val Glu Asn Ser Arg Asp Asp Asn Asn Ser Leu Ser Asn Ser
1160                1165                1170

Val Asp Asn Gln Ser Asn Val Leu Asn Arg Glu Asp Pro Ile Ala
1175                1180                1185

Ser Glu Thr Glu Val Val Ser Glu Pro Glu Asp Ser Ser Arg Ile
1190                1195                1200

Met Thr Thr Glu Val Pro Ser Thr Thr Val Lys Pro Pro Asp Glu
1205                1210                1215

Lys Arg Ser Glu Glu Val Gly Glu Lys Glu Ala Lys Glu Ile Lys
1220                1225                1230

Val Glu Pro Val Val Pro Arg Ala Ile Gly Glu Pro Met Glu Asn
1235                1240                1245

Ser Val Ser Val Gln Ser Pro Pro Asn Val Glu Asp Val Glu Lys
1250                1255                1260

Glu Thr Leu Ile Ser Glu Asn Asn Gly Leu His Asn Asp Thr His
1265                1270                1275

Arg Gly Asn Ile Ser Glu Lys Asp Leu Ile Asp Ile His Leu Leu
1280                1285                1290

Arg Asn Glu Ala Gly Ser Thr Ile Leu Asp Asp Ser Arg Arg Asn
1295                1300                1305

Gly Glu Met Thr Glu Gly Ser Glu Ser Asp Val Gly Glu Leu Gln
1310                1315                1320

Glu His Asn Phe Ser Thr Gln Gln Lys Asp Glu Lys Asp Phe Asp
1325                1330                1335

Gln Ile Ala Ser Asp Arg Glu Lys Glu Glu Ile Gln Lys Leu Leu
1340                1345                1350

Asn Ile Gly His Glu Glu Asp Glu Asp Val Leu Lys Met Asp Arg
1355                1360                1365

Thr Glu Asp Ser Met Ser Asp Gly Val Asn Ser His Leu Tyr Tyr
1370                1375                1380

Asn Asn Leu Ser Ser Glu Glu Lys Met Glu Gln Tyr Asn Asn Arg
1385                1390                1395

Asp Ala Ser Lys Asp Arg Glu Glu Ile Leu Asn Arg Ser Asn Thr
1400                1405                1410

Asn Thr Cys Ser Asn Glu His Ser Leu Lys Tyr Cys Gln Tyr Met
1415                1420                1425

Glu Arg Asn Lys Asp Leu Leu Glu Thr Cys Ser Glu Asp Lys Arg
1430                1435                1440

Leu His Leu Cys Cys Glu Ile Ser Asp Tyr Cys Leu Lys Phe Phe
1445                1450                1455

Asn Pro Lys Ser Ile Glu Tyr Phe Asp Cys Thr Gln Lys Glu Phe
1460                1465                1470

Asp Asp Pro Thr Tyr Asn Cys Phe Arg Lys Gln Arg Phe Thr Ser
1475                1480                1485

Met His Tyr Ile Ala Gly Gly Ile Ile Ala Leu Leu Leu Phe
1490                1495                1500

Ile Leu Gly Ser Ala Ser Tyr Arg Lys Asn Leu Asp Asp Glu Lys
```

-continued

```
                   1505                1510                1515
Gly Phe  Tyr Asp Ser Asn  Leu Asn Asp Ser  Ala Phe Glu Tyr Asn
        1520                 1525                1530

Asn Asn  Lys Tyr Asn Lys  Leu Pro Tyr Met  Val Val Asp Gln Gln
        1535                 1540                1545

Ile Asn  Val Val Asn Ser  Asp Leu Tyr Ser  Glu Gly Ile Tyr Asp
        1550                 1555                1560

Asp Thr  Thr Thr Phe
        1565
```

<210> SEQ ID NO 13
<211> LENGTH: 24
<212> TYPE: DNA
<213> ORGANISM: artificial sequence
<220> FEATURE:
<223> OTHER INFORMATION: sequence is completely synthesized

<400> SEQUENCE: 13
cctggagccc gtcagtatcg gcgg                                              24

<210> SEQ ID NO 14
<211> LENGTH: 23
<212> TYPE: DNA
<213> ORGANISM: artificial sequence
<220> FEATURE:
<223> OTHER INFORMATION: sequence is completely synthesized

<400> SEQUENCE: 14
ggtagcgacc ggcgctcagc tgg                                               23

<210> SEQ ID NO 15
<211> LENGTH: 25
<212> TYPE: DNA
<213> ORGANISM: artificial sequence
<220> FEATURE:
<223> OTHER INFORMATION: sequence is completely synthesized

<400> SEQUENCE: 15
aaaagtgatg atagaaatgc ttgtg                                             25

<210> SEQ ID NO 16
<211> LENGTH: 25
<212> TYPE: DNA
<213> ORGANISM: artificial sequence
<220> FEATURE:
<223> OTHER INFORMATION: sequence is completely synthesized

<400> SEQUENCE: 16
ttttgttgat cttacttatt tcacc                                             25

<210> SEQ ID NO 17
<211> LENGTH: 22
<212> TYPE: DNA
<213> ORGANISM: artificial sequence
<220> FEATURE:
<223> OTHER INFORMATION: sequence is completely synthesized

<400> SEQUENCE: 17
cggaatcagg tttaaatcca ac                                                22

<210> SEQ ID NO 18
<211> LENGTH: 21
<212> TYPE: DNA
<213> ORGANISM: artificial sequence

```
-continued

<220> FEATURE:
<223> OTHER INFORMATION: sequence is completely synthesized

<400> SEQUENCE: 18
agatcgtttt tcatcagggg g                                              21
```